US008137695B2

(12) United States Patent
Rozema et al.

(10) Patent No.: US 8,137,695 B2
(45) Date of Patent: Mar. 20, 2012

(54) POLYCONJUGATES FOR IN VIVO DELIVERY OF POLYNUCLEOTIDES

(75) Inventors: David B. Rozema, Middleton, WI (US); James E. Hagstrom, Middleton, WI (US); Jason Klein, Madison, WI (US); David L. Lewis, Madison, WI (US); Sean D. Monahan, Lake Forest Park, WI (US); Darren H. Wakefield, Fitchburg, WI (US); Jon A. Wolff, Madison, WI (US); So Wong, Oregon, WI (US)

(73) Assignee: Arrowhead Madison Inc., Madison, WI (US)

( * ) Notice: Subject to any disclaimer, the term of this patent is extended or adjusted under 35 U.S.C. 154(b) by 0 days.

(21) Appl. No.: 11/840,468

(22) Filed: Aug. 17, 2007

(65) Prior Publication Data

US 2008/0152661 A1    Jun. 26, 2008

Related U.S. Application Data

(60) Provisional application No. 60/822,833, filed on Aug. 18, 2006, provisional application No. 60/915,868, filed on May 3, 2007.

(51) Int. Cl.
*A61K 9/14* (2006.01)
*C07H 21/02* (2006.01)
*C07K 1/00* (2006.01)

(52) U.S. Cl. ........ 424/486; 536/24.5; 530/333; 530/345

(58) Field of Classification Search .................. None
See application file for complete search history.

(56) References Cited

U.S. PATENT DOCUMENTS

| | | | |
|---|---|---|---|
| 4,587,044 A | 5/1986 | Miller et al. | |
| 4,904,582 A | 2/1990 | Tullis | |
| 5,138,045 A | 8/1992 | Cook et al. | |
| 5,166,320 A | 11/1992 | Wu et al. | |
| 5,547,932 A | 8/1996 | Curiel et al. | |
| 5,574,142 A | 11/1996 | Meyer et al. | |
| 5,877,309 A | 3/1999 | McKay et al. | |
| 5,994,316 A | 11/1999 | Lollo et al. | |
| 5,994,517 A | 11/1999 | Ts'o et al. | |
| 6,020,457 A | 2/2000 | Klimash et al. | |
| 6,300,317 B1 | 10/2001 | Szoka et al. | |
| 6,300,319 B1 | 10/2001 | Manoharan | |
| 6,312,727 B1 | 11/2001 | Schacht et al. | |
| 6,773,920 B1 | 8/2004 | Dalby et al. | |
| 6,887,906 B1 | 5/2005 | Teng et al. | |
| 7,019,113 B2 * | 3/2006 | Rozema et al. ............ | 530/333 |
| 7,176,303 B2 | 2/2007 | Freier et al. | |
| 7,176,304 B2 | 2/2007 | McSwiggen et al. | |
| 7,442,764 B2 * | 10/2008 | Rozema et al. ............ | 530/345 |
| 2002/0082198 A1 | 6/2002 | Sakurai et al. | |
| 2002/0165183 A1 | 11/2002 | Herweijer et al. | |
| 2003/0072794 A1 | 4/2003 | Boulikas | |
| 2003/0157030 A1 | 8/2003 | David et al. | |
| 2003/0220289 A1 | 11/2003 | Monahan et al. | |
| 2003/0229034 A1 * | 12/2003 | Waugh et al. ............... | 514/44 |
| 2004/0071654 A1 * | 4/2004 | Anderson et al. .......... | 424/78.37 |
| 2004/0072785 A1 | 4/2004 | Wolff et al. | |
| 2004/0110296 A1 | 6/2004 | Vargeese et al. | |
| 2004/0156909 A1 * | 8/2004 | Rozema et al. ............... | 424/486 |
| 2004/0162260 A1 * | 8/2004 | Rozema et al. ................ | 514/44 |
| 2004/0198687 A1 * | 10/2004 | Rozema et al. ................ | 514/44 |
| 2004/0204377 A1 | 10/2004 | Rana | |
| 2004/0249178 A1 | 12/2004 | Vargeese et al. | |
| 2005/0008617 A1 | 1/2005 | Chen et al. | |
| 2005/0037496 A1 | 2/2005 | Rozema et al. | |
| 2005/0119470 A1 | 6/2005 | Manoharan et al. | |
| 2006/0008907 A1 | 1/2006 | Friedman et al. | |
| 2006/0040882 A1 | 2/2006 | Chen et al. | |
| 2006/0134189 A1 | 6/2006 | MacLachlan et al. | |
| 2006/0154867 A1 * | 7/2006 | Sokoloff et al. ................ | 514/12 |
| 2006/0166234 A1 | 7/2006 | Robertson et al. | |
| 2006/0166881 A1 | 7/2006 | Hotchkiss et al. | |
| 2006/0240092 A1 | 10/2006 | Breitenkamp et al. | |
| 2006/0247429 A1 | 11/2006 | McSwiggan et al. | |
| 2007/0003609 A1 | 1/2007 | Collin-Djangone et al. | |
| 2007/0036865 A1 * | 2/2007 | Rozema et al. ............... | 424/486 |
| 2007/0041932 A1 | 2/2007 | Jeong et al. | |
| 2008/0112916 A1 * | 5/2008 | Wagner et al. ............... | 424/78.3 |

OTHER PUBLICATIONS

Ashwell G et al. "Carbohydrate-specific receptors of the liver." Ann Rev Biochem. 1982; vol. 51, p. 531-554.

Chiu MH et al. "In Vivo Targeting Function of N-Linked Oligosaccharides with Terminating Galactose and N-Acetylgalactosamine Residues" J Biol Chem, 1994, vol. 269, p. 16195-16202.

Dash PR et al. "Decreased binding to proteins and cells of polymeric gene delivery vectors surface modified with a multivalent hydrophilic polymer and retargeting through attachment of transferrin." J Biol Chem. 2000; vol. 275, No. 6, p. 3793-3802.

Diebold et al., "Mannose Polyethylenimine Conjugates for Targeted DNA Delivery into Dendritic Cells," Journal of Biological Chemistry, 1999; vol. 274, p. 19087-19094.

Ferruti, P et al. "Amphoteric Linear Poly(amido-amine)s as Endosomolytic Polymers: Correlation between Physicochemical and Biological Properties" Macromolecules; 2000; vol. 33, No. 21, p. 7793-7800.

Ii M et al. "Molecular Cloning and Sequence Analysis of cDNA Encoding the Macrophage Lectin Specific for Galactose and N-Acetylgalactosamine", J Biol Chem 1990, vol. 265, p. 11295-11298.

Kim EM et al. "Hepatocyte-targeted nuclear imaging using 99mTc-galactosylated chitosan: conjugation, targeting, and biodistribution." J Nucl Med 2005; vol. 46, No. 1, p. 141-145.

Kirby AJ "Effective Molarities for Intramolecular Reactions" Advances in Physical and Organic Chemistry 1980, vol. 17, p. 183.

(Continued)

*Primary Examiner* — Richard Schnizer
(74) *Attorney, Agent, or Firm* — Kirk Ekena

(57) ABSTRACT

The present invention is directed to compounds, compositions, and methods useful for delivering polynucleotides or other cell-impermeable molecules to mammalian cells. Described are polyconjugates systems that incorporate targeting, anti-opsonization, anti-aggregation, and transfection activities into small biocompatible in vivo delivery vehicles. The use of multiple reversible linkages connecting component parts provides for physiologically responsive activity modulation.

27 Claims, 24 Drawing Sheets

OTHER PUBLICATIONS

Lee et al. "New Synthetic Cluster Ligands for Galactose/N-Acetylgalactosamine-Specific Lectin of Mammalian Liver," Biochemistry 1984; vol. 23, p. 4255-4261.

Letsinger RL et al. "Cholesteryl-conjugated oligonucleotides: Synthesis, properties, and activity as inhibitors of replication of human immunodeficiency virus in cell culture", Proc. Natl. Acad. Sci. USA, 1989, vol. 86, p. 6553-6556.

Manoharan M et al. "Cholic Acid-Oligonucleotide Conjugates for Antisense Applications", Bioorg. Med. Chem. Letts., 1994, vol. 4, p. 1053-1060.

Manoharan M et al. "Oligonucleotide conjugates: Alternation of the Pharmacokinetic Properties of Antisense Agents", Nucleosides & Nucleotides, 1995, vol. 14, p. 969-973.

Meade BR et al. "Exogenous siRNA delivery using peptide transduction domains/cell penetrating peptides" Advanced Drug Delivery Reviews, 2007; vol. 59, No. 2-3, p. 134-140.

Meyer M et al. "Recent Developments in the Application of Plasmid DNA-Based Vectors and Small Interfering RNA Therapeutics for Cancer" Human Gene Therapy. 2006, vol. 17, No. 11 p. 1062-1076.

Murthy S. et al. "Design and synthesis of pH-responsive polymeric carriers that target uptake and enhance the intracellular delivery of oligonucleotides" Journal of Controlled Release, 2003; vol. 89, p. 356-374.

OupickýD et al. "Development of Long-circulating Polyelectrolyte Complexes for Systemic Delivery of Genes" Journal of Drug Targeting, 2002; vol. 10, No. 2, p. 93-98.

Pimm MV et al. "Targeting of N-(2-hydroxypropyl)methacrylamide copolymer-doxorubicin conjugate to the hepatocyte galactose-receptor in mice: visualisation and quantification by gamma scintigraphy as a basis for clinical targeting studies." (1993) J Drug Target 1993, vol. 1 No. 2, p. 125-131.

Plank et al. "Gene Transfer into Hepatocytes Using Asialoglycoprotein Receptor Mediated Endocytosis of DNA Complexed with an Artificial Tetra-Antennary Galactose Ligand", Bioconjugate Chem., 1992, vol. 3, 533-539.

Saito G et al. "Drug delivery strategy utilizing conjugation via reversible disulfide linkages: role and site of cellular reducing activities" Advanced Drug Delivery Reviews 2003; vol. 55, p. 199-215.

Saito G et al. "Enhanced cytosolic delivery of plasmid DNA by a sulfhydryl-activatable listeriolysin O/protamines conjugate utilizing cellular reducing potential" Gene Therapy 2003; vol. 10, p. 72-83.

Schlepper-Schafer, Jutta et al. "Endocytosis Via Galactose Receptors in Vivo." Experimental Cell Research 1986; vol. 165, p. 494-506.

Schwartz AL et al. "The Hepatic Asialoglycoprotein Receptor" Crit Rev Biochem. 1984; vol. 16, p. 207-233.

Shea RG et al. "Synthesis, hybridization properties and antiviral activity of lipid-oligonucleotide conjugates" Nucl. Acids Res. 1990, vol. 18, p. 3777-3783.

Svinarchuk FP et al. "Inhibition of HIV proliferation in MT-4 cells by antisense oligonucleotide conjugated to lipophilic groups" Biochimie, 1993, vol. 75, p. 49-54.

Li W et al. "Low-pH-sensitive poly(ethylene glycol) (PEG)-stabilized plasmid nanolipoparticles: effects of PEG chain length, lipid composition and assembly conditions on gene delivery" Journal of Gene Medicine 2005; vol. 7, No. 1, p. 67-79.

Torchilin VP "Micellar nanocarriers: pharmaceutical perspectives." Pharm Res. 2007; vol. 24, No. 1, p. 1-16.

Watanabe Y et al. "Functional evaluation of poly-(N-p-vinylbenzyl-O-beta-D-galactopyranosyl-[1-4]-D-gluconamide) (PVLA) as a liver specific carrier." (2000) J Biomater Sci Polym Ed 2000; vol. 11, No. 8, p. 833-848.

Wu J et al. "Targeting hepatocytes for drug and gene delivery: emerging novel approaches and applications." Front Biosci. 2002;vol. 7, p. 717-725.

Xu P "Targeted Charge-Reversal Nanoparticles for Nuclear Drug Delivery" Angew Chem Int Ed 2006; vol. 46, p. 4999-5002.

* cited by examiner

CDM-LBA negatively charged
upon maleamate formation galactose  gluconic acid  ethyleneoxide spacer   CDM

CDM-Pip-LBA zwitterionic upon maleamate
formation from negative maleamate
and positive amine group piperazine spacer

CDM-PEG

CDM-NAG:

Figure 7. Formulation of siRNA-polymer conjugates

A.

B.

A.

B.

C.

A.
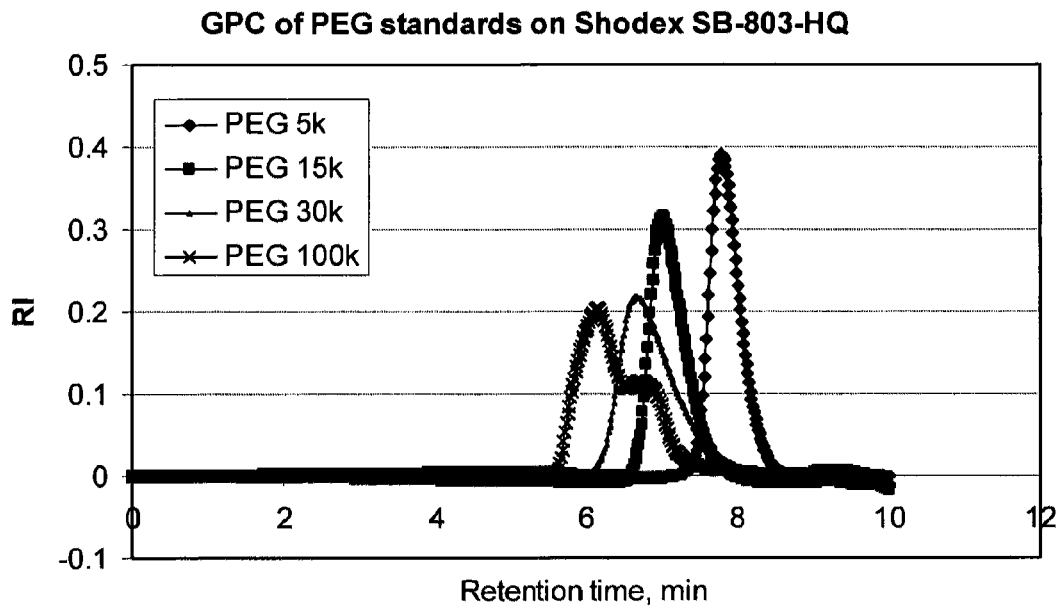
B.
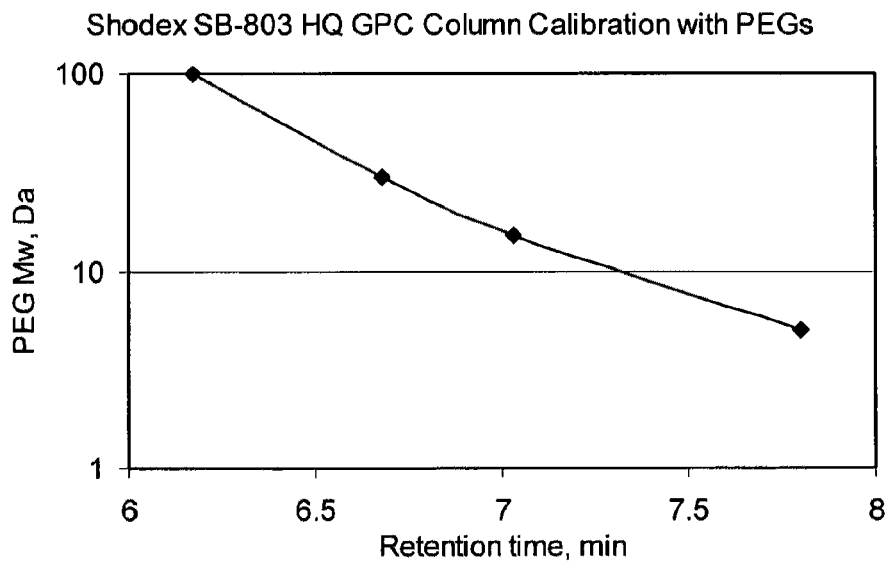
FIG. 17 A-B

C.

A.
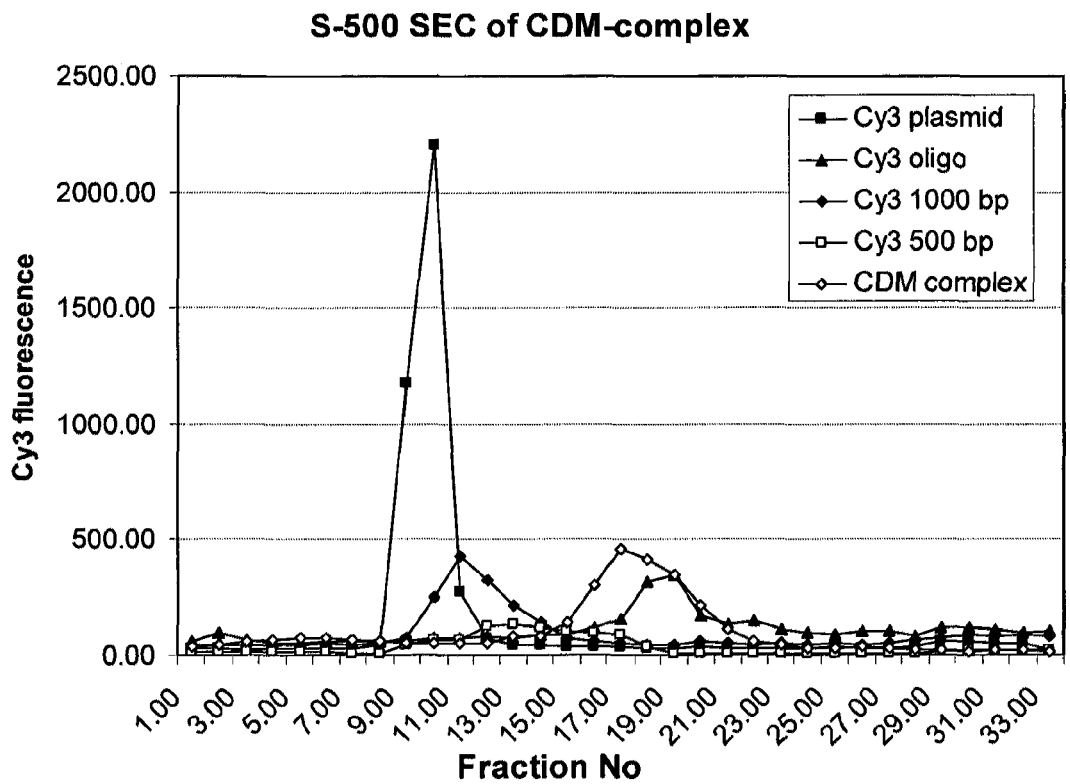
B.
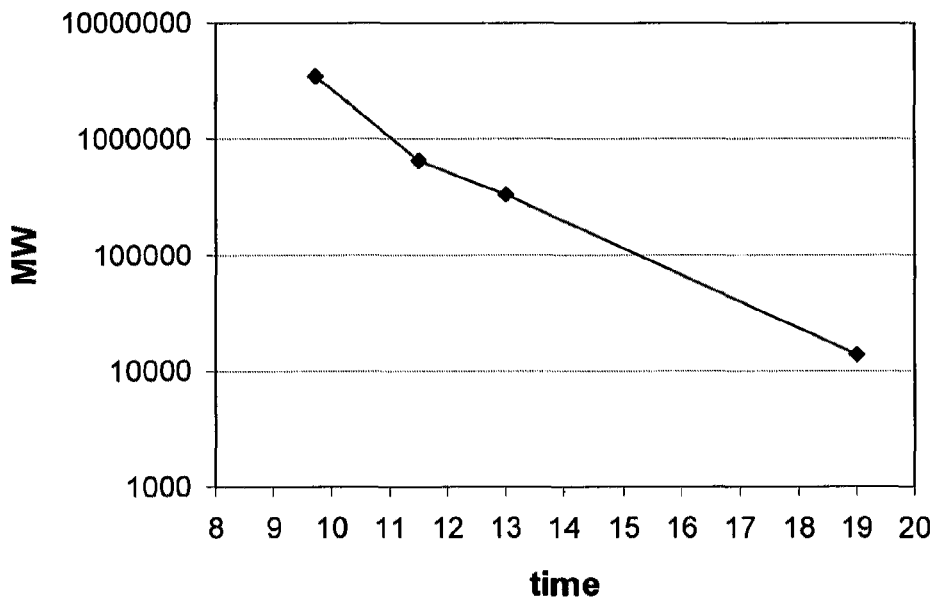
FIG. 18 A-B

C.

POLYCONJUGATES FOR IN VIVO DELIVERY OF POLYNUCLEOTIDES

CROSS-REFERENCE TO RELATED APPLICATIONS

This application claims the benefit of U.S. Provisional Application No. 60/822,833 filed Aug. 18, 2006, and U.S. Provisional Application No. 60/915,868 filed May 3, 2007.

BACKGROUND OF THE INVENTION

The delivery of polynucleotide and other membrane impermeable compounds into living cells is highly restricted by the complex membrane systems of the cell. Drugs used in antisense and gene therapies are relatively large hydrophilic polymers and are frequently highly negatively charged as well. Both of these physical characteristics preclude their direct diffusion across the cell membrane. For this reason, the major barrier to polynucleotide delivery is the delivery of the polynucleotide to the cellular interior. Numerous transfection reagents have been developed to deliver polynucleotides to cells in vitro. However, in vivo delivery of polynucleotides is complicated by toxicity, serum interactions, and poor targeting of transfection reagents that are effective in vitro. Transfection reagents that work well in vitro, cationic polymers and lipids, typically destabilize cell membranes and form large particles. The cationic charge of transfection reagent facilitates nucleic acid binding as well as cell binding. Destabilization of membranes facilitates delivery of the membrane impermeable polynucleotide across a cell membrane. These properties render transfection reagents ineffective or toxic in vivo. Cationic charge results in interaction with serum components, which causes destabilization of the polynucleotide-transfection reagent interaction and poor bioavailability and targeting. Cationic charge may also lead to in vivo toxicity. Membrane activity of transfection reagent, which can be effective in vitro, often leads to toxicity in vivo.

For in vivo delivery, a transfection complex (transfection reagent in association with the nucleic acid to be delivered) should be small, less than 100 nm in diameter, and preferably less than 50 nm. Even smaller complexes, less that 20 nm or less than 10 nm would be more useful yet. Transfection complexes larger than 100 nm have very little access to cells other than blood vessel cells in vivo. In vitro complexes are also positively charged. This positive charge is necessary for attachment of the complex to the cell and for membrane fusion, destabilization or disruption. Cationic charge on in vivo transfection complexes leads to adverse serum interactions and therefore poor bioavailability. Near neutral or negatively charged complexes would have better in vivo distribution and targeting capabilities. However, in vitro transfection complexes associate with nucleic acid via charge-charge (electrostatic) interactions. Negatively charged polymers and lipids do not interact with negatively charged nucleic acids. Further, these electrostatic complexes tend to aggregate or fall apart when exposed to physiological salt concentrations or serum components. Finally, transfection complexes that are effective in vitro are often toxic in vivo. Polymers and lipids used for transfection disrupt or destabilize cell membranes. Balancing this activity with nucleic acid delivery is more easily attained in vitro than in vivo.

While several groups have made incremental improvements towards improving gene delivery to cells in vivo, there remains a need for a formulation that effectively delivers a polynucleotide together with a delivery agent to a target cell without the toxicity normally associated with in vivo administration of transfection reagents. The present invention provides compositions and methods for the delivery and release of a polynucleotide to a cell using biologically labile conjugate delivery systems.

SUMMARY OF THE INVENTION

In a preferred embodiment, the invention features a composition for delivering a polynucleotide to a cell in vivo comprising a reversibly masked membrane active polymer reversibly conjugated to a polynucleotide. The polymer is attached, via one or more first reversible covalent linkages, to one or more masking agents and is further attached, via one or more second reversible covalent linkages, to one or more polynucleotides. The first and second reversible covalent linkages may comprise reversible bonds that are cleaved under the same or similar conditions or they may cleaved under distinct conditions, i.e. they may comprise orthogonal reversible bonds. The polynucleotide-polymer conjugate is administered to a mammal in a pharmaceutically acceptable carrier or diluent.

In a preferred embodiment are disclosed membrane active polymers comprising: polyvinylether random copolymers. The polyvinylether copolymers may be synthesized from two, three, or more different monomers. Monomers may be selected from the list comprising: protected amino vinyl ether such as phthalimido-containing vinyl ethers, butyl vinyl ether, dodecyl vinyl ether, octadecyl vinyl ether. A preferred polyvinylether random copolymer comprises three monomers: an amine containing monomer, a butyl vinyl ether, and an octadecyl vinyl ether.

In a preferred embodiment, one or more biophysical characteristics of the membrane active polymer are reversibly shielded or modified by a masking agent. Masking agents may be selected from the group comprising steric stabilizers, targeting groups and charge modifying agents. The masking agent can improve biodistribution or targeting of the polymer-polynucleotide conjugate by inhibiting non-specific interactions of the polymer with serum components or non-target cells. The masking agent can also reduce aggregation of the polymer or polymer-polynucleotide conjugate. Masking agents containing targeting groups can enhance cell-specific targeting or cell internalization by targeting the conjugate system to a cell surface receptor. The masking agent can be conjugated to the membrane active polymer prior to or subsequence to conjugation of the polymer to a polynucleotide.

In a preferred embodiment, the polynucleotide that may be delivered to cells using the described conjugate systems may be selected from the group comprising: DNA, RNA, blocking polynucleotides, antisense oligonucleotides, plasmids, expression vectors, oligonucleotides, siRNA, microRNA, mRNA, shRNA and ribozymes.

In a preferred embodiment, the masking agent(s) and the polynucleotide(s) are covalently linked to the membrane active polymer via reversible linkages. While masking of the polymer, and attachment of the polynucleotide to the polymer, are important, these attachments can interfere with transfection activity of the polymer or the activity of the polynucleotide. By attaching the masking agent and the polynucleotide to the polymer via reversibly linkages that are cleaved at an appropriate time, activity is restored to the polymer and the polynucleotide is released. Reversible covalent linkages contain reversible or labile bonds which may be selected from the group comprising: physiologically labile bonds, cellular physiologically labile bonds, pH labile bonds, very pH labile bonds, extremely pH labile bonds, enzymatically cleavable bonds, and disulfide bonds. The presence of two reversible linkages connecting the polymer to the polynucleotide and a masking agent provides for co-delivery of the polynucleotide with a delivery polymer and selective targeting and inactivation of the delivery polymer by the masking agent. Reversibility of the linkages provides for release of polynucleotide from the membrane active polymer and selective activation of the membrane active polymer.

In a preferred embodiment, we describe a composition comprising: a delivery polymer covalently linked to: a) one or more targeting groups, steric stabilizers or charge modifiers via one or more reversible linkages; and, b) one or more polynucleotides via one or more reversible linkages. In one embodiment, the targeting agent, steric stabilizer, or charge modifier reversible covalent linkage is orthogonal to the polynucleotide reversible covalent linkage.

In a preferred embodiment, we describe a polymer conjugate system for delivering a polynucleotide to a cell and releasing the polynucleotide into the cell comprising: the polynucleotide reversibly conjugated to a membrane active polymer which is itself reversibly conjugated to a masking agent. The conjugation bonds may be the same or they may be different. In addition, the conjugation bonds may be cleaved under the same or different conditions.

In a preferred embodiment, we describe a polymer conjugate system for delivering a membrane impermeable molecule to a cell and releasing the molecule in the cell. The polymer conjugate system comprises the membrane impermeable molecule reversibly linked to a membrane active polymer wherein a plurality of masking agents are linked to the membrane active polymer via reversible covalent bonds. Membrane active polymers may be toxic or may not be targeted when applied in vivo. Reversible attachment of a masking agent reversibly inhibits or alters membrane interactions, serum interactions, cell interactions, toxicity, or charge of the polymer. A preferred reversible covalent bond comprises: a labile bond, a physiologically labile bond or a bond cleavable under mammalian intracellular conditions. A preferred labile bond comprises a pH labile bond. A preferred pH labile bond comprises a maleamate bond. Another preferred labile bond comprises a disulfide bond. Membrane impermeable molecules include, but are not limited to: polynucleotides, proteins, antibodies, and membranes impermeable drugs.

In a preferred embodiment, a polynucleotide is attached to the polymer in the presence of an excess of polymer. The excess polymer may aid in formulation of the polynucleotide-polymer conjugate. The excess polymer may reduce aggregation of the conjugate during formulation of the conjugate. The polynucleotide-polymer conjugate may be separated from the excess polymer prior to administration of the conjugate to the cell or organism. Alternatively, the polynucleotide-polymer conjugate may be co-administered with the excess polymer to the cell or organism. The excess polymer may be the same as the polymer or it may be different.

In a preferred embodiment, the polymer conjugates of the invention may be used for in vitro delivery of a polynucleotide or other membrane impermeable molecule. For in vitro delivery, reversible masking of the polymer enhances transfection activity of some otherwise ineffective polyamines, such as polylysine. Reversibly masking can also enhance the utility of other membrane active polymers by reducing their toxicity or limiting their membrane disruptive character to endosomes.

In a preferred embodiment, we describe a system for delivering a polynucleotide to a cell in vivo comprising: covalently linking a targeting group to a polynucleotide, covalently linking a second targeting group to a membrane active polymer, and injecting the polynucleotide and membrane active polymer into an organism.

Further objects, features, and advantages of the invention will be apparent from the following detailed description when taken in conjunction with the accompanying drawings.

DETAILED DESCRIPTION OF THE INVENTION

Figure 1:
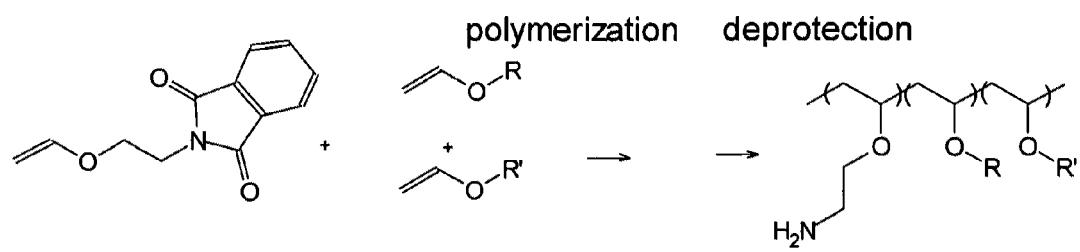
FIG. 1. Reaction scheme for polymerization of polyvinylether polymers.

The present invention is directed to compounds, compositions, and methods useful for delivering polynucleotides or other cell-impermeable molecules to mammalian cells. Described herein is a polyconjugate system for delivering polynucleotides or other membrane impermeable molecules to cells in vivo. The polyconjugate system incorporates targeting, anti-opsonization, anti-aggregation, and transfection activities into a small sub 50 nanometer delivery vehicle. A key component of the system is the reversibility of bonds connecting the component parts.

A first component of the described in vivo polynucleotide delivery conjugates comprises a physiologically reversible covalent linkage of the polynucleotide to a membrane active polymer. Covalent attachment of the polynucleotide to the membrane active polymer ensures that the polynucleotide is not readily dissociated from the polymer when administered in vivo, or ex vivo in the presence of serum, and thus provides for co-delivery of the polynucleotide with the membrane active polymer to the target cell. Covalent attachment of a polynucleotide to a polymer can, however, render the polynucleotide inactive. Attachment of the polynucleotide to the membrane active polymer is therefore accomplished through a physiologically reversible linkage or bond. By using a physiologically reversible linkage, the polynucleotide can be cleaved from the polymer, releasing the polynucleotide to engage in functional interactions with cell components. By choosing an appropriate reversible linkage, it is possible to form a conjugate that releases the polynucleotide only after it has been delivered to a desired location, such as a cell cytoplasm.

A second component of the described in vivo polynucleotide delivery conjugates comprises a reversible modification of the membrane active polymer. Reversible modification of the membrane active polymer reduces non-productive serum and non-target cell interactions and reduces toxicity. The masking agent can also add a desired function to the conjugate such as enhancing target cell interaction or enhancing endocytosis of the conjugate. The polymer is masked by covalent attachment of a masking agent to the polymer via a physiologically reversible covalent linkage. The masking agent can be a steric stabilizer, targeting group, or charge modifier. The masking agents can shield the polymer from non-specific interactions, increase circulation time, enhance specific interactions, inhibit toxicity, or alter the charge of the polymer. Each of these modifications may alter the membrane activity of the polymer, rendering the modified polymer unable to facilitate delivery of the polynucleotide. Attachment of the masking agent to the membrane active polymer is therefore accomplished through a physiologically reversible bond. By using a physiologically reversible linkage, the masking agent can be cleaved from the polymer, thereby unmasking the polymer and restoring activity of the unmasked polymer. By choosing an appropriate reversible linkage, it is possible to form a conjugate that restores activity of the membrane active polymer after it has been delivered or targeted to a desired cell type or cellular location.

The invention includes conjugate delivery systems of the general structure:

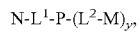

$$N\text{-}L^1\text{-}P\text{-}(L^2\text{-}M)_y,$$

wherein N is a polynucleotide or other cell impermeable molecule, $L^1$ is a reversible linkage, P is a polymer, $L^2$ is a second reversible linkage, and M is a masking agent. Masking agent M shields or modifies a property or interaction of P. y is an integer greater than 0. A preferred polymer is a membrane active polymer. Another preferred polymer is a transfection polymer. A plurality of masking agents may be linked to a single polymer. The plurality of masking agents may be linked to the polymer via a plurality of reversibly linkages. Upon cleavage of reversible linkage $L^2$, the masked property or interaction is restored to polymer P. Masking agent M can add an activity, such as cell receptor binding, to polymer P. The reversible bond of $L^1$ may be the same or different than (orthogonal to) the reversible bond of $L^2$. The reversible bond of reversible linkage $L^1$ or $L^2$ is chosen such that cleavage occurs in a desired physiological condition, such as that present in a desired tissue, organ, and sub-cellular location or in response to the addition of a pharmaceutically acceptable exogenous agent. Polynucleotide N and masking agent M may be attached to polymer P anywhere along the length of polymer P.

Polymers

A polymer is a molecule built up by repetitive bonding together of smaller units called monomers. A polymer can be linear, branched network, star, comb, or ladder type. The main chain of a polymer is composed of the atoms whose bonds are required for propagation of polymer length. For example, in poly-L-lysine, the carbonyl carbon, α-carbon, and α-amine groups are required for the length of the polymer and are therefore main chain atoms. A side chain of a polymer is composed of the atoms whose bonds are not required for propagation of polymer length.

A polymer can be a homopolymer in which a single monomer is used or a polymer can be copolymer in which two or more different monomers are used. Copolymers may by alternating, random (statistical), block and graft (comb).

Alternating polymers contain monomers in a defined repeating order, such as $\text{-}[A\text{-}B]_n\text{-}$. The monomers of alternating polymers typically do not homopolymerize, instead reacting together to yield the alternating copolymer.

The monomers in random copolymers have no definite order or arrangement along any given chain, such as: $\text{-}A_n\text{-}B_m\text{-}$. The general compositions of such polymers are reflective of the ratio of input monomers. However, the exact ratio of one monomer to another may differ between chains. The distribution of monomers may also differ along the length of a single polymer. Also, the chemical properties of a monomer may affect its rate of incorporation into a random copolymer and its distribution within the polymer. Thus, while the ratio of monomers in a random polymer is dependent on the input ratio of monomer, the input ratio may not match exactly the ratio of incorporated monomers.

A block polymer has a segment or block of one polymer (polyA) followed by a segment or block of a second polymer (polyB): i.e., -polyA-polyB-. The result is that different polymer chains are joined in a head-to-tail configuration. Thus, a block polymer is a linear arrangement of blocks of different monomer composition. Generally, though not required, the polymer blocks are homopolymers with polymer A being composed of a different monomer than polymer B. A diblock copolymer is polyA-polyB, and a triblock copolymer is polyA-polyB-polyA. If A is a hydrophilic group and B is hydrophobic group, the resultant block copolymer can be regarded a polymeric surfactant. A graft polymer is a type of block copolymer in which the chains of one monomer are grafted onto side chains of the other monomer, as in (where n, m, x, y, and z are integers):

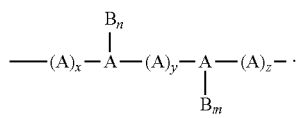

Monomers

A wide variety of monomers can be used in polymerization processes. Monomers can be cationic, anionic, zwitterionic, hydrophilic, hydrophobic, lipophilic, amphipathic, or amphoteric. Monomers can themselves be polymers. Monomers can contain chemical groups that can be modified before or after polymerization. Such monomers may have reactive groups selected from the group comprising: amine (primary, secondary, and tertiary), amide, carboxylic acid, ester, hydrazine, hydrazide, hydroxylamine, alkyl halide, aldehyde, and ketone. Preferably, the reactive group can be modified after conjugation of the polynucleotide, or in aqueous solution.

To those skilled in the art of polymerization, there are several categories of polymerization processes. For example, the polymerization can be chain or step.

Step Polymerization

In step polymerization, the polymerization occurs in a stepwise fashion. Polymer growth occurs by reaction between monomers, oligomers and polymers. No initiator is needed since the same reaction occurs throughout and there is no termination step, so that the end groups are still reactive. The polymerization rate decreases as the functional groups are consumed.

A polymer can be created using step polymerization by using monomers that have two reactive groups (A and B) in the same monomer (heterobifunctional), wherein A comprises a reactive group and B comprises an A-reactive group (a reactive group which forms a covalently bond with A). Polymerization of A-B yields $-[A-B]_n-$. Reactive groups A and B can be joined by a covalent bond or a plurality of covalent bonds, thereby forming the polymer monomer. A polymer can also be created using step polymerization by using homobifunctional monomers such that A-A+B-B yields $-[A-A-B-B]_n-$. Generally, these reactions can involve acylation or alkylation. The two reactive groups of a monomer can be joined by a single covalent bond or a plurality of covalent bonds.

If reactive group A is an amine then B is an amine-reactive group, which can be selected from the group comprising: isothiocyanate, isocyanate, acyl azide, N-hydroxy-succinimide, sulfonyl chloride, aldehyde (including formaldehyde and glutaraldehyde), ketone, epoxide, carbonate, imidoester, carboxylate activated with a carbodiimide, alkylphosphate, arylhalides (difluoro-dinitrobenzene), anhydride, acid halide, p-nitrophenyl ester, o-nitrophenyl ester, pentachlorophenyl ester, pentafluorophenyl ester, carbonyl imidazole, carbonyl pyridinium, and carbonyl dimethylaminopyridinium. In other terms when reactive group A is an amine then B can be acylating or alkylating agent or amination agent.

If reactive group A is a sulfhydryl(thiol) then B is a thiol-reactive group, which can be select from the group comprising: iodoacetyl derivative, maleimide, aziridine derivative, acryloyl derivative, fluorobenzene derivatives, and disulfide derivative (such as a pyridyl disulfide or 5-thio-2-nitrobenzoic acid (TNB) derivatives).

If reactive group A is carboxylate then reactive group B is a carboxylate-reactive group, which can be selected from the group comprising: diazoacetate and an amine in which a carbodiimide is used. Other additives may be utilized such as carbonyldiimidazole, dimethylamino pyridine (DMAP), N-hydroxysuccinimide or alcohol using carbodiimide and DMAP.

If reactive group A is a hydroxyl then reactive group B is a hydroxyl-reactive group, which can be selected from the group comprising: epoxide, oxirane, an activated carbamate, activated ester, and alkyl halide.

If reactive group A is an aldehyde or ketone then reactive group B is a aldehyde- or ketone-reactive group, which can be selected from the group comprising: hydrazine, hydrazide derivative, amine (to form a Schiff Base that may or may not be reduced by reducing agents such as $NaCNBH_3$), and hydroxyl compound.

A polymer can be created using step polymerization by using bifunctional monomers and another agent, such that that A-A plus another agent yields $-[A-A]_n-$.

If reactive group A is a sulfhydryl(thiol) group then it can be converted to disulfide bonds by oxidizing agents such as iodine ($I_2$), sodium periodate ($NaIO_4$), or oxygen ($O_2$). If reactive group A can is an amine, it can be converted to a thiol by reaction with 2-Iminothiolate (Traut's reagent) which then undergoes oxidation and disulfide formation. Disulfide derivatives (such as a pyridyl disulfide or TNB derivatives) can also be used to catalyze disulfide bond formation.

Reactive groups A or B in any of the above examples can also be a photoreactive group such as aryl azide (including halogenated aryl azide), diazo, benzophenone, alkyne, or diazirine derivative.

Reactions of the amine, hydroxyl, sulfhydryl, or carboxylate groups yield chemical bonds that are described as amides, amidines, disulfides, ethers, esters, enamines, imines, ureas, isothioureas, isoureas, sulfonamides, carbamates, alkylamine bonds (secondary amines), and carbon-nitrogen single bonds in which the carbon contains a hydroxyl group, thioether, diol, hydrazone, diazo, or sulfone.

Chain Polymerization

In chain-reaction polymerization growth of the polymer occurs by successive addition of monomer units to a limited number of growing chains. The initiation and propagation mechanisms are different and there is typically a chain-terminating step. Chain polymerization reactions can be radical, anionic, or cationic. Monomers for chain polymerization may be selected from the groups comprising: vinyl, vinyl ether, acrylate, methacrylate, acrylamide, and methacrylamide groups. Chain polymerization can also be accomplished by cycle or ring opening polymerization. Several different types of free radical initiators can be used including, but not limited to: peroxides, hydroxy peroxides, and azo compounds such as 2,2'-Azobis(-amidinopropane)dihydrochloride (AAP).

Transfection Activity

The term transfection refers to the transfer of a polynucleotide or other biologically active compound from outside a cell to inside a cell such that the polynucleotide or biologically active compound is functional. Examples of transfection reagents for delivery of polynucleotides to cells in vitro include, but are not limited to: liposomes, lipids, polyamines, calcium phosphate precipitates, histone proteins, polyethylenimine, and polyampholyte complexes, and combinations of these. Many in vitro transfection reagents are cationic, which to allows the reagent to associate with, or form a complex with, negatively charged nucleic acids via electrostatic interaction.

Membrane Active Polymers

Membrane active polymers are amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. Membrane active polymers of the invention include those polymers that facilitate delivery of a polynucleotide or other membrane impermeable molecule from outside a cell to inside the cell, and preferably to the cytoplasm of the cell. The alteration or disruption of the membrane can be functionally defined by the polymer's or compound's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Membrane active polymers that can cause disruption of endosomes or lysosomes are considered endosomolytic. The effect of membrane active polymers on a cell membrane may be transient. Membrane activity of a polymer is derived from its affinity for the membrane, which causes a denaturation or deformation of the bilayer structure. Membrane active polymers may be synthetic or non-natural amphipathic polymers. Membrane active polymers may have in vitro transfection activity. Membrane active polymers may be cationic, anionic, amphipathic, amphoteric, surface active, or combinations of these.

Delivery of a polynucleotide, or other membrane impermeable molecule, to a cell is mediated by the membrane active polymer disrupting or destabilizing the plasma membrane or an internal vesicle membrane (such as an endosome or lysosome), including forming a pore in the membrane, or disrupting endosomal or lysosomal function.

As used herein, membrane active polymers are distinct from a class of polymers termed cell penetrating peptides or polymers represented by compounds such as the arginine-rich peptide derived from the HIV TAT protein, the antennapedia peptide, VP22 peptide, transportan, arginine-rich artificial peptides, small guanidinium-rich artificial polymers and the like. While cell penetrating compounds appear to transport some molecules across a membrane, from one side of a lipid bilayer to other side of the lipid bilayer, apparently without requiring endocytosis and without disturbing the integrity of the membrane, their mechanism is not understood and the activity itself is disputed.

Endosomolytic Polymers

Endosomolytic polymers are polymers that, in response to a change in pH, are able to cause disruption or lysis of an endosome or provide for escape of a normally membrane-impermeable compound, such as a polynucleotide or protein, from a cellular internal membrane-enclosed vesicle, such as an endosome or lysosome. Endosomal release is importance for the delivery of a wide variety of molecules which are endocytosed but incapable of diffusion across cellular membranes. Endosomolytic polymers undergo a shift in their physico-chemical properties over a physiologically relevant pH range (usually pH 5.5-8). This shift can be a change in the polymer's solubility, ability to interact with other compounds, and a shift in hydrophobicity or hydrophilicity. Exemplary endosomolytic polymers can have pH-titratable groups or pH-labile groups or bonds. As used herein, pH-titratable groups reversibly accept or donate protons in water as a function of pH under physiological conditions, i.e. a pH range of 4-8. pH-titratable groups have $pK_a$'s in the range of 4-8 and act as buffers within this pH range. Thus, pH-titratable groups gain or lose charge in the lower pH environment of an endosome. Groups titratable at physiological pH can be determined experimentally by conducting an acid-base titration and experimentally determining if the group buffers within the pH-range of 4-8. Examples of groups that can exhibit buffering within this pH range include but are not limited to: carboxylic acids, imidazole, N-substituted imidazole, pyridine, phenols, and polyamines. Polymers with pH-titratable groups may disrupt internal vesicles by the so-called proton sponge effect. A reversibly masked membrane active polymer, wherein the masking agents are attached to the polymer via pH labile bonds, can therefore be considered to be an endosomolytic polymer.

A subset of endosomolytic compounds is fusogenic compounds, including fusogenic peptides. Fusogenic peptides can facilitate endosomal release of agents such as oligomeric compounds to the cytoplasm. It is believed that fusogenic peptides change conformation in acidic pH, effectively destabilizing the endosomal membrane thereby enhancing cytoplasmic delivery of endosomal contents. Example fusogenic peptides include peptides derived from polymyxin B, influenza HA2, GAL4, KALA, EALA, melittin and melittin-derived peptides, Alzheimer β-amyloid peptide, and the like.

Polyampholytes

A polyampholyte is a polymer containing both anionic and cationic monomer units. More specifically, as used herein, a polyampholyte contains a plurality of anionic monomers and a plurality of cationic units. A polyampholyte polymer may optionally contain non-ionic monomer units. In aqueous solutions polyampholytes precipitate near their isoelectric points. A polyampholyte can be formed by polymerizing anionic and cationic monomers, including polymeric monomers. Alternatively, a polyampholyte can be formed by modifying more than one, but not all, of the charged groups on a polymer. If the charged groups are reversibly modified, a reversible polyampholyte is formed.

Amphipathic

Amphipathic, or amphiphilic, polymers are well known and recognized in the art and have both hydrophilic (polar, water-soluble) and hydrophobic (non-polar, lipophilic, water-insoluble) groups or parts. Hydrophilic groups indicate in qualitative terms that the chemical moiety is water-preferring. Typically, such chemical groups are water soluble, and are hydrogen bond donors or acceptors with water. A hydrophilic group can be charged or uncharged. Charged groups can be positively charged (anionic) or negatively charged (cationic) or both. An amphipathic compound can be a polyanion, a polycation, a zwitterion, or a polyampholyte. Examples of hydrophilic groups include compounds with the following chemical moieties; carbohydrates, polyoxyethylene, certain peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to form hydrogen bonds. Lipophilic groups dissolve in fats, oils, lipids, and non-polar solvents and have little to no capacity to form hydrogen bonds. Hydrocarbons (containing 2 or more carbon atoms), certain substituted hydrocarbons, cholesterol, cholesterol derivatives, and certain peptides are examples of hydrophobic groups. As used herein, with respect to amphipathic polymers, a part is defined as a molecule derived when one covalent bond is broken and replaced by hydrogen. For example, in butyl amine, a breakage between the carbon and nitrogen bonds, with replacement with hydrogens, results in ammonia (hydrophilic) and butane (hydrophobic). However, if 1,4-diaminobutane is cleaved at nitrogen-carbon bonds, and replaced with hydrogens, the resulting molecules are again ammonia (2×) and butane. However, 1,4,-diaminobutane is not considered amphipathic because formation of the hydrophobic part requires breakage of two bonds.

A naturally occurring polymer is a polymer that can be found in nature. Examples include polynucleotides, proteins, collagen, and polysaccharides, (starches, cellulose, glycosaminoglycans, chitin, agar, agarose). A natural polymer can be isolated from a biologically source or it can be synthetic. A synthetic polymer is formulated or manufactured by a chemical process "by man" and is not created by a naturally occurring biological process. A non-natural polymer is a synthetic polymer that is not made from naturally occurring (animal or plant) materials or monomers (such as: amino acids, nucleotides, and saccharides). A polymer may be fully or partially natural, synthetic, or non-natural.

A polymer may have one or more labile, or cleavable, bonds. If the labile bonds are cleavable in physiological conditions or cellular physiological conditions, the polymer is biodegradable. The cleavable bond may either be in the mainchain or in a side chain. If the cleavable bond occurs in the main chain, then cleavage of the bond results in a decrease in polymer length and the formation of two or more molecules. For example, smaller polyvinylether polymers can be joined via labile bonds to form large polyvinylether polymers. If the cleavable bond occurs in the side chain, then cleavage of the bond results in loss of side chain atoms from the polymer.

Disclosed herein is a class of amphipathic polyvinyl random copolymers. The polyvinyl copolymers may be synthesized from two, three, or more different monomers. Preferred monomers may be selected from the list comprising: charged vinyl ether, vinyl ether containing a protected ionic group, phthalimide-protected amine vinyl ether, acyl vinyl ether, alkyl vinyl ether, lower alkyl vinyl ether, higher alkyl vinyl ether, butyl vinyl ether, dodecyl vinyl ether, octadecyl vinyl ether, cholesterol vinyl ether, and other hydrocarbon-containing hydrophobic vinyl ethers.

A class of particularly useful polymers comprise: amine-containing polyvinylether random copolymers polymerized with three monomers: phthalimide monomers, small hydrophobic monomers, and large hydrophobic monomers. Deprotection of the phthalimide monomer yields an amine monomer. Small hydrophobic monomers comprise carbon-hydrogen chains with two to six carbon atoms. Large hydrophobic monomers comprise carbon-hydrogen chains with about ten to about 22 carbon atoms, or about 12 to about 18 carbon atoms. Medium hydrophobic monomers comprise carbon-hydrogen chains with about 6 to about 10 carbon atoms. Preferred amino polyvinylether polymers comprise: amino/butyl/octadecyl polyvinylether or amino/butyl/dodecyl polyvinylether.

The biophysical properties of the poly(vinylether) random copolymers are determined by the particular monomers chosen, the ratio at which they are incorporated into the polymer, and the size of the polymer. Different polymers can be made by altering the feed ratio of monomers in the polymerization reaction. While the incorporated ratio of monomers in a polymer can be the same as the feed ratio of monomers, the ratios can be different. Whether the monomers are incorporated at the feed ratio or at a different ratio, it is possible to alter the feed ratio of monomers to achieve a desired monomer incorporation ratio. A preferred amino polyvinylether is a water soluble membrane active amine/butyl/octadecyl or amine/butyl/dodecyl random tripolymer. It is possible to synthesize polymers with similar amine and hydrophobic monomer content from polyamines such as: polyethyleneimine, polylysine, polyvinylamine, and polyallylamine, or other polymers such as polyvinylalcohol through modification of the side chains of these polymers.

Preferred membrane active polymers of the invention are water soluble at 1 mg/ml or greater. Preferred membrane active polymers of the invention are surface active. Membrane active polymers of the invention are preferably in the size range of about 5 kDa to about 100 kDa, more preferably about 7.5 kDa to about 50 kDa, and more preferably about 10 kDa to about 30 kDa.

Masking Agent

Polymers capable of delivering a polynucleotide from outside a cell to the cytoplasm of a cell are frequently toxic or have poor bio-distribution in vivo. Therefore, it is necessary to mask properties of the polymers that cause the toxicity or poor bio-distribution. Because modifying the polymer to mask these properties can also inactivate the transfection activity or membrane activity of the polymer, masking agents are linked to the polymer via physiologically reversible linkages. Cleavage of the linkage restores the shielded or masked property of the polymer.

As used herein, a masking agent comprises a molecule which, when linked to a polymer, shields, inhibits or inactivates one or more properties (biophysical or biochemical characteristics) of the polymer. A masking agent can also add an activity or function to the polymer that the polymer did not have in the absence of the asking agent. Properties of polymers that may be masked include: membrane activity, endosomolytic activity, charge, effective charge, transfection activity, serum interaction, cell interaction, and toxicity. Masking agents can also inhibit or prevent aggregation of the polynucleotide-polymer conjugate in physiological conditions. Masking agents of the invention may be selected from the group consisting of: steric stabilizers, targeting groups, and charge modifiers. Multiple masking agents can be reversibly linked to a single polymer. To inactivate a property of a polymer, it may be necessary to link more than one masking agent to the polymer. A sufficient number of masking agents are linked to the polymer to achieve the desired level of inactivation. The desired level of modification of a polymer by attachment of masking agent(s) is readily determined using appropriate polymer activity assays. For example, if the polymer possesses membrane activity in a given assay, a sufficient level of masking agent is linked to the polymer to achieve the desired level of inhibition of membrane activity in that assay. A sufficient number of masking agent can be reversibly linked to the polymer to inhibit aggregation of the polymer in physiologically conditions. More than one species of masking agent may be used. For example, both steric stabilizers and targeting groups may be linked to a polymer. Steric stabilizers and targeting groups may or may not also function as charge modifiers. The masking agents of the invention are reversibly linked to the polymer. As used herein, a masking agent is reversibly linked to a polymer if reversal of the linkage results in restoration of the masked activity of the polymer. Masking agents are linked to the polymer through the formation of reversible covalent linkages with reactive groups on the polymer. Reactive groups may be selected from the groups comprising: amines, alcohols, thiols, hydrazides, aldehydes, carboxyls, etc. From one to all of the reactive groups or charged groups on a polymer may be reversibly modified. In one embodiment, at least two masking agents are reversibly linked to the polymer. In another embodiment, masking agents are reversibly linked to about 20%, 30%, 40%, 50%, 60%, 70%, or 80% of the reactive groups on the polymer. In another embodiment, masking agents are reversibly linked to about 20%, 30%, 40%, 50%, 60%, 70%, or 80% of the charged groups on the polymer. In another embodiment, the percentage of masking agents reversibly linked the polymer to charged groups on the polymer is about 20%, 30%, 40%, 50%, 60%, 70%, or 80%.

As used herein, a polymer is masked if one or more properties of the polymer is inhibited or inactivated by attachment of one or more masking agents. A polymer is reversibly masked if cleavage of bonds linking the masking agents to the polymer results in restoration of the polymer's masked property.

Preferred masking agents of the invention are able to modify the polymer (form a reversible bond with the polymer) in aqueous solution. Of particular utility is a maleic anhydride derivative in which $R^1$ is methyl (—$CH_3$) and $R^2$ is a propionic acid group (—$(CH_2)_2CO_2H$) or esters/amides derived from the acid.

As used herein, a steric stabilizer is a natural, synthetic, or non-natural non-ionic hydrophilic polymer that prevents intramolecular or intermolecular interactions of polymer to which it is attached relative to the polymer containing no steric stabilizer. A steric stabilizer hinders a polymer from engaging in electrostatic interactions. Electrostatic interactions are the non-covalent association of two or more substances due to attractive forces between positive and negative charges. Steric stabilizers can inhibit interaction with blood components and therefore opsonization, phagocytosis and uptake by the reticuloendothelial system. Steric stabilizers can thus increase circulation time of molecules to which they are attached. Steric stabilizers can also inhibit aggregation of a polymer. Preferred steric stabilizers are polyethylene glycol (PEG) and PEG derivatives. As used herein, a preferred PEG can have about 1-500 ethylene glycol monomers, 2-20 ethylene glycol monomers, 5-15 ethylene glycol monomers, or about 10 ethylene glycol monomers. As used herein, a preferred PEG can also have a molecular weight average of about 85-20,000 Daltons (Da), about 200-1000 Da, about 200-750 Da, or about 550 Da. Other suitable steric stabilizers may be selected from the group comprising: polysaccharides, dextran, cyclodextrin, poly(vinyl alcohol), polyvinylpyrrolidone, 2-hydroxypropyl methacrylate (HPMA), and water soluble cellulose ether.

Targeting groups, or ligands, are used for targeting or delivery a polymer to target cells or tissues, or specific cells types. Targeting groups enhance the association of molecules with a target cell. Thus, targeting groups can enhance the pharmacokinetic or biodistribution properties of a conjugate to which they are attached to improve cellular distribution and cellular uptake of the conjugate. One or more targeting groups can be linked to the membrane active polymer either directly or via a linkage with a spacer. Binding of a targeting group, such as a ligand, to a cell or cell receptor may initiate endocytosis. Targeting groups may be monovalent, divalent, trivalent, tetravalent, or have higher valency. Targeting groups may be selected from the group comprising: compounds with affinity to cell surface molecule, cell receptor ligands, and antibodies, antibody fragments, and antibody mimics with affinity to cell surface molecules. A preferred targeting group comprises a cell receptor ligand. A variety of ligands have been used to target drugs and genes to cells and to specific cellular receptors. Cell receptor ligands may be selected from the group comprising: carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin). Examples of targeting groups include those that target the asialoglycoprotein receptor by using asialoglycoproteins or galactose residues. For example, liver hepatocytes contain ASGP Receptors. Therefore, galactose-containing targeting groups may be used to target hepatocytes. Galactose containing targeting groups include, but are not limited to: galactose, N-acetylgalactosamine, oligosaccharides, and saccharide clusters (such as: Tyr-Glu-Glu-(aminohexyl GalNAc)$_3$, lysine-based galactose clusters, and cholane-based galactose clusters). Further suitable conjugates can include oligosaccharides that can bind to carbohydrate recognition domains (CRD) found on the asialoglycoprotein-receptor (ASGP-R). Example conjugate moieties containing oligosaccharides and/or carbohydrate complexes are provided in U.S. Pat. No. 6,525,031

As used herein, a charge modifier is a group that alters the charge of an ionic group on a polymer. The charge modifier can neutralize a charged group on a polymer or reverse the charge, from positive to negative or negative to positive, of a polymer ion. Charge modification of a polyion can reduce the charge of the polyion, form a polyion of opposite charge, or form a polyampholyte. Charge modification can also be used to form a polymer with a desired net charge or zeta potential. Conjugates with near neutral net charge or zeta potential are preferred for in vivo delivery of polynucleotides. A preferred charge modifier reversibly modifies a charged, or ionic, group. Reversible charge modifiers may be selected from the group comprising: CDM, DM, CDM-thioester, CDM-masking agent, CDM-steric stabilizer, CDM-ligand, CDM-PEG, and CDM-galactose.

Zeta potential is a physical property which is exhibited by any particle in suspension and is closely related to surface charge. In aqueous media, the pH of the sample is one of the most important factors that affects zeta potential. When charge is based upon protonated/deprotonation of bases/acids, the charge is dependent on pH. Therefore, a zeta potential value must include the solution conditions, especially pH, to be meaningful. For typical particles, the magnitude of the zeta potential gives an indication of the potential stability of the colloidal system. If all the particles in suspension have a large negative or positive zeta potential then they will tend to repel each other and there will be no tendency for the particles to come together. However, if the particles have low zeta potential values then there will be no force to prevent the particles coming together and flocculating. The general dividing line between stable and unstable suspensions for typical particles is generally taken at either +30 or −30 mV. Particles with zeta potentials more positive than +30 mV or more negative than −30 mV are normally considered stable. We show here, that CDM-masked polynucleotide-polymer conjugates can form small particles, <20 nm or <10 nm (as measured by dynamic light scattering, analytic ultracentrifugation, or atomic force microscopy), that are stable despite having a zeta potential between +30 and −30 mV at physiological salt and pH 9.

Net charge, or zeta potential of the polynucleotide-polymer conjugates of the invention, can be controlled by the attachment of masking agents or charge modifiers. Polymer charge, especially positive charge, can result in unwanted interactions with serum components or non-target cells. By shielding charge with steric stabilizers or modification of charge, conjugates can be readily made with an apparent surface charge near neutral. By modifying charged groups on the polymer, serum stable particles can be made in which the zeta potential, measured at pH 9, is between +30 and −30 mV, between +20 and −20 mV, between +10 and −10 mV, or between +5 and −5 mV. At pH 7, the net charge of the conjugate would be expected to be more positive than at pH 9. Net charge, or surface charge, is a significant factor in delivery of polynucleotide complexes in vivo.

Labile Linkage

A linkage or linker is a connection between two atoms that links one chemical group or segment of interest to another chemical group or segment of interest via one or more covalent bonds. For example, a linkage can connect a polynucleotide or masking agent to a polymer. Formation of a linkage may connect two separate molecules into a single molecule or it may connect two atoms in the same molecule. The linkage may be charge neutral, or may bear a positive or negative charge. A reversible or labile linkage contains a reversible or labile bond. A linkage may optionally include a spacer that increases the distance between the two joined atoms. A spacer may further add flexibility and/or length to the linkage. Spacers may include, but are not be limited to: alkyl groups, alkenyl groups, alkynyl groups, aryl groups, aralkyl groups, aralkenyl groups, aralkynyl groups, each of which can contain one or more heteroatoms, and heterocycles. Spacer groups are well known in the art and the preceding list is not meant to limit the scope of the invention.

A reversible or labile bond is a covalent bond other than a covalent bond to a hydrogen atom that is capable of being selectively broken or cleaved under conditions that will not break or cleave other covalent bonds in the same molecule. More specifically, a reversible or labile bond is a covalent bond that is less stable (thermodynamically) or more rapidly broken (kinetically) under appropriate conditions than other non-labile covalent bonds in the same molecule. Cleavage of a labile bond within a molecule may result in the formation of two or more molecules. For those skilled in the art, cleavage or lability of a bond is generally discussed in terms of half-life ($t_{1/2}$) of bond cleavage, or the time required for half of the bonds to cleave. Orthogonal bonds are bonds that cleave under conditions that cleave one and not the other. Two bonds are considered orthogonal if their half-lives of cleavage in a defined environment are 10-fold or more different from one another. Thus, reversible or labile bonds encompass bonds that can be selectively cleaved more rapidly than other bonds a molecule.

The presence of electron donating or withdrawing groups can be located in a molecule sufficiently near the cleavable bond such that the electronic effects of the electron donating or withdrawing groups influence the rate of bond cleavage. Electron withdrawing groups (EWG) are atoms or parts of molecules that withdraw electron density from another atom, bond, or part of the molecule wherein there is a decrease in electron density to the bond of interest (donor). Electron donating groups (EDG) are atoms or parts of molecules that donate electrons to another atom, bond, or part of the molecule wherein there is an increased electron density to the bond of interest (acceptor). The electron withdrawing/donating groups need to be in close enough proximity to effect influence, which is typically within about 3 bonds of the bond being broken.

Another strategy for increasing the rate of bond cleavage is to incorporate functional groups into the same molecule as the labile bond. The proximity of functional groups to one another within a molecule can be such that intramolecular reaction is favored relative to an intermolecular reaction. The proximity of functional groups to one another within the molecule can in effect result in locally higher concentrations of the functional groups. In general, intramolecular reactions are much more rapid than intermolecular reactions. Reactive groups separated by 5 and 6 atoms can form particularly labile bonds due to the formation of 5 and 6-membered ring transition states. Examples include having carboxylic acid derivatives (acids, esters, amides) and alcohols, thiols, carboxylic acids or amines in the same molecule reacting together to make esters, carboxylic and carbonate esters, phosphate esters, thiol esters, acid anhydrides or amides. Steric interactions can also change the cleavage rate for a bond.

Appropriate conditions are determined by the type of labile bond and are well known in organic chemistry. A labile bond can be sensitive to pH, oxidative or reductive conditions or agents, temperature, salt concentration, the presence of an enzyme, or the presence of an added agent. For example, certain peptide, ester, or saccharide linkers may be cleaved in the presence of the appropriate enzyme. In another example, increased or decreased pH may be the appropriate conditions for a pH-labile bond. In yet another example, oxidative conditions may be the appropriated conditions for an oxidatively labile bond. In yet another example, reductive conditions may be the appropriate conditions for a reductively labile bond. For instance, a disulfide constructed from two alkyl thiols is capable of being broken by reduction in the presence of thiols, without cleavage of carbon-carbon bonds. In this example, the carbon-carbon bonds are non-labile to the reducing conditions.

The rate at which a labile group will undergo transformation can be controlled by altering the chemical constituents of the molecule containing the labile group. For example, addition of particular chemical moieties (e.g., electron acceptors or donors) near the labile group can affect the particular conditions (e.g., pH) under which chemical transformation will occur.

Molecules can contain one or more reversible or labile bonds. If more than one reversible or labile bond is present in the molecule, and all of the reversible or labile bonds are of the same type (cleaved at about the same rate under the same conditions), then the molecule contains multiple reversible or labile bonds. If more than one reversible or labile bond is present in the molecule, and the reversible or labile bonds are of different types (based either on the appropriate conditions for lability, or the chemical functional group of the labile bonds), then the molecule contains orthogonal reversible or labile bonds. Orthogonal reversible or labile bonds provides for the ability to cleave one type of reversible or labile bond while leaving a second type of reversible bond not cleaved or broken. In other words, two labile bonds are orthogonal to each other if one can be cleaved under conditions that leave the other intact. Orthogonal protecting groups are well known in organic chemistry and comprise orthogonal bonds.

As used herein, a physiologically labile bond is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. A cellular physiologically labile bond may also be cleaved in response to administration of a pharmaceutically acceptable exogenous agent. Physiologically labile bonds that are cleaved with a half life of less than 45 min. are considered very labile. Physiologically labile bonds that are cleaved with a half life of less than 15 min are considered extremely labile.

Chemical transformation (cleavage of the labile bond) may be initiated by the addition of a pharmaceutically acceptable agent to the cell or may occur spontaneously when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond.

pH-labile bond: As used herein, a pH-labile bonds is a labile bond that is selectively broken under acidic conditions (pH<7). Such bonds may also be termed endosomally labile bonds, since cell endosomes and lysosomes have a pH less than 7. The term pH-labile includes bonds that are pH-labile, very pH-labile, and extremely pH-labile. pH labile bonds may be selected from the group comprising:
a) ketals that are labile in acidic environments (pH less than 7, greater than 4) to form a diol and a ketone,
b) acetals that are labile in acidic environments (pH less than 7, greater than 4) to form a diol and an aldehyde,
c) imines or iminiums that are labile in acidic environments (pH less than 7, greater than 4) to form an amine and an aldehyde or a ketone,
d) silicon-oxygen-carbon linkages that are labile under acidic conditions,
e) silicon-nitrogen (silazanes) linkages, and
f) silicon-carbon linkages (arylsilanes, vinylsilanes, and allylsilanes).
g) maleamates-amide bonds synthesized from maleic anhydride derivatives and amines
h) ortho esters
i) hydrazones
j) activated carboxylic acid derivatives (esters, amides) designed to undergo acid catalyzed hydrolysis.
k) vinyl ethers Organosilanes have long been utilized as oxygen protecting groups in organic synthesis due to both the ease in preparation (of the silicon-oxygen-carbon linkage) and the facile removal of the protecting group under acidic conditions. For example, silyl ethers and silylenolethers, both posses such a linkage. Silicon-oxygen-carbon linkages are susceptible to hydrolysis under acidic conditions forming silanols and an alcohol (or enol). The substitution on both the silicon atom and the alcohol carbon can affect the rate of hydrolysis due to steric and electronic effects. This allows for the possibility of tuning the rate of hydrolysis of the silicon-oxygen-carbon linkage by changing the substitution on either the organosilane, the alcohol, or both the organosilane and alcohol to facilitate the desired affect. In addition, charged or reactive groups, such as amines or carboxylate, may be linked to the silicon atom, which confers the labile compound with charge and/or reactivity.

Hydrolysis of a silazane leads to the formation of a silanol and an amine. Silazanes are inherently more susceptible to hydrolysis than is the silicon-oxygen-carbon linkage, however, the rate of hydrolysis is increased under acidic conditions. The substitution on both the silicon atom and the amine can affect the rate of hydrolysis due to steric and electronic effects. This allows for the possibility of tuning the rate of hydrolysis of the silazane by changing the substitution on either the silicon or the amine to facilitate the desired affect.

Another example of a pH labile bond is the use of the acid labile enol ether bond. The rate at which this labile bond is cleaved depends on the structures of the carbonyl compound formed and the alcohol released. For example analogs of ethyl isopropenyl ether, which may be synthesized from β-haloethers, have half-lives of roughly 2 min at pH 5. Analogs of ethyl cyclohexenyl ether, which may be synthesized from phenol ethers, have half-lives of roughly 14 min at pH 5.

Reaction of an anhydride with an amine forms an amide and an acid. Typically, the reverse reaction (formation of an anhydride and amine) is very slow and energetically unfavorable. However, if the anhydride is a cyclic anhydride, reaction with an amine yields a molecule in which the amide and the acid are in the same molecule, an amide acid. The presence of both reactive groups (the amide and the carboxylic acid) in the same molecule accelerates the reverse reaction. In particular, the product of primary amines with maleic anhydride and maleic anhydride derivatives, maleamic acids, revert back to amine and anhydride $1\times10^9$ to $1\times10^{13}$ times faster than its noncyclic analogues (Kirby 1980).

Reaction of an Amine with an Anhydride to Form an Amide and an Acid

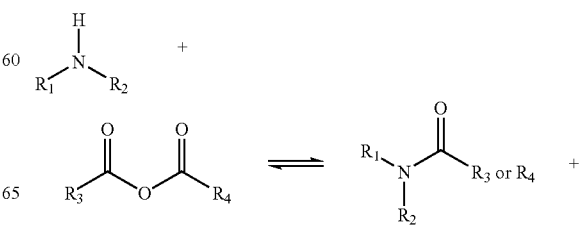

-continued

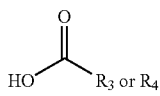

Reaction of an Amine with a Cyclic Anhydride to Form an Amide Acid

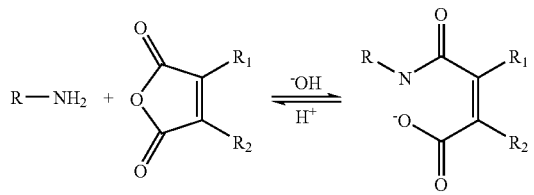

Cleavage of the amide acid to form an amine and an anhydride is pH-dependent, and is greatly accelerated at acidic pH. This pH-dependent reactivity can be exploited to form reversible pH-sensitive bonds and linkers. Cis-aconitic acid has been used as such a pH-sensitive linker molecule. The γ-carboxylate is first coupled to a molecule. In a second step, either the α or β carboxylate is coupled to a second molecule to form a pH-sensitive coupling of the two molecules. The half life for cleavage of this linker at pH 5 is between 8 and 24 h.

Structures of Cis-Aconitic Anhydride and Maleic Anhydride

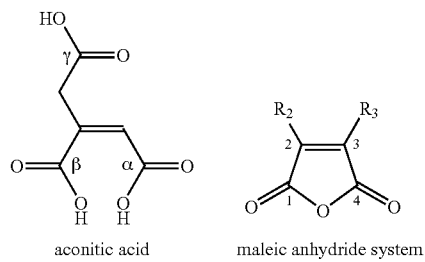

aconitic acid      maleic anhydride system

The pH at which cleavage occurs is controlled by the addition of chemical constituents to the labile moiety. The rate of conversion of maleamic acids to amines and maleic anhydrides is strongly dependent on substitution ($R^2$ and $R^3$) of the maleic anhydride system. When $R^2$ is methyl, the rate of conversion is 50-fold higher than when $R^2$ and $R^3$ are hydrogen. When there are alkyl substitutions at both $R^2$ and $R^3$ (e.g., 2,3-dimethylmaleicanhydride) the rate increase is dramatic, 10,000-fold faster than non-substituted maleic anhydride. The maleamate bond formed from the modification of an amine with 2,3-dimethylmaleic anhydride is cleaved to restore the anhydride and amine with a half-life between 4 and 10 min at pH 5. It is anticipated that if $R^2$ and $R^3$ are groups larger than hydrogen, the rate of amide-acid conversion to amine and anhydride will be faster than if $R^2$ and/or $R^3$ are hydrogen.

Very pH-labile bond: A very pH-labile bond has a half-life for cleavage at pH 5 of less than 45 min. The construction of very pH-labile bonds is well-known in the chemical art.

Extremely pH-labile bonds: An extremely pH-labile bond has a half-life for cleavage at pH 5 of less than 15 min. The construction of extremely pH-labile bonds is well-known in the chemical art.

Linkage of Polynucleotide to Polymer

Most previous methods for delivery of polynucleotide to cells have relied upon complexation of the anionic nucleic acid with a cationic delivery agent such as a cationic polymer or cationic lipid. Electrostatic complexes with larger polynucleotides, e.g. plasmids, tend to aggregate and become large, >500 nm, in physiological solutions. Smaller polynucleotides, oligonucleotides, because of their small size, form unstable electrostatic complexes with potential delivery agents. A more effective method for packaging polynucleotides is to covalently link the polynucleotide to the delivery vehicle. However, attachment to the polymer can inhibit the activity of the polynucleotide in the cell. We have found that by attaching the polynucleotide to the polymer via a reversible linker that is broken after the polynucleotide is delivered to the cell, it is possible to delivery a functionally active polynucleotide to a cell in vivo. The reversible linker is selected such that it undergoes a chemical transformation (e.g., cleavage) when present in certain physiological conditions, (e.g., the reducing environment of the cell cytoplasm). Attachment of a polynucleotide to a delivery or membrane active polymer enhances delivery of the polynucleotide to a cell in vivo. Release of the polynucleotide from the polymer, by cleavage of the reversible bond, facilitates interaction of the polynucleotide with the appropriate cellular components for activity.

In addition to polynucleotides, delivery of other membrane impermeable molecules or molecules with low membrane permeability can be delivered to cells in vivo using the described polyconjugate delivery vehicles. Molecules suitable for reversible attachment to a membrane active polymer include: proteins, antibodies, antibody fragments, transcription factors, small molecule drugs, anticancer drugs, and other synthetic molecules including those that affect transcription.

Attachment of the membrane impermeable molecule to a membrane active polymer enables the formation of an appropriately sized in vivo delivery vehicle. The described molecular conjugates are essentially polymeric and have similar size and targeting propertied as that observed for other polymers. For intravascular (system) delivery the vehicle needs to be able to cross the endothelial barrier in order reach parenchymal cells of interest. The largest endothelia fenestrae (holes in the endothelial barrier) occur in the liver and have an average diameter of about 100 nm. The trans-epithelial pores in other organs are much smaller. For example, muscle endothelium can be described as a structure which has a large number of small pores with a radius of 4 nm, and a low number of large pores with a radius of 20-30 nm. The size of the polynucleotide delivery vehicle is also important for the cellular uptake process. Cellular internalization through endocytosis is thought to be limited to complexes of about 100 nm in diameter, the size of endocytic vesicles. The described conjugates are less than 100 nm, more preferably less than 50 nM, and more preferably less than 20 nM or less than 10 nm.

Renal ultrafiltration is one of the main routes of elimination of hydrophilic proteins, polymers and polymer-protein conjugates from blood. Among the parameters affecting this process are chemical composition, size, charge. Globular proteins larger than about 70 kDa are largely excluded from clearance by renal ultrafiltration. Conjugation of steric stabilizers such as PEG, therefore, decreases renal clearance by increasing the effective molecular size of polymers to which they are attached. Ultrafiltration of PEGs with molecular weight lower than 8 kDa is not restricted, while ultrafiltration of PEGs in the range of 8-30 kDa is governed by the molecular size. With molecular weight exceeding 30 kDa, PEG elimination is dramatically decreased. For this reason, masked polymer-polynucleotide conjugates in which the overall size is larger than about 10 kDa, larger than about 20 kDa, or larger than about 30 kDa are preferred. In addition to decreasing kidney ultrafiltration, an increase molecule weight of a polymer can promote accumulation into permeable tissues, such as tumors, by the passive enhanced permeation and retention mechanism.

Polynucleotide

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

DNA may be in form of cDNA, in vitro polymerized DNA, plasmid DNA, parts of a plasmid DNA, genetic material derived from a virus, linear DNA, vectors (P1, PAC, BAC, YAC, and artificial chromosomes), expression vectors, expression cassettes, chimeric sequences, recombinant DNA, chromosomal DNA, an oligonucleotide, anti-sense DNA, or derivatives of these groups. RNA may be in the form of messenger RNA (mRNA), in vitro polymerized RNA, recombinant RNA, oligonucleotide RNA, transfer RNA (tRNA), small nuclear RNA (snRNA), ribosomal RNA (rRNA), chimeric sequences, anti-sense RNA, interfering RNA, small interfering RNA (siRNA), microRNA (miRNA), ribozymes, external guide sequences, small non-messenger RNAs (snmRNA), untranslatedRNA (utRNA), snoRNAs (24-mers, modified snmRNA that act by an anti-sense mechanism), tiny non-coding RNAs (tncRNAs), small hairpin RNA (shRNA), or derivatives of these groups. In addition, DNA and RNA may be single, double, triple, or quadruple stranded. Double, triple, and quadruple stranded polynucleotide may contain both RNA and DNA or other combinations of natural and/or synthetic nucleic acids.

A blocking polynucleotide is a polynucleotide that interferes with the function or expression of DNA or RNA. Blocking polynucleotides are not translated into protein but their presence or expression in a cell alters the expression or function of cellular genes or RNA. Blocking polynucleotides cause the degradation of or inhibit the function or translation of a specific cellular RNA, usually an mRNA, in a sequence-specific manner. Inhibition of an RNA can thus effectively inhibit expression of a gene from which the RNA is transcribed. As used herein, a blocking polynucleotide may be selected from the list comprising: anti-sense oligonucleotide, RNA interference polynucleotide, dsRNA, siRNA, miRNA, hRNA, ribozyme, hammerhead ribozyme, external guide sequence (U.S. Pat. No. 5,962,426), snoRNA, triple-helix forming oligonucleotide RNA Polymerase II transcribed DNA encoding a blocking polynucleotide, RNA Polymerase III transcribed DNAs encoding a blocking polynucleotide. Blocking polynucleotide can be DNA, RNA, combination of RNA and DNA, or may contain non-natural or synthetic nucleotides.

Blocking polynucleotides may be polymerized in vitro, they may be recombinant, contain chimeric sequences, or derivatives of these groups. A blocking polynucleotide may contain ribonucleotides, deoxyribonucleotides, synthetic nucleotides, or any suitable combination such that the target RNA or gene is inhibited.

An RNA interference (RNAi) polynucleotide is a molecule capable inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). However, other polynucleotides have been shown to mediate RNA interference. RNAi polynucleotides may be selected from the group comprising: siRNA, microRNA, double-strand RNA (dsRNA), short hairpin RNA (shRNA), and expression cassettes encoding RNA capable if inducing RNA interference. SiRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments, wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. MicroRNAs (miRNAs) are small noncoding RNA gene products about 22 nt long that direct destruction or translational repression of their mRNA targets. If the complementarity between the miRNA and the target mRNA is partial, then translation of the target mRNA is repressed, whereas if complementarity is extensive, the target mRNA is cleaved. For miRNAs, the complex binds to target sites usually located in the 3' UTR of mRNAs that typically share only partial homology with the miRNA. A "seed region"—a stretch of about 7 consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

Antisense oligonucleotide comprise a polynucleotide containing sequence that is complimentary to a sequence present in a target mRNA. The antisense oligonucleotide binds to (base pairs with) mRNA in a sequence specific manner. This binding can prevent other cellular enzymes from binding to the mRNA, thereby leading to inhibition of translation of the mRNA or degradation of the mRNA.

External guide sequences are short antisense oligoribonucleotides that induce RNase P-mediated cleavage of a target RNA by forming a precursor tRNA-like complex (U.S. Pat. No. 5,624,824).

Ribozymes are typically RNA oligonucleotides that contain sequence complementary to the target messenger RNA and an RNA sequence that acts as an enzyme to cleave the messenger RNA. Cleavage of the mRNA prevents translation.

An oligonucleotide that forms the blocking polynucleotide can include a terminal cap moiety at the 5'-end, the 3'-end, or both of the 5' and 3' ends. The cap moiety can be, but is not limited to, an inverted deoxy abasic moiety, an inverted deoxy thymidine moiety, a thymidine moiety, or 3' glyceryl modification.

RNA polymerase II and III transcribed DNAs can be transcribed in the cell to produce small hairpin RNAs that can function as siRNA, separate sense and anti-sense strand linear siRNAs, ribozymes, or linear RNAs that can function as antisense RNA. RNA polymerase III transcribed DNAs contain promoters selected from the list comprising: U6 promoters, III promoters, and tRNA promoters. RNA polymerase II promoters include U1, U2, U4, and U5 promoters, snRNA promoters, microRNA promoters, and mRNA promoters.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The polynucleotides of the invention can be chemically modified. The use of chemically modified polynucleotide can improve various properties of the polynucleotide including, but not limited to: resistance to nuclease degradation in vivo, cellular uptake, activity, and sequence-specific hybridization. Non-limiting examples of such chemical modifications include: phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various polynucleotide constructs, are shown to preserve polynucleotide activity in cells while at the same time, dramatically increasing the serum stability of these compounds. Chemically modified siRNA can also minimize the possibility of activating interferon activity in humans.

In one embodiment, the chemically-modified RNAi polynucleotide of the invention comprises a duplex having two strands, one or both of which can be chemically-modified, wherein each strand is about 19 to about 29 (e.g., about 19, 20, 21, 22, 23, 24, 25, 26, 27, 28, or 29) nucleotides. In one embodiment, an RNAi polynucleotide of the invention comprises one or more modified nucleotides while maintaining the ability to mediate RNAi inside a cell or reconstituted in vitro system. An RNAi polynucleotide can be modified wherein the chemical modification comprises one or more (e.g., about 1, 2, 3, 4, 5, 6, 7, 8, 9, 10, or more) of the nucleotides. An RNAi polynucleotide of the invention can comprise modified nucleotides as a percentage of the total number of nucleotides present in the RNAi polynucleotide. As such, an RNAi polynucleotide of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given RNAi polynucleotide depends on the total number of nucleotides present in the RNAi polynucleotide. If the RNAi polynucleotide is single stranded, the percent modification can be based upon the total number of nucleotides present in the single stranded RNAi polynucleotide. Likewise, if the RNAi polynucleotide is double stranded, the percent modification can be based upon the total number of nucleotides present in the sense strand, antisense strand, or both the sense and antisense strands. In addition, the actual percentage of modified nucleotides present in a given RNAi polynucleotide can also depend on the total number of purine and pyrimidine nucleotides present in the RNAi polynucleotide. For example, wherein all pyrimidine nucleotides and/or all purine nucleotides present in the RNAi polynucleotide are modified.

An RNAi polynucleotide modulates expression of RNA encoded by a gene. Because multiple genes can share some degree of sequence homology with each other, an RNAi polynucleotide can be designed to target a class of genes with sufficient sequence homology. Thus an RNAi polynucleotide can contain sequence that has complementarity to sequences that are shared amongst different gene targets or are unique for a specific gene target. Therefore the RNAi polynucleotide can be designed to target conserved regions of a RNA sequence having homology between several genes thereby targeting several genes in a gene families (e.g., different gene isoforms, splice variants, mutant genes etc.). In another embodiment, the RNAi polynucleotide can be designed to target a sequence that is unique to a specific RNA sequence of a single gene.

The term complementarity refers to the ability of a polynucleotide to form hydrogen bond(s) with another polynucleotide sequence by either traditional Watson-Crick or other non-traditional types. In reference to the polynucleotide molecules of the present invention, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases, in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene, or the level of polypeptide, protein or protein subunit translated from the RNA, is reduced below that observed in the absence of the blocking polynucleotide-conjugates of the invention. Inhibition, down-regulation, or knockdown of gene expression, with a polynucleotide delivered by the compositions of the invention, is preferably below that level observed in the presence of a control inactive nucleic acid, a nucleic acid with scrambled sequence or with inactivating mismatches, or in absence of conjugation of the polynucleotide to the masked polymer.

A delivered polynucleotide can stay within the cytoplasm or nucleus apart from the endogenous genetic material. Alternatively, DNA can recombine with (become a part of) the endogenous genetic material. Recombination can cause DNA to be inserted into chromosomal DNA by either homologous or non-homologous recombination.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell.

Polynucleotides may contain an expression cassette coded to express a whole or partial protein, or RNA. An expression cassette refers to a natural or recombinantly produced polynucleotide that is capable of expressing a sequence. The term recombinant as used herein refers to a polynucleotide molecule that is comprised of segments of polynucleotide joined together by means of molecular biological techniques. The cassette contains the coding region of the gene of interest along with any other sequences that affect expression of the sequence of interest. An expression cassette typically includes a promoter (allowing transcription initiation), and a transcribed sequence. Optionally, the expression cassette may include, but is not limited to: transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences.

The polynucleotide may contain sequences that do not serve a specific function in the target cell but are used in the generation of the polynucleotide. Such sequences include, but are not limited to, sequences required for replication or selection of the polynucleotide in a host organism.

The term gene generally refers to a polynucleotide sequence that comprises coding sequences necessary for the production of a therapeutic polynucleotide (e.g., ribozyme) or a polypeptide or precursor. The polypeptide can be encoded by a full length coding sequence or by any portion of the coding sequence so long as the desired activity or functional properties (e.g., enzymatic activity, ligand binding, signal transduction) of the full-length polypeptide or fragment are retained. The term also encompasses the coding region of a gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term gene encompasses both cDNA and genomic forms of a gene. A genomic form or clone of a gene contains the coding region interrupted with non-coding sequences termed introns, intervening regions or intervening sequences. Introns are segments of a gene which are transcribed into nuclear RNA. Introns may contain regulatory elements such as enhancers. Introns are removed or spliced out from the nuclear or primary transcript; introns therefore are absent in the mature RNA transcript. The messenger RNA (mRNA) functions during translation to specify the sequence or order of amino acids in a nascent polypeptide. A gene may also includes other regions or sequences including, but not limited to, promoters, enhancers, transcription factor binding sites, polyadenylation signals, internal ribosome entry sites, silencers, insulating sequences, matrix attachment regions. These sequences may be present close to the coding region of the gene (within 10,000 nucleotides) or at distant sites (more than 10,000 nucleotides). These non-coding sequences influence the level or rate of transcription and/or translation of the gene. Covalent modification of a gene may influence the rate of transcription (e.g., methylation of genomic DNA), the stability of mRNA (e.g., length of the 3' polyadenosine tail), rate of translation (e.g., 5' cap), nucleic acid repair, nuclear transport, and immunogenicity. One example of covalent modification of nucleic acid involves the action of LABELIT® reagents (Mirus Corporation, Madison, Wis.).

As used herein, the term gene expression refers to the process of converting genetic information encoded in a gene into RNA (e.g., small RNA, siRNA, mRNA, rRNA, tRNA, or snRNA) through transcription of a deoxyribonucleic gene (e.g., via the enzymatic action of an RNA polymerase), and for protein encoding genes, into protein through translation of mRNA. Gene expression can be regulated at many stages in the process. Up-regulation or activation refers to regulation that increases the production of gene expression products (i.e., RNA or protein), while down-regulation or repression refers to regulation that decrease production. Molecules (e.g., transcription factors) that are involved in up-regulation or down-regulation are often called activators and repressors, respectively.

The polynucleotide may be used for research purposes or to produce a change in a cell that can be therapeutic. The delivery of a polynucleotide for therapeutic purposes is commonly called gene therapy. The delivery of a polynucleotide can lead to modification of the genetic material present in the target cell. The term stable transfection or stably transfected generally refers to the introduction and integration of an exogenous polynucleotide into the genome of the transfected cell. The term stable transfectant refers to a cell which has stably integrated the polynucleotide into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of a polynucleotide into a cell where the polynucleotide does not integrate into the genome of the transfected cell. If the polynucleotide contains an expressible gene, then the expression cassette is subject to the regulatory controls that govern the expression of endogenous genes in the chromosomes. The term transient transfectant refers to a cell which has taken up a polynucleotide but has not integrated the polynucleotide into its genomic DNA.

Formulation

The polynucleotide-polymer conjugate is formed by covalently linking the polynucleotide to the polymer. The polymer is polymerized or modified such that it contains a reactive group A. The polynucleotide is also polymerized or modified such that it contains a reactive group B. Reactive groups A and B are chosen such that they can be linked via a reversible covalent linkage using methods known in the art.

Conjugation of the polynucleotide to the polymer can be performed in the presence of an excess of polymer. Because the polynucleotide and the polymer may be of opposite charge during conjugation, the presence of excess polymer can reduce or eliminate aggregation of the conjugate. Alternatively, an excess of a carrier polymer, such as a polycation, can be used. The excess polymer can be removed from the conjugated polymer prior to administration of the conjugate to the animal or cell culture. Alternatively, the excess polymer can be co-administered with the conjugate to the animal or cell culture.

Similarly, the polymer can be conjugated to the masking agent in the presence of an excess of polymer or masking agent. Because the polynucleotide and the polymer may be of opposite charge during conjugation, the presence of excess polymer can reduce or eliminate aggregation of the conjugate. Alternatively, an excess of a carrier polymer can be used. The excess polymer can be removed from the conjugated polymer prior to administration of the conjugate to the animal or cell culture. Alternatively, the excess polymer can be co-administered with the conjugate to the animal or cell culture. The polymer can be modified prior to or subsequent to conjugation of the polynucleotide to the polymer.

Transfection Reagent

The process of delivering a polynucleotide to a cell has been commonly termed transfection or the process of transfecting. The term transfecting as used herein refers to the introduction of a polynucleotide or other biologically active compound from outside a cell to inside cell such the polynucleotide has biologically activity. The polynucleotide may be used for research purposes or to produce a change in a cell that can be therapeutic. The delivery of a polynucleotide can lead to modification of the genetic material present in the target cell. A transfection reagent or delivery vehicle is a compound or compounds that bind(s) to or complex(es) with oligonucleotides and polynucleotides, and mediates their entry into cells.

In vitro transfection reagents, or delivery vehicles, are compounds or compositions of compounds that bind to or complex with oligonucleotides and polynucleotides and mediate their entry into cells. Examples of transfection reagents include, but are not limited to, protein and polymer complexes (polyplexes), lipids and liposomes (lipoplexes), combinations of polymers and lipids (lipopolyplexes), calcium phosphate precipitates, and dendrimers. Typically, the transfection reagent has a component with a net positive charge that binds to the oligonucleotide's or polynucleotide's negative charge. Cationic transfection agents may also condense large nucleic acids. Transfection agents may also be used to associate functional groups with a polynucleotide. Functional groups include cell targeting signals, nuclear localization signals, compounds that enhance release of contents from endosomes or other intracellular vesicles (such as membrane active compounds), and other compounds that alter the behavior or interactions of the compound or complex to which they are attached (interaction modifiers).

The conjugated polynucleotides of the instant invention provide useful reagents and methods for a variety of therapeutic, diagnostic, target validation, genomic discovery, genetic engineering and pharmacogenomic applications. The conjugated polynucleotide has improved cellular uptake properties compared with the same unconjugated polynucleotide.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical. An administration route involving the mucosal membranes is meant to include nasal, bronchial, inhalation into the lungs, or via the eyes. Intraparenchymal includes direct injection into a tissue such as liver, lung, heart, muscle (skeletal muscle or diaphragm), spleen, pancreas, brain (including intraventricular), spinal cord, ganglion, lymph nodes, adipose tissues, thyroid tissue, adrenal glands, kidneys, prostate, and tumors. Transdermal routes of administration have been affected by patches and iontophoresis. Other epithelial routes include oral, nasal, respiratory, rectum, and vaginal routes of administration.

The conjugates can be injected in a pharmaceutically acceptable carrier solution. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals, and more particularly in humans.

Therapeutic Effect

We have disclosed polynucleotide delivery, resulting in gene expression or inhibition of gene expression of reporter genes and endogenous genes in specific tissues. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease, for example: Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. Similarly inhibition of a gene need not be 100% to provide a therapeutic benefit. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes such as the genes for luciferase and β-galactosidase serve as useful paradigms for expression of intracellular proteins in general. Similarly, reporter or marker genes secreted alkaline phosphatase (SEAP) serve as useful paradigms for secreted proteins in general.

A therapeutic effect of the protein expressed from a delivered polynucleotide in attenuating or preventing a disease, condition, or symptom can be accomplished by the protein either staying within the cell, remaining attached to the cell in the membrane or being secreted and dissociating from the cell where it can enter the general circulation and blood. Secreted proteins that can be therapeutic include hormones, cytokines, growth factors, clotting factors, anti-protease proteins (e.g. alpha-antitrypsin) and other proteins that are present in the blood. Proteins on the membrane can have a therapeutic effect by providing a receptor for the cell to take up a protein or lipoprotein. For example, the low density lipoprotein (LDL) receptor could be expressed in hepatocytes and lower blood cholesterol levels and thereby prevent atherosclerotic lesions that can cause strokes or myocardial infarction. Therapeutic proteins that stay within the cell can be enzymes that clear a circulating toxic metabolite as in phenylketonuria. They can also cause a cancer cell to be less proliferative or cancerous (e.g. less metastatic). A protein within a cell could also interfere with the replication of a virus.

Liver is one of the most important target tissues for gene therapy given its central role in metabolism (e.g., lipoprotein metabolism in various hypercholesterolemias) and the secretion of circulating proteins (e.g., clotting factors in hemophilia). At least one hundred different genetic disorders could potentially be corrected by liver-directed gene therapy. In addition, acquired disorders such as chronic hepatitis and cirrhosis are common and could also be treated by polynucleotide-based liver therapies. Gene therapies involving heterotropic gene expression would further enlarge the number of disorders treatable by liver-directed gene transfer. For example, diabetes mellitus could be treated by expressing the insulin gene within hepatocytes whose physiology may enable glucose-regulated insulin secretion.

In addition to increasing or decreasing genes involved in metabolism or disease, delivery of polynucleotides to cell in vivo can also be used to stimulate the immune system, stimulate the immune system to destroy the cancer cells, inactive oncogenes, or activate or deliver tumor suppressor genes. Polynucleotides can also be delivered to induce immunity to pathogens or to block expression of pathogenic genes.

Miscellaneous Definitions

As used herein, in vivo means that which takes place inside an organism and more specifically to a process performed in or on the living tissue of a whole, living multicellular organism (animal), such as a mammal, as opposed to a partial or dead one.

As used herein, in vitro refers to a process performed in an artificial environment created outside a living multicellular organism (e.g., a test tube or culture plate) used in experimental research to study a disease or process. As used herein, in vitro includes processes performed in intact cells growing in culture.

As used herein, in situ refers to processes carried out in intact tissue. However, the tissue can be in a living organism or removed from the organism.

As used herein, ex vivo refers to a process performed in an artificial environment outside the organism on living cells or tissue which are removed from an organism and subsequently returned to an organism.

Crosslinkers are bifunctional molecules used to connect two molecules together, i.e. form a linkage between two molecules. Bifunctional molecules can contain homo or heterobifunctionality.

As used herein, a surface active polymer lowers the surface tension of water and/or the interfacial tension with other phases, and, accordingly, is positively adsorbed at the liquid/vapor interface.

An antibody is any immunoglobulin, including antibodies and fragments thereof, that binds a specific epitope. The term encompasses polyclonal, monoclonal, and chimeric antibodies. An antibody combining site is that structural portion of an antibody molecule comprised of heavy and light chain variable and hypervariable regions that specifically binds antigen. The phrase antibody molecule in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', F(ab').sub.2 and F(v), which portions are preferred for use in the therapeutic methods described herein. Fab and F(ab').sub.2 portions of antibody molecules are prepared by the proteolytic reaction of papain and pepsin, respectively, on substantially intact antibody molecules by methods that are well-known. The phrase monoclonal antibody in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

EXAMPLES

Example 1

Polynucleotide Synthesis and Assembly

The following synthetic RNA oligonucleotides (Dharmacon, Lafayette Colo.) were used. Sense strand RNAs contained a primary amine with a six carbon spacer at the 5' to allow conjugation to the delivery vehicle. The 2'ACE protected RNA oligonucleotides were deprotected prior to the annealing step according to the manufacturer's instructions. The siRNAs had the following sequences:

apoB (Ensembl# ENSMUST00000037520);
apoB-1 siRNA
sense    5'-NH$_4$-GAAmUGmUGGGmUGGmCAAmCmUmUmUmA*G,,    SEQ ID 1

-continued

```
antisense  5'-P-AmAAGUUGCCACCCACAUUCmA*G,;            SEQ ID 2 apoB-2 siRNA
sense      5'-NH4-GGAmCAmUGGGmUmUCCAAAmUmUAmC*G,,    SEQ ID 3 antisense  5'-P-UmAAUUUGGAACCCAUGUCCmC*G,;           SEQ ID 4 ppara (GenBank# NM_011144);
ppara-1 siRNA,
sense      5'-NH4-mUmCAmCGGAGmCmUmCAmCAGAAmUmUmC*U-3',,  SEQ ID 5 antisense  5'-P-AmAUUCUGUGAGCUCCGUGAmC*U-3',;        SEQ ID 6 ppara-2 siRNA
sense      5'-NH4-mUmCCCAAAGCmUCCmUmUmCAAAAmU*U-3',,  SEQ ID 7 antisense  5'-P-mUmUUUGAAGGAGCUUUGGGAmA*G-3',;       SEQ ID 8

Control siRNA (GL-3 luciferase reporter gene),
sense      5'-NH4-mCmUmUAmCGmCmUGAGmUAmCmUmUmCGAmU*U-3';, SEQ ID 9 antisense  5'-P-UmCGAAGUACUCAGCGUAAGmU*U;;           SEQ ID 10 m = 2'-O-CH3 substitution,
* = phosphorothioate linkage, and
P = PO4.
```

Sense and antisense oligonucleotides for each target sequence were annealed by mixing equimolar amounts of each and heating to 94° C. for 5 min, cooling to 90° C. for 3 min, then decreasing the temperature in 0.3° C. steps 250 times, holding at each step for 3 sec.

Example 2

Polyvinylether Random Copolymers

A. Synthesis of a vinyl ether monomer. 2-Vinyloxy Ethyl Phthalimide was prepared via reacting 2-chloroethyl vinyl ether (25 g, 0.24 mol) and potassium phthalimide (25 g, 0.135 mol) in 100° C. DMF (75 ml) using tetra n-butyl ammonium bromide (0.5 g) as the phase transfer catalyst. This solution was heated for 6 h and then crashed out in water and filtered. This solid was then recrystallized twice from methanol to give white crystals.

B. Amine+lower alkyl polyvinylether polymers. A series of copolymers was synthesized from vinylether monomers with varying alkyl to amine group ratios and with alkyl groups having from one to four carbons (FIG. 1, R and R' may be the same or different). Membrane activity was dependent on the size (alkyl chain length) and ratio of hydrophobic monomers (Wakefield 2005). Propyl and butyl-derived polymers were found to be membrane lytic using model liposomes while methyl and ethyl containing polymers were not. We termed these polymers methyl, ethyl, propyl, or butyl-aminovinyl ethers or (PMAVE, PEAVE, PPAVE, or PBAVE respectively). These polymers possess sufficient charge to complex with DNA in physiological concentrations of salt. In contrast, small membrane lytic cationic peptides such as melittin are too weak and cannot condense DNA in isotonic saline solutions. The larger size of the synthetic amphipathic polymers not only enhances their DNA binding ability, but also makes them more lytic on a molar basis than melittin. The ability to lyse membranes with less number of polymer molecules will facilitate in vivo nucleic acid delivery. Using fluorophore-labeled DNA, we determined the charge density of the synthesized polymers and confirmed their stability in saline.

C. Synthesis of water-soluble, amphipathic, membrane active polyvinylether polyamines terpolymers. $\underline{X}$ mol % amine-protected vinylether (e.g., 2-Vinyloxy Ethyl Phthalimide) was added to an oven dried round bottom flask under a blanket of nitrogen in anhydrous dichloromethane. To this solution $\underline{Y}$ mol % alkyl (e.g., ethyl, propyl, or butyl) vinylether was added, followed by $\underline{Z}$ mol % alkyl(dodecyl, octadecyl) vinylether (FIG. 1). While the polymers detailed are derived from 2-3 different monomers, the invention is not limited to a specific composition of vinyl ether monomers. Polymers comprising more monomers or different monomers were readily envisioned. The solution was brought to −78° C. in a dry ice acetone bath. To this solution 10 mol % $BF_3EtOEt$ was added and the reaction was allowed to proceed for 2-3 h at −78° C., and then quenched with a methanol ammonium hydroxide solution. The polymer was brought to dryness under reduced pressure and then brought up in 30 ml of 1,4-dioxane/methanol (2/1). 20 mol eq. of hydrazine per phthalimide was added to remove the protecting group from the amine. The solution was refluxed for 3 h, then brought to dryness under reduced pressure. The solid was brought up in 20 ml 0.5 $\underline{M}$ HCl, refluxed for 15 min, diluted with 20 ml distilled water, and refluxed for additional hour. The solution was then neutralized with NaOH, cooled to room temperature, transferred to 3,500 molecular cellulose tubing, dialyzed for 24 hrs (2×20 L) against distilled water, and freeze dried. The molecular weight of the polymers was estimated using analytical size exclusion columns according to standard procedures. While polymers containing the indicated vinyl ether monomers are described in these examples, the invention is not limited to these particular monomers.

After removal of the phthalimide groups by sequential treatment with hydrazine and HCl, the polymers were transfer to 3,500 molecular cellulose tubing and dialyzed for 24 h (2×20 L) against distilled water, and freeze dried. The polymers were then dissolved in water and placed onto a sephadex G-15 column. The polymers that were excluded from sephadex G-15 were isolated and concentrated by lyophilization. The molecular weights of the polymers were then determined by GPC using Eprogen Inc. CATSEC100, CATSEC300, and CATSEC1000 columns in series. The running buffer was 50 mM NaCl, 0.1% TFA, and 10% MeOH. Polyvinylpyridine standards were used as the calibration curve. The molecular weights of the polymers were in the range 10,000-100,000 Da, with the majority of polymer preparations over 20,000 Da.

D. Synthesis of DW1360. An amine/butyl/octadecyl polyvinylether terpolymer, was synthesized from 2-Vinyloxy Ethyl Phthalimide (3.27 g, 15 mmol), butyl vinylether (0.40 g, 4 mmol), and octadecylvinylether (0.29 g, 1 mmol) monomers. The monomers were dissolved in 30 ml anhydrous dichloromethane. These solutions were then added to a −78° C. dry ice/acetone bath. 2 min later, $BF_3.OEt_2$ (0.042 g, 0.3 mmol) was added and the reaction was allowed to proceed for 3 h at −78° C. The polymerization was then stopped by the addition of 50/50 mixture of ammonium hydroxide in methanol or a solution of lithium borohydride. The solvents were then removed by rotary evaporation. The polymer was then dissolved in 30 ml of 1,4-dioxane/methanol (2/1). To this solution was added hydrazine (0.44 g, 138 mmol) and the mixture was heated to reflux for 3 h. The solvents were then removed by rotary evaporation and the resulting solid was then brought up in 20 ml of 0.5 M HCl and refluxed for 15 min, diluted with 20 ml distilled water, and refluxed for additional hour. This solution was then neutralized with NaOH, cooled to RT, transferred to 3,500 molecular cellulose tubing, and dialyzed for 24 h (2×20 L) against distilled water, and lyophilized.

Similarly, other polymers containing various ratios of amine, butyl and octadecyl groups may be synthesized. Also other monomers may be incorporated. In particular, t-butyl vinyl ether, dodecyl vinylether, and oleic vinylether have been incorporated into polymers.

In one embodiment, the amine/lower alkyl/higher alkyl polyvinylether terpolymers can be synthesized using monomers at a feed ratio of 15 amine monomer:4 lower alkyl monomer:1 higher alkyl monomer. Under the conditions described above, the incorporation ratio was determined to be about 5.4-7.5 amine monomer:3-3.5 lower alkyl monomer:1 higher alkyl monomer. In another embodiment, the amine/lower alkyl/higher alkyl polyvinylether terpolymers are synthesized using monomers at a feed ratio of 4-8 amine monomer:3-5 lower alkyl monomer:1 higher alkyl monomer. In a preferred embodiment, the polymers are water soluble (about 1 mg/ml or greater at 25° C.) and surface active.

In one embodiment, the polymers are fractionated to yield polymers of molecule weight of about 5 kDa to about 50 kDa, and more preferably about 10 kDa to about 30 kDa.

E. Other terpolymers. Similar polymers can be synthesized of modification of different base polymers, including, but not limited to: poly-L-lysine (PLL), polyvinylamine (PVA), and polyallylamine (PAA). By attachment of alkyl groups to different the main chain of these polymers, terpolymers can by made with a ratio of amine:lower alkyl:higher alkyl of about 6:3:1.

F. Liposome lysis. 10 mg of egg phosphatidylcholine was hydrated with 1 ml of buffer containing 100 mM carboxyfluorescein (CF) and 10 mM HEPES pH 7.5. Liposomes were then be extruded through 100-nm pores polycarbonate filters (Nucleopore, Pleasanton, Calif.). Unentrapped CF was removed by size exclusion chromatography using Sepharose 4B-200 eluting with 10 mM HEPES pH 8.0.1 M NaCl. A 200 µL aliquot of the CF-loaded liposomes were added to 1.8 ml of isotonic buffer. Fluorescence ($\lambda_{ex}$=488, $\lambda_{em}$=540) was measured 30 min after addition of 0.25 µg of polymers or melittin to vesicle suspensions. At the end of each experiment, vesicles were disrupted by the addition of 40 µl of a 1% Triton X-100 solution to determine maximal lysis.

Example 3

Masking Agents

A. Synthesis of 2-propionic-3-methylmaleic anhydride (carboxydimethylmaleic anhydride or CDM). To a suspension of sodium hydride (0.58 g, 25 mmol) in 50 ml anhydrous tetrahydrofuran was added triethyl-2-phosphonopropionate (7.1 g, 30 mmol). After evolution of hydrogen gas had stopped, dimethyl-2-oxoglutarate (3.5 g, 20 mmol) in 10 ml anhydrous tetrahydrofuran was added and stirred for 30 min. Water, 10 ml, was then added and the tetrahydrofuran was removed by rotary evaporation. The resulting solid and water mixture was extracted with 3×50 ml ethyl ether. The ether extractions were combined, dried with magnesium sulfate, and concentrated to a light yellow oil. The oil was purified by silica gel chromatography elution with 2:1 ether:hexane to yield 4 g (82% yield) of pure triester. The 2-propionic-3-methylmaleic anhydride was then formed by dissolving of this triester into 50 ml of a 50/50 mixture of water and ethanol containing 4.5 g (5 equivalents) of potassium hydroxide. This solution was heated to reflux for 1 h. The ethanol was then removed by rotary evaporation and the solution was acidified to pH 2 with hydrochloric acid. This aqueous solution was then extracted with 200 ml ethyl acetate, which was isolated, dried with magnesium sulfate, and concentrated to a white solid. This solid was then recrystallized from dichloromethane and hexane to yield 2 g (80% yield) of 2-propionic-3-methylmaleic anhydride.

Thioesters, esters and amides may be synthesized from CDM by conversion of CDM to its acid chloride with oxalyl chloride followed by the addition of a thiol, ester or amine and pyridine. CDM and its derivatives are readily modified by methods standard in the art, to add targeting ligands, steric stabilizers, charged groups, and other reactive groups. The resultant molecules can be used to reversibly modify amines.

Figure 2:
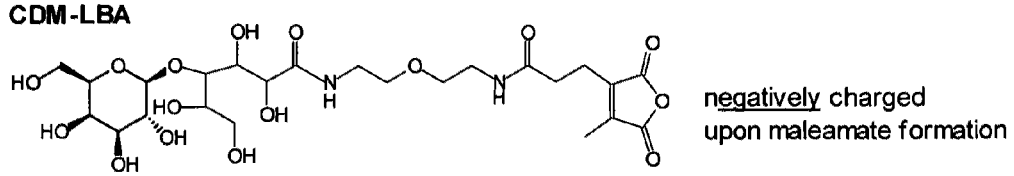
FIG. 2. Drawing illustrating several embodiments of masking agents of the invention.
Figure 2:
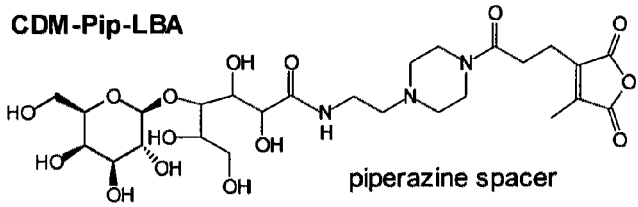
Figure 2:
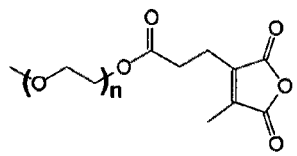
Figure 2:
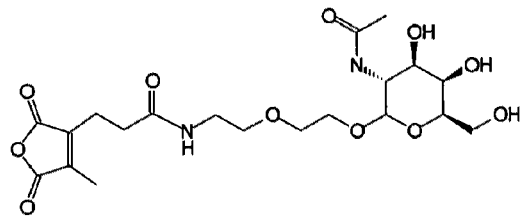

B. Galactose-containing targeting groups. The most widely-studied hepatocyte targeting ligands are based on galactose, which is bound by the asialoglycoprotein receptor (ASGPr) on hepatocytes. Attachment of galactose has been shown to facilitate hepatocyte targeting of a few highly water soluble, uncharged polymers, including: the oligosaccharide chitosan, a polystyrene derivative, and a polyacrylamide HPMA. Galactose targeting groups are readily generated using lactose, a galactose-glucose disaccharide, via modification of the glucose residue. Lactobionic acid (LBA, a lactose derivative in which the glucose has been oxidized to gluconic acid) is readily incorporated into a maleic anhydride derivative using standard amide coupling techniques. FIG. 2 shows the structure of two LBA derivatives that couple galactose to the maleic anhydride CDM.

Maleamate modification converts a positively-charged amine group into a negatively charged one. This charge modification can reduce non-specific interaction of the polymer with negatively charged cells and serum components. However, too much negative charge can enhance interaction with scavenger receptors. A net neutral galactose-containing maleic anhydride derivative can be generated by inserted a positively charged tertiary amine group into the masking agent, creating a zwitterion. Such a compound, CDM-Pip-LBA, was generated from the components: CDM, propylaminopiperazine, and lactobionic acid (FIG. 2).

C. Steric stabilizer CDM-PEG and targeting group CDM-NAG (N-acetyl galactosamine) syntheses (FIG. 2). To a solution of CDM (Rozema 2003) (300 mg, 0.16 mmol) in 50 ml methylene chloride was added oxalyl chloride (2 g, 10 wt. eq.) and dimethylformamide (5 µl). The reaction was allowed to proceed overnight at which time the excess oxalyl chloride and methylene chloride were removed by rotary evaporation to yield the CDM acid chloride. The acid chloride was dissolved in 1 ml of methylene chloride. To this solution was added 1.1 molar equivalents polyethylene glycol monomethyl ether (MW average 450) for CDM-PEG or (aminoethoxy)ethoxy-2-(acetylamino)-2-deoxy-β-D-glucopyranoside (i.e. amino bisethoxylethyl NAG) for CDM-NAG, and pyridine (200 µl, 1.5 eq) in 10 ml of methylene chloride. The solution was then stirred 1.5 h. The solvent was then removed and the resulting solid was dissolved into 5 ml of water and purified using reverse-phase HPLC using a 0.1% TFA water/acetonitrile gradient (FIG. 2).

Example 4

Reversible Attachment of Polynucleotide to Polymer

Modification of amino siRNA oligos with S-acetyl groups resulted in stable protected thiols that could be released in a basic solution (pH≧9) in the presence of an amine-containing polycation. Standard deprotection conditions for removal of a thioester group require incubation with hydroxylamine. However, these deprotection conditions result in significant siRNA disulfide dimer formation. Typically, the reaction between an alkyl amine and thioester is relatively slow, but in a complex between polyanionic siRNA and a polycationic amine, the reaction between functional groups became essentially intramolecular and was greatly accelerated (see Step 2a in FIG. 3). In addition to accelerating the deprotection, the released thiol's reaction with activated disulfide groups on the polycation was greatly enhanced (Step 2b). The activated disulfide pyridyldithiol (PD) insured selective disulfide formation, and was easily attached to the polycation using commercially available reagents. The result of these intra-particle reactions was >90% conjugation of disulfide to polycation.

Example 5

Reversible Conjugation of Polynucleotide to Polymer

A. SATA modified polynucleotide. N-succinimidyl-5-acetylthioacetate (SATA)-modified polynucleotides were synthesized by reaction of 5' amine-modified siRNA with 1 weight equivalents (wt. eq.) of SATA reagent (Pierce) and 0.36 wt. eq. of NaHCO$_3$ in water at 4° C. for 16 h. The protected thiol modified siRNAs were precipitated by the addition of 9 volumes of ethanol and incubation at −78° C. for 2 h. The precipitate was isolated, dissolved in 1×siRNA buffer (Dharmacon), and quantitated by measuring absorbance at the 260 nm wavelength.

Polymer, in this example PBAVE or DW1360 (30 mg/ml in 5 mM TAPS pH 9), was modified by addition of 1.5 wt % 4-succinimidyloxycarbonyl-α-methyl-α-[2-pyridyldithio]-toluene (SMPT, Pierce). 1 h after addition of SMPT, 0.8 mg of SMPT-polymer was added to 400 µl isotonic glucose solution containing 5 mM TAPS pH 9. To this solution was added 50 µg of SATA-modified siRNA. For the dose response experiments where PBAVE concentration was constant, different amounts of siRNA were added. The mixture was then incubated for 16 h. In this way, the polynucleotide was conjugated to the polymer via a reversible disulfide bone. A disulfide bond for conjugation between the polymer and siRNA provides for reversibility in the reducing environment of the cytoplasm. The siRNA-polymer conjugate was masked by adding to the solution 5.6 mg of HEPES free base followed by a mixture of 3.7 mg CDM-NAG and 1.9 mg CDM-PEG. The solution was then incubated 1 h at room temperature (RT) before injection.

B. Quantitation of conjugated polynucleotide. To quantify the amount of conjugated siRNA, 10 µl aliquots of siRNA-polymer conjugate containing 1 µg siRNA were treated with 2 µl of 1 M DTT or with no additive at RT for 16 h. 100 µg polyacrylic acid and 300 µg NaCl were added to the samples to neutralize electrostatic interactions. After a 2 h incubation, the samples were electrophoresed on a 2% agarose gel and the siRNA visualized by staining with ethidium bromide. The siRNA bands were quantified using Kodak Molecular Imaging Software v4.0. The amount of siRNA unconjugated was normalized to the amount released upon DTT treatment to determine percent conjugated. The amount of conjugated siRNA was typically 70-90%.

Other disulfide conjugation chemistry may be used wherein the thiol is protected as a disulfide or not protected at all. Additionally, the polymer may be modified with other activated disulfide groups, thiol groups, or protected thiol groups.

Example 6

Figure 3:
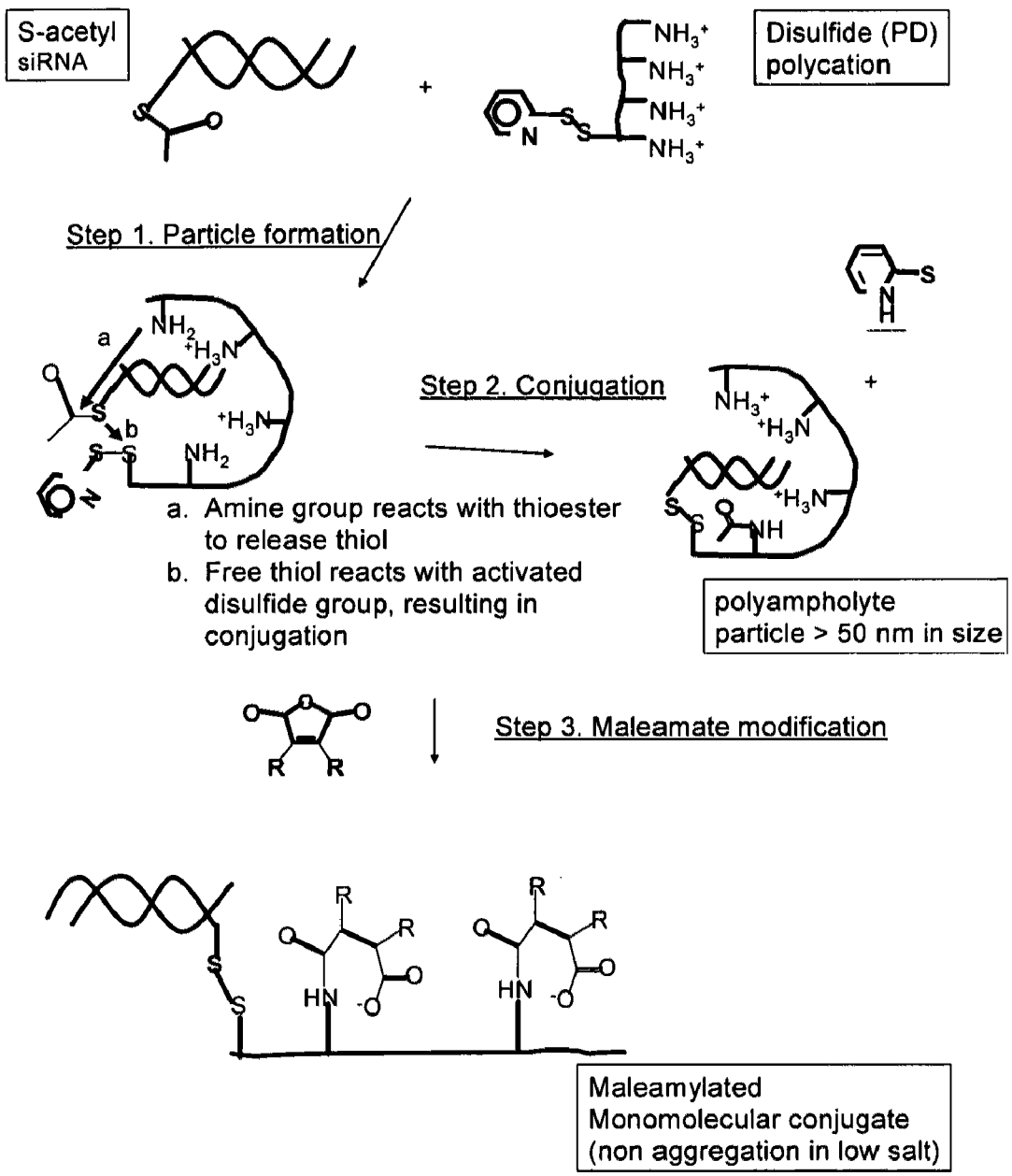
FIG. 3. Diagram illustrating polynucleotide-polymer reversible conjugates and reversible masking of the conjugate by maleamates.

Reversible Attachment of CDM-Masking Agents to Polynucleotide-Polymers Conjugates The polynucleotide-polymer conjugates may be modified, such as with maleic acid derivatives, to reversibly modify the polymer (FIG. 3, Step 4.). The siRNA-polymer conjugate was masked by adding to the solution 5.6 mg of HEPES free base followed by a mixture of 3.7 mg CDM-NAG and 1.9 mg CDM-PEG. The solution was then incubated 1 h at room temperature (RT) before in vivo injection.

Example 7

Targeting Activity of Masked Conjugates

Figure 4:
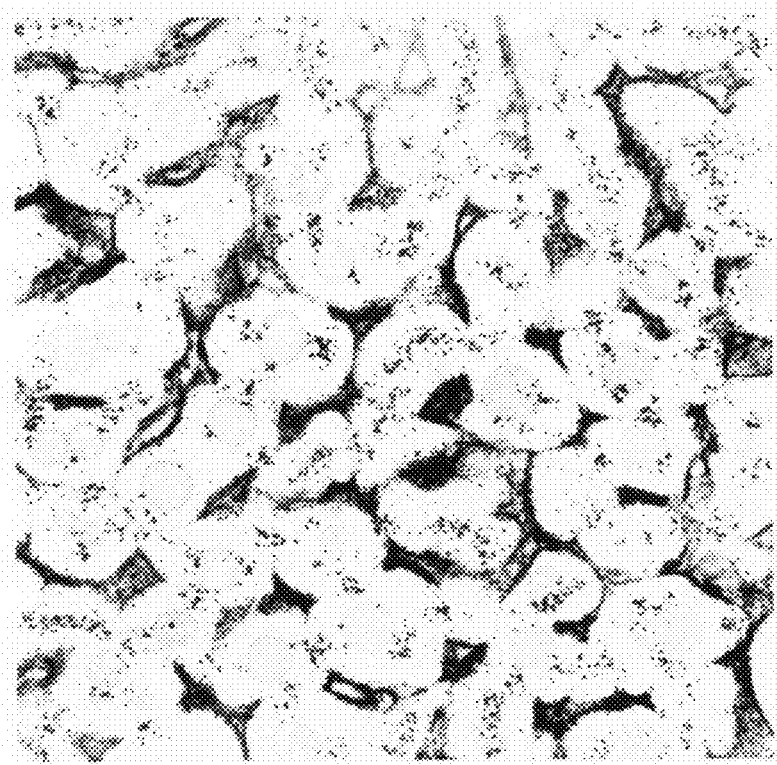
FIG. 4. Micrograph showing targeted delivery to liver hepatocytes of PBAVE polymer masked with A) CDM-PEG (left) or B) CDM-PEG plus CDM-Pip-LBA.
Figure 4:
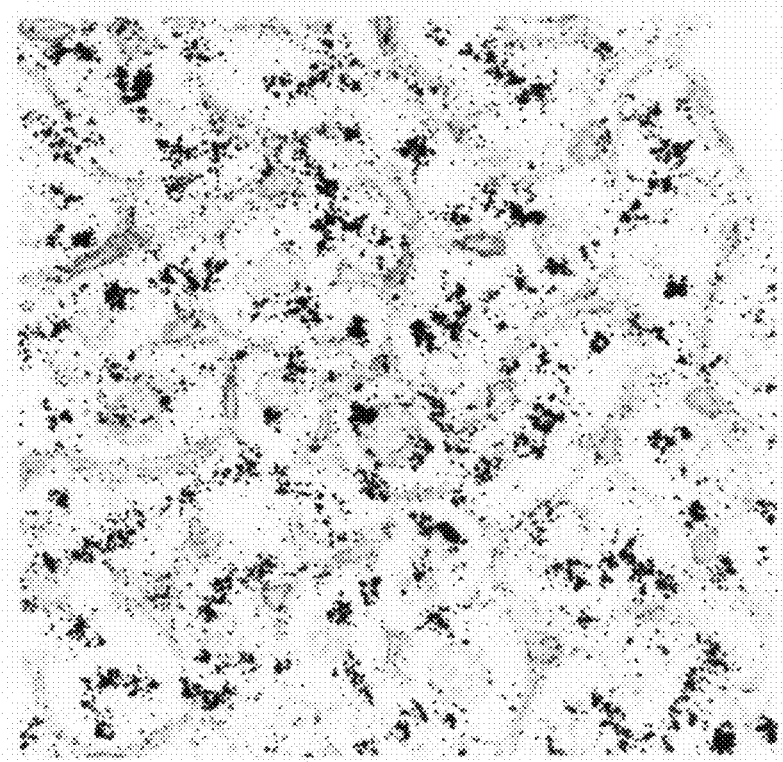

To demonstrate the ability of CDM-PIP-LBA (galactose-containing) agents to enable liver targeting of the amphipathic polyvinylether 25/75 (25:75 butyl:amine) PBAVE, the polymer was labeled with the fluorophore Cy3 followed by modification with CDM-PEG and with or without CDM-Pip-LBA. 100 µg masked polymer in 400 µl isotonic glucose was injected into the tail vein of mice. Liver samples were removed 1 h after injection and frozen liver sections were prepared and processed for immunohistochemistry (FIG. 4). As shown in FIG. 4, CDM-Pip-LBA targeted polymer was extensively located within hepatocytes (B) whereas the untargeted polymer was localized primarily with macrophages of the liver (A).

CDM-LBA modified PBAVE is highly anionic and was found primarily with macrophages (not shown). CDM-Pip-LBA (zwitterionic masking agent) modified polymers were near neutral and exhibited an increase in the amount of polymer targeted to the liver as a whole and, more importantly, to hepatocytes in particular (FIG. 4B). It is also possible to shield charge, such as negative charge, with steric stabilizers, including CDM-PEG masking agents.

Example 8

Targeting of Polynucleotide to Hepatocytes

Figure 5:
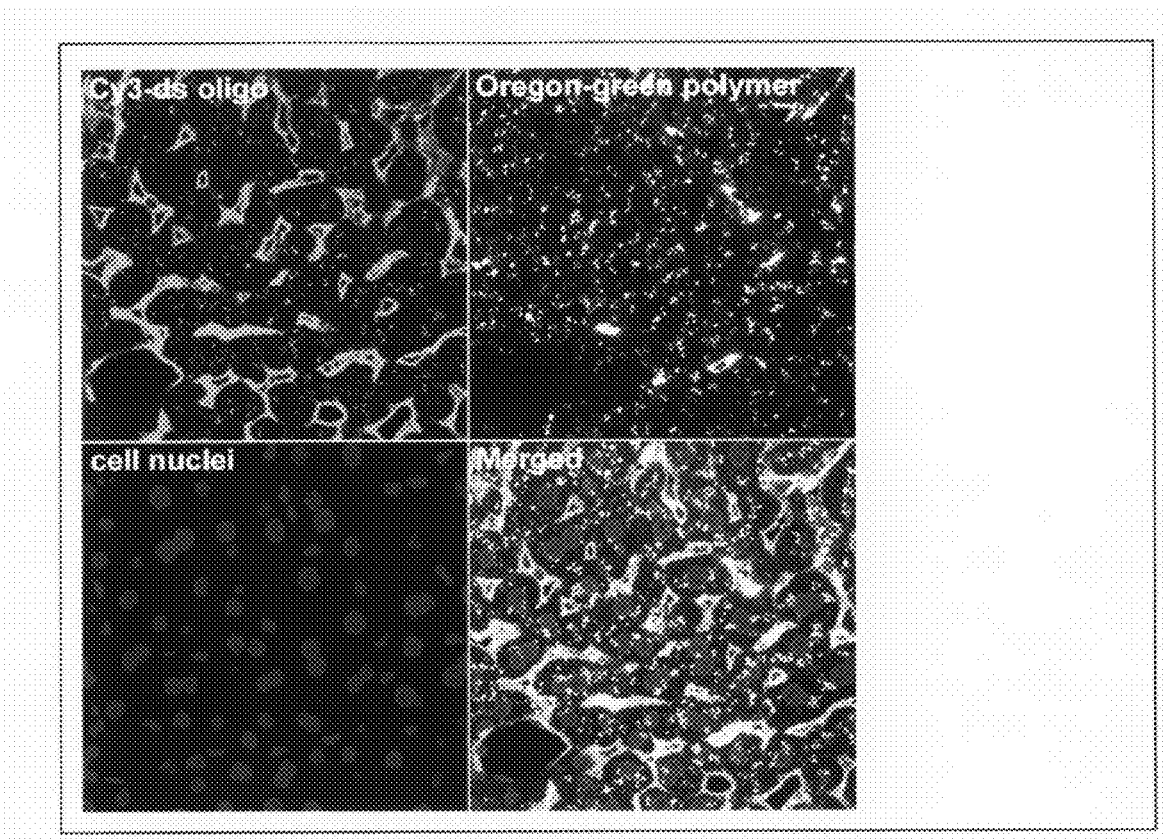
FIG. 5. Micrograph showing delivery of a masked polynucleotide-polymer conjugate to hepatocytes in vivo.

An oligonucleotide-polymer conjugate was made as described above and masked with CDM-Pip-LBA. 20 µg of SATA/Cy3 modified siRNA was conjugated to 1.8 mg of PD-modified PLL and modified with CDM-Pip-LBA. The masked conjugate was injected in 400 μL of saline into the tail vein of a mouse. In the same injection solution was 100 μg of CDM-Pip-LBA-modified 25/75-PBAVE labeled with Oregon Green. The conjugates were soluble and nonaggregating in physiological conditions. 1 h postinjection, the liver was harvested and frozen liver sections were prepared and processed for immunohistochemistry. TO-PRO-3 was used to stain cell nuclei. After injection of into the tail vein of mice, labeled oligonucleotide and PBAVE were observed in hepatocytes (top left panel of FIG. 5).

Example 9

In Vivo Activity of Conjugate

Figure 6:
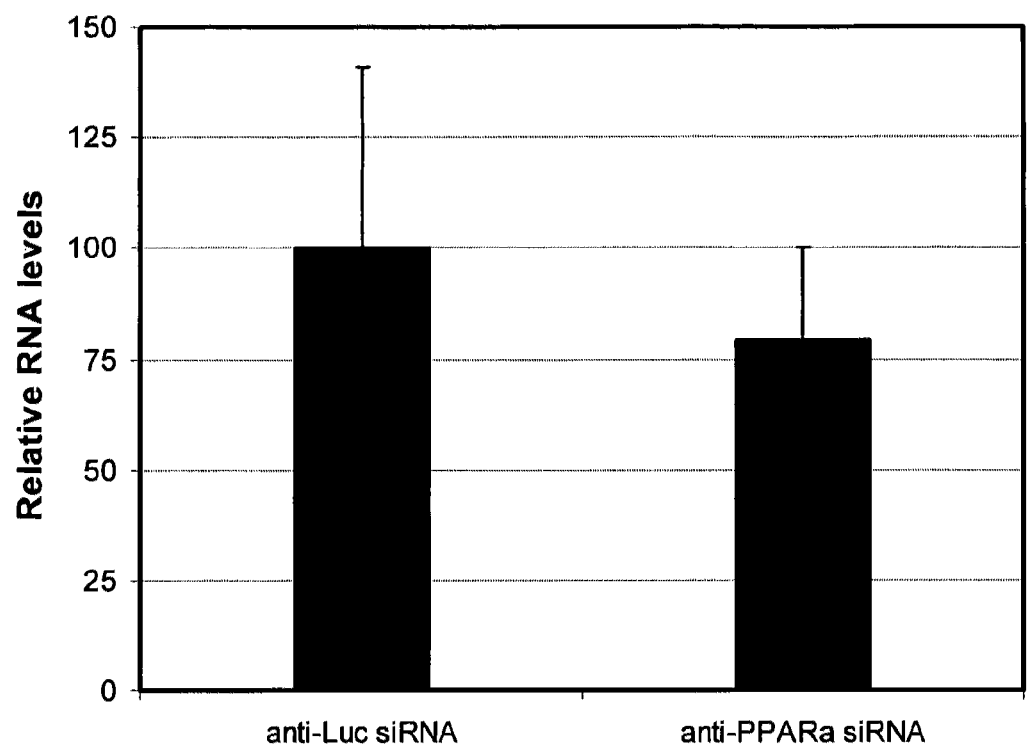
FIG. 6. Graph illustrating target gene knockdown in vivo following polyconjugate mediated delivery of ppara siRNA.
Figure 7A:
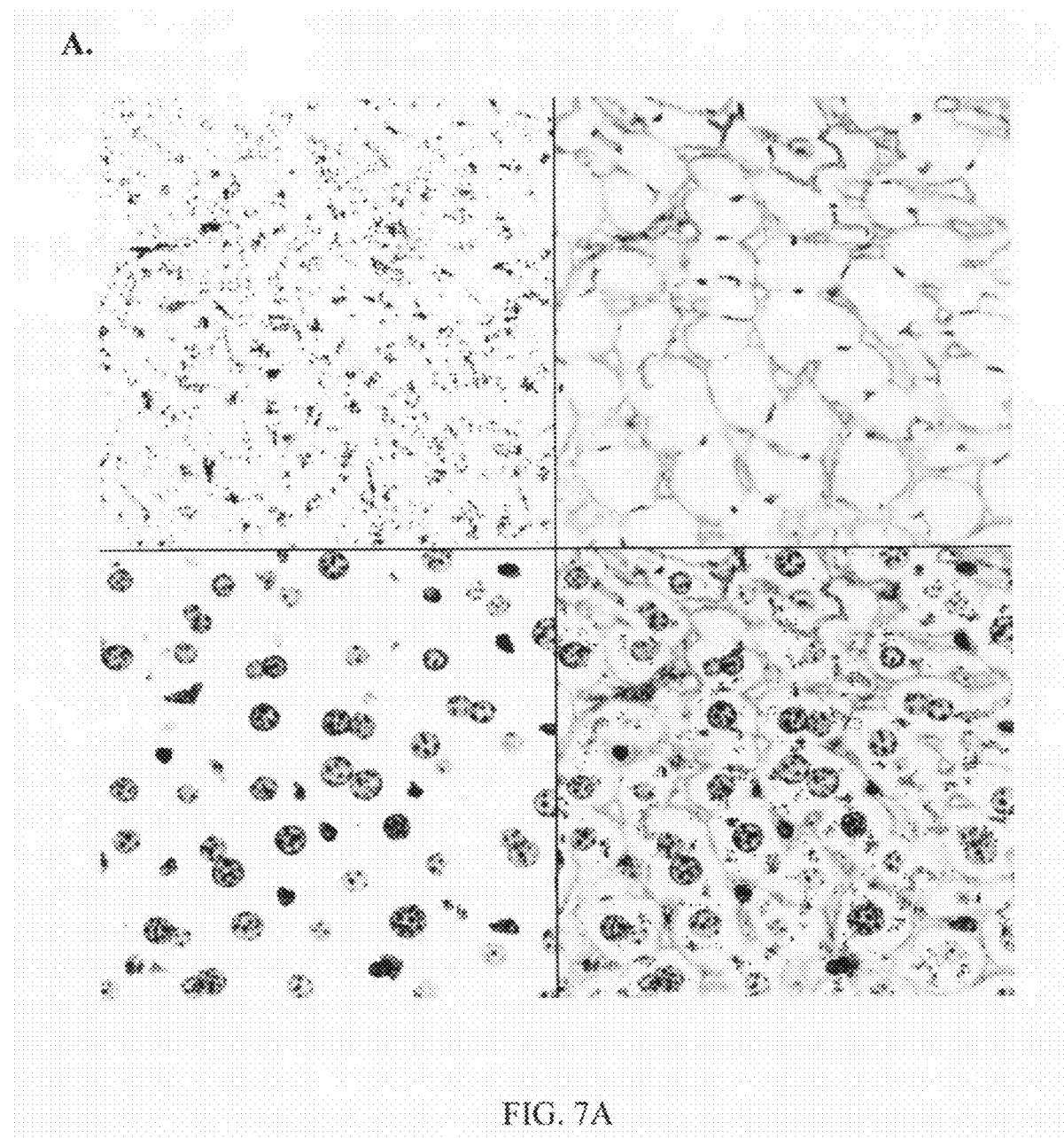
FIG. 7. Micrographs showing delivery of ds DNA to the liver in vivo with (A) DNA-DW1360-CDM-PEG/NAG, (B) DNA+DW1360-CDM-PEG/NAG (polynucleotide not conjugated to the polymer, (C) DNA-DW1360-CDM-PEG/glucose, and (D) DNA-DW1360-CDM-PEG/Mannose. Cy3-labeled DNA=upper left quadrant in each panel, ALEXA®-488 phalloidin stained actin=upper right quadrant, nuclei=lower left quadrant, and composite picture=lower right quadrant.
Figure 7B:
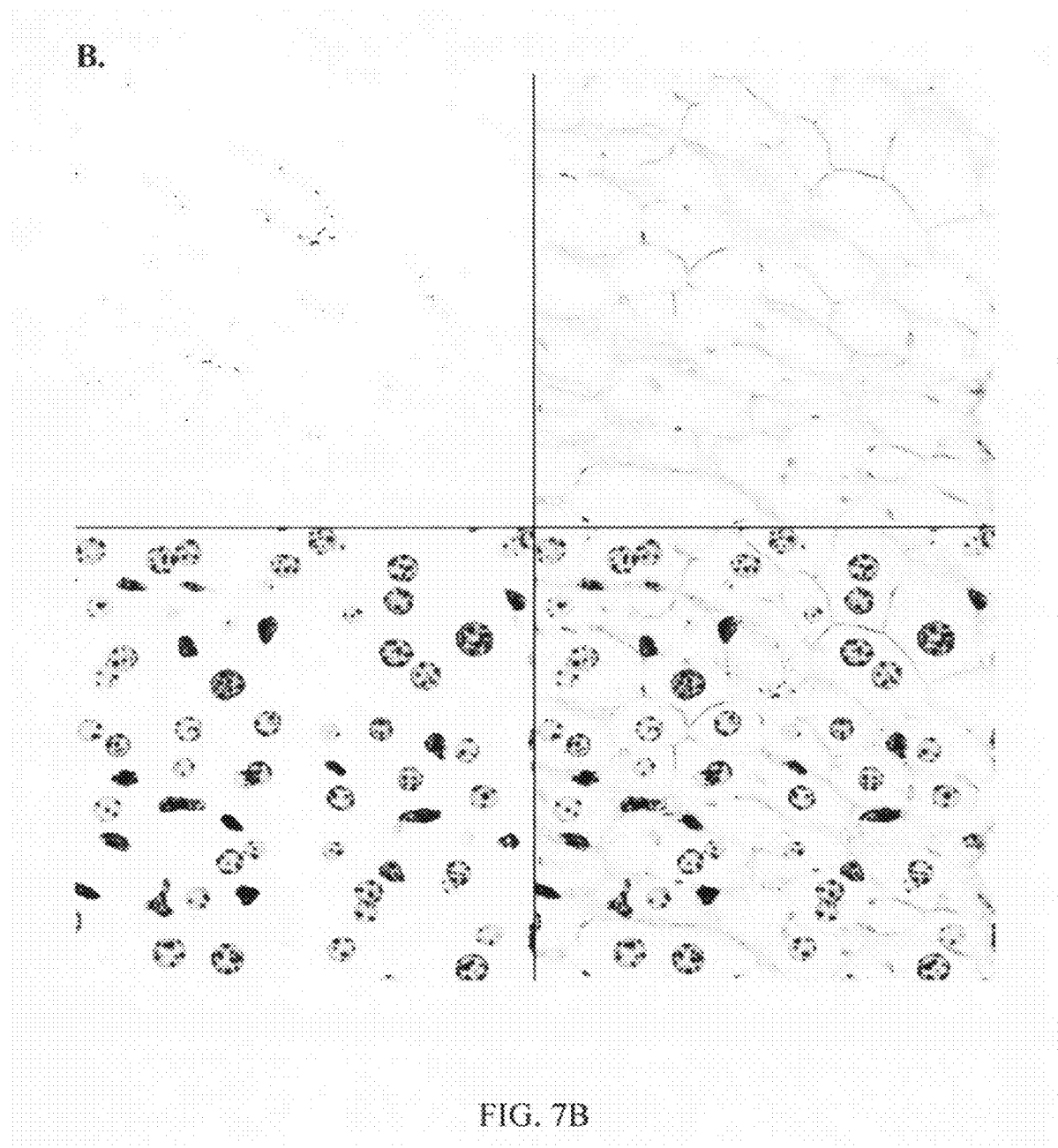
Figure 7C:
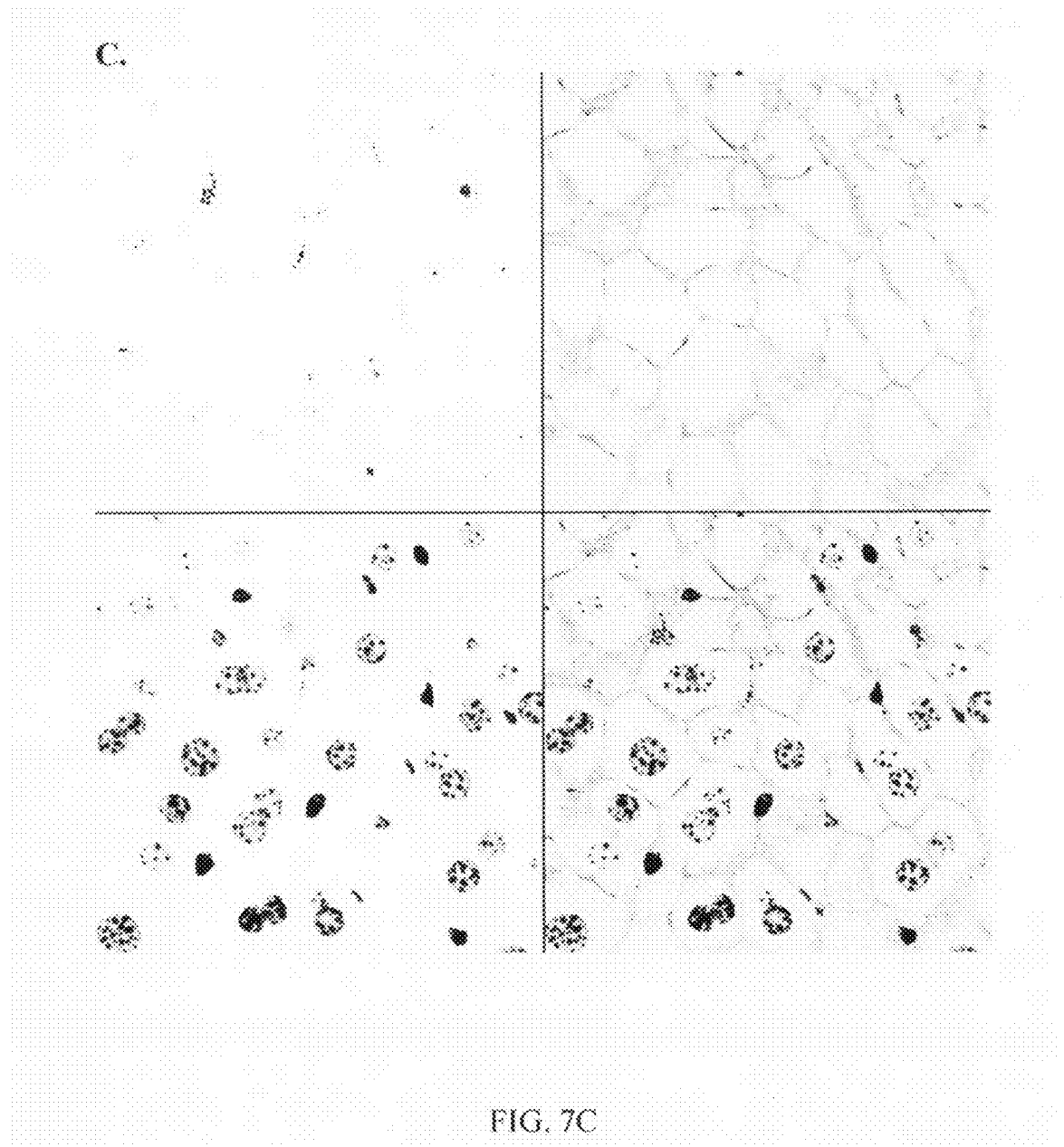
Figure 7D:
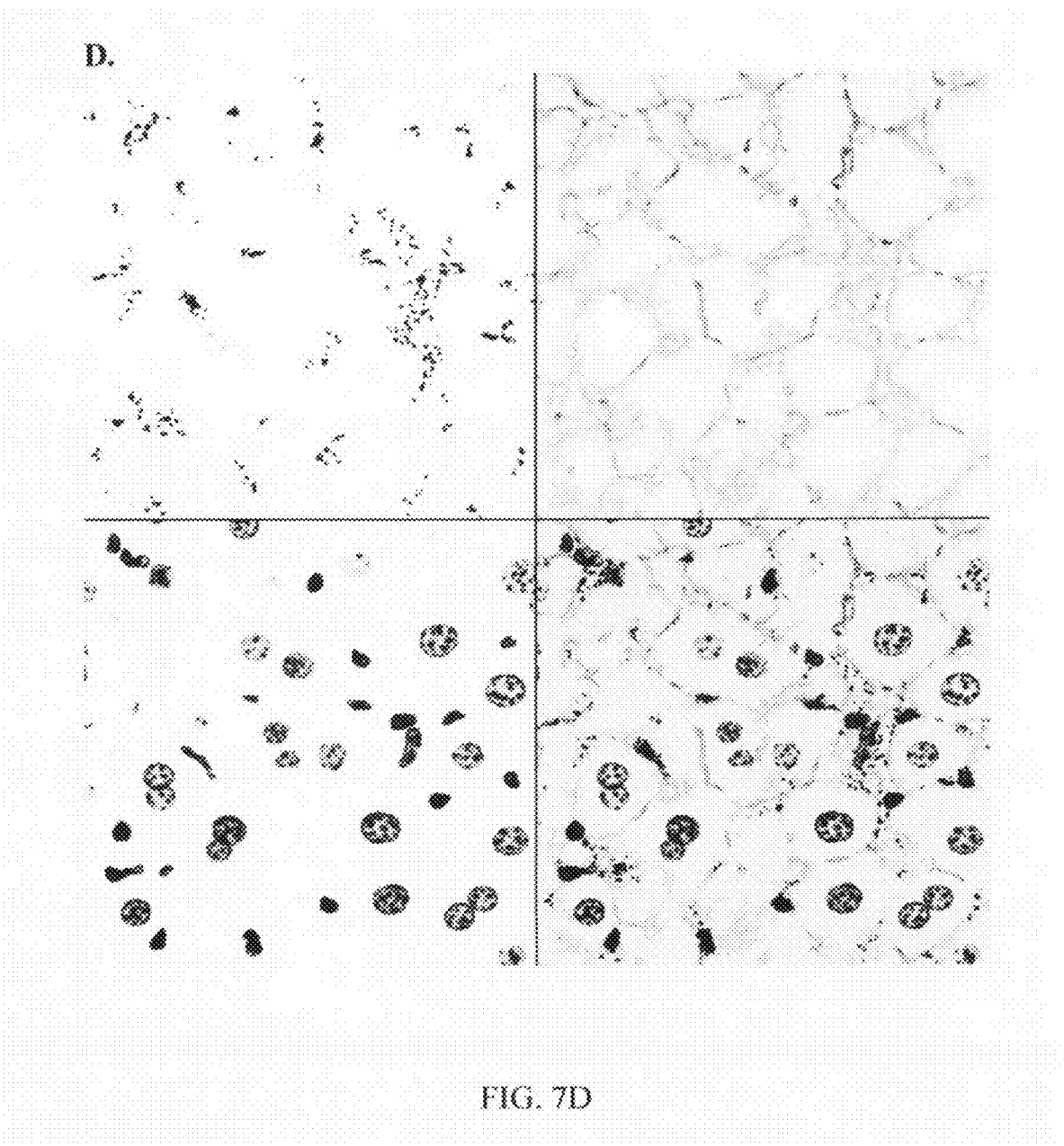

The ability of the masked polynucleotide-polymer conjugates to deliver siRNA for the inhibition of an endogenous gene in mouse liver, peroxisome proliferator activated receptor alpha (PPARa), was assessed. C57B mice (n=4) were injected with CDM-Pip-LBA modified PPARa siRNA-PLL conjugate (20 μg siRNA, 1.8 mg PD-PLL) and 25/75-PBAVE (100 μg) in 400 μL of isotonic glucose via the tail vein. RNA was prepared from liver 48 h after injection. PPARa mRNA levels were determined using a quantitative real-time PCR (qRT-PCR). mRNA levels were normalized to animals injected with anti-luciferase siRNA. Changes to mRNA levels were normalized to endogenous GAPDH. Three independent experiments were performed. As shown in FIG. 6, a 20% inhibition of PPARa mRNA levels was obtained.

Example 10

In Vivo Delivery/Activity of Conjugate

Six to eight week old male mice (strain C57BL/6, 20-25 g) were obtained from Harlan Sprague Dawley (Indianapolis, Ind.). Mice were housed at least 10 days prior to injection. Feeding was performed ad libitu with Harlan Teklad Rodent Diet (Harlan, Madison Wis.). Mice were infused with into the tail vein in a total volume of 0.4 ml injection HEPES-buffered (5 mM pH 7.5) isotonic glucose. Mice were injected with either DNA or siRNA conjugates.

Mice were fasted for 4 h prior to serum collection by retro-orbital bleed and liver harvest. Serum for use in Western assays was collected and added to an equal volume of Complete Protease Inhibitor Cocktail containing EDTA (Roche, Indianapolis Ind.) and stored at −20° C. Total RNA was isolated from liver immediately after harvest using TRI-RE-AGENT® according to the manufacturer's protocol (Molecular Research Center, Cincinnati Ohio).

For analysis of hepatocyte targeting, polyconjugate containing 10 μg of Cy3-labeled, 21-mer dsDNA was formulated as described above in a total volume of 0.2 ml and delivered into male ICR mice (20-25 g, Harlan Sprague Dawley) by i.v. injection. 1 h after injection, mice were sacrificed and liver samples were excised. In some experiments, tissue samples from lung, kidney, spleen, brain and pancreas were also excised. Tissue samples were fixed in 4% paraformaldehyde/PBS for 6 h and then placed into a 30% sucrose/PBS solution overnight at 4° C. Fixed tissue samples were then placed into block holders containing OCT freezing medium (Fisher Scientific, Pittsburgh, Pa.) and snap frozen in liquid nitrogen. Frozen tissue sections (8-10 μm) were prepared using a Microm HM 505N cryostat (Carl Zeiss, Thornwood, N.Y.) and placed onto Superfrost-Plus microscope slides (Fisher Scientific). Tissue sections were counterstained with ALEXA®-488 phalloidin (13 nM, Invitrogen, Carlsbad Calif.) and TO-PRO-3 (40 nM, Invitrogen) in PBS for 20 min. The slides were mounted in Vectashield (Vector Laboratories, Burlingame Calif.) and analyzed by a LSM510 confocal microscope (Carl Zeiss).

Confocal micrographs of liver sections taken from mice 1 h after injection with polynucleotide-polymer conjugate containing a Cy3-labeled, 21-mer double stranded DNA are shown in FIG. 7 (upper left quadrant in each panel). Actin is shown in the upper right quadrants to indicate cell outlines. Nuclei are shown in the lower left quadrants. Merged pictures are shown in the lower right quadrants. Accumulation of the Cy3-labeled dsDNA in hepatocytes was observed when the polymer contained the NAG targeting moiety, with minimal uptake by Kupffer cells or accumulation in liver sinusoids (FIG. 7A). Distribution was nearly homogenous throughout the different lobes of the liver. Inspection of other organs revealed minor Cy3-fluorescence in spleen and kidney, at levels estimated to be at least 20-fold lower than in liver. Injection of unconjugated polynucleotide+polymer or replacement of CDM-NAG on the delivery vehicle with CDM-glucose resulted in markedly reduced hepatocyte uptake and increased uptake by spleen and kidney (FIGS. 7B and 7C, respectively), which is consistent with glucose's low affinity for the asialoglycoprotein receptor. Replacement of CDM-NAG on the delivery vehicle with CDM-mannose resulted in increased macrophage and liver endothelial cell targeting (FIG. 7D).

Quantitative PCR and Invader Assays. In preparation for quantitative PCR, total RNA (500 ng) was reverse transcribed using SUPERSCRIPT III® (Invitrogen) and oligo-dT primers according to the manufacturer's protocol. Quantitative PCR was performed by using a Model 7500 Fast Real-Time PCR system (Applied Biosystems, Foster City Calif.). TAQMAN® Gene Expression Assays for apoB and ppara were used in biplex reactions in triplicate with GAPDH mRNA primers and probe using TAQMAN® Universal PCR Master Mix (Applied Biosystems). The sequence of the GAPDH primers and probe (IDT, Coralville Iowa) were:

GAPDH-forward 5'-AAATGGTGAAGGTCGGT-
  GTG-3', SEQ ID 11;

GAPDH-reverse 5'-CATGTAGTTGAGGTCAAT-
  GAAGG-3', SEQ ID 12;

GAPDH-probe 5'-Hex/CGTGCCGCCTG-
  GAGAAACCTGCC/BHQ-3', SEQ ID 13.

Direct measurements of ppara mRNA levels were performed using a custom designed INVADER® mRNA assay according to the manufacturer's instructions (Third Wave Technologies, Madison Wis.). Biplex reactions were performed in triplicate using the probe set for ubiquitin according to the manufacturer's instructions.

ApoB western, cytokine assays and liver toxicity and metabolic panels. Separation of serum proteins (0.1 μl) was accomplished by electrophoresis on 3-8% polyacrylamide/SDS gels. The separated proteins were electrophoretically transferred to PVDF membrane followed by incubation with a 1:5000 dilution of a rabbit polyclonal anti-ApoB antibody (Biodesign International, Saco Me.). The blot was then incubated with a 1:80,000 dilution of goat anti-rabbit antibody conjugated to horseradish peroxidase (Sigma), and antibody binding was detected using enhanced chemiluminescent detection kit (Amersham Biosciences, Piscataway N.J.). Serum levels of the mouse cytokines TNF-α and IL-6 were measured by sandwich ELISA using reagents according to the manufacturer's instructions (R&D Systems, Minneapolis Minn.). Serum levels of mouse IFN-α were measured using a sandwich ELISA kit according to the manufacturer's instructions (PBL Biomedical, Piscataway N.J.). Serum levels of ALT, AST, cholesterol, and triglycerides were measured using automated systems at the Marshfield Clinic Laboratories Veterinary Diagnostic Division (Marshfield Wis.).

Serum Levels of Cytokines and Liver Enzymes in siRNA Conjugate-Treated Mice.

| Treatment | | TNF-α (pg/ml) | IL-6 (pg/ml) | IFN-α (pg/ml) | ALT (U/L) | AST (U/L) |
|---|---|---|---|---|---|---|
| Saline | 6 h | <6 | <2 | 206 ± 51 | 60 ± 21 | 149 ± 21 |
| | 48 h | <6 | <2 | 321 ± 77 | | |
| Control siRNA | 6 h | 7.9 ± 2.9 | 60.2 ± 2.4 | 207 ± 86 | 97 ± 26 | 176 ± 62 |
| | 48 h | <6 | 4.0 ± 1.3 | 211 ± 16 | | |
| apoB-1 siRNA | 6 h | 57.9 ± 7.2 | 48.6 ± 2.5 | 494 ± 165 | 71 ± 30 | 144 ± 34 |
| | 48 h | <6 | <2 | 257 ± 70 | | | n = 5, data are shown as mean ± s.d.

Example 11

Knockdown of Target Genes in Liver of Mice

Figure 8:
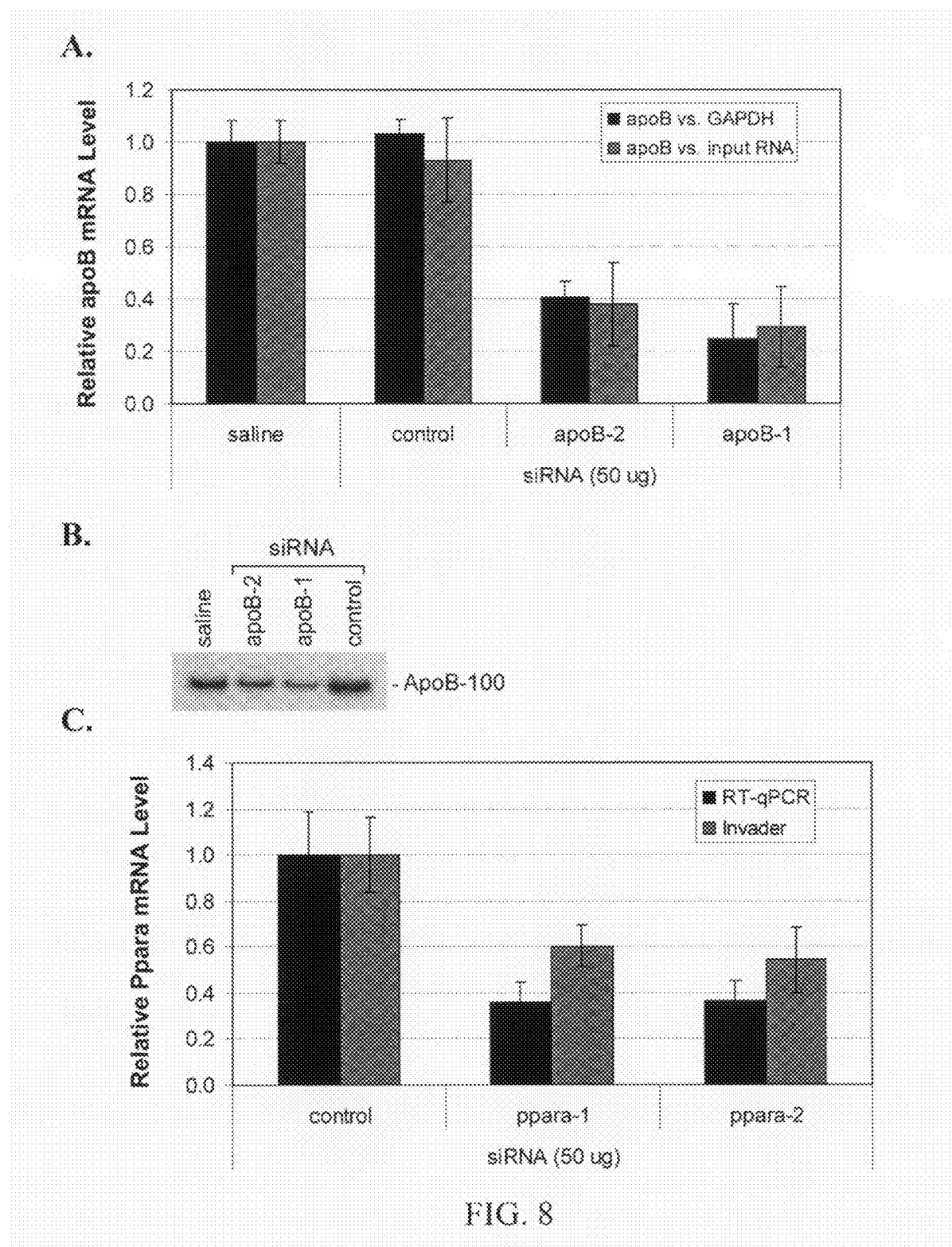
FIG. 8. Graphs and blot illustrating knockdown of target gene expression in livers of mice after intravenous injection of siRNA polyconjugates. (A) Reduction of apoB mRNA levels in liver after treatment with apoB siRNA polyconjugates. (B) Serum levels of apoB-100 protein in apoB siRNA polyconjugate-treated mice. (C) Reduction of ppara mRNA levels in liver after intravenous injection of ppara siRNA polyconjugates.

To demonstrate the ability of the system to deliver siRNA and knockdown target gene expression in vivo, conjugate containing apoB-1 siRNA (800 μg polymer, 50 μg siRNA) was injected into C57Bl/6 mice. As in the in vivo targeting studies, the siRNA conjugate was administered by tail vein infusion. Livers from injected mice were harvested two days after injection and assayed for apoB mRNA levels using reverse transcriptase quantitative PCR (RT-qPCR). The apoB mRNA levels were measured relative to the level of GAPDH mRNA and μg total input RNA, in order to reduce the possibility that any differences in relative apoB mRNA levels were due to nonspecific effects on housekeeping gene expression. As shown in FIG. 8A, mice treated with apoB-1 siRNA conjugate had significantly reduced apoB mRNA levels compared to mice receiving a non-apoB control siRNA or mice injected with saline only (n=5, p<0.00001), as measured two days after injection. Specifically, the mean apoB mRNA level in mice receiving apoB-1 siRNA conjugate was reduced by 76±14% compared to the saline treated group relative to GAPDH mRNA levels, whereas apoB mRNA levels in mice injected with the control siRNA were unaffected. Similar results were obtained if apoB mRNA levels were measured relative to total RNA. Western blot analysis of apoB-100 protein levels in serum reflected the reduction in liver apoB mRNA levels (FIG. 8B).

To confirm the specificity of the apoB knockdown, a separate group of mice was treated with an siRNA targeting a different region of the apoB mRNA. Mice receiving apoB-2 siRNA conjugate also exhibited a significant reduction in apoB mRNA levels (60±6% reduction, n=5, p<0.00001, FIG. 8A). Western blot analysis of apoB-100 protein levels in serum reflected the reduction in liver apoB mRNA levels (FIG. 8B). ApoB mRNA expression was not reduced in the jejunum, another tissue that expresses the apoB gene, suggesting that the conjugate did not target this tissue. This tissue-specific activity is consistent with hepatocyte targeting.

We also prepared conjugates containing siRNAs targeting peroxisome proliferator-activated receptor alpha (ppara), a gene important in controlling fatty acid metabolism in liver (Kersten 1999, Schoonjans 1996). Delivery of two different siRNAs targeting ppara resulted in significant knockdown of ppara mRNA levels, as assayed by two independent methods for quantifying mRNA levels (FIG. 8C). Relative to mice receiving a control siRNA, ppara mRNA levels in mice receiving ppara-1 siRNA were reduced by between 40±9% and 64±9%, as assayed by IINVADER® or RT-qPCR, respectively. A similar reduction in ppara mRNA levels was observed in mice injected with delivery vehicle containing ppara-2 siRNA, which targets a separate region of the ppara mRNA sequence.

The potential toxicity of the delivery system was assessed by measuring serum levels of liver enzymes and cytokines. Slight elevations of ALT and AST levels were detected in mice receiving control siRNA or apoB-1 siRNA conjugates as compared to saline-treated mice, 48 h after injection. However, the increased levels were not significant (p<0.05) and histological examination of liver sections did not reveal signs of liver toxicity. Similarly, analysis of TNF-α and IL-6 levels in serum using ELISA revealed that both were slightly elevated 6 h after injection of siRNA-polymer conjugate, but returned to baseline by 48 h. The increases observed at 6 h would not be expected to cause significant immune stimulation and are at least four orders of magnitude lower than those observed upon stimulation with lipopolysaccharide (Matsumoto 1998, Matsuzaki 2001) and one to three orders of magnitude lower than after injection of adenovirus (Lieber 1997, Benihoud 2007). No significant differences in serum levels of INF-α were detected at any of the timepoints, except for a slight increase at 6 h after injection of apoB-1 siRNA conjugate. These results indicate the targeted delivery system is well-tolerated.

Example 12

Dose-Response and Phenotypic Analysis

We performed dose-response studies in two ways: by decreasing the amount of siRNA conjugate delivered to the mice or by holding the amount of polymer constant but decreasing the amount of conjugated siRNA. By comparing the results of these experiments, we hoped to determine which of the two components of the delivery vehicle was limiting for delivery: the endosomolytic polymer or the siRNA itself.

Figure 9:
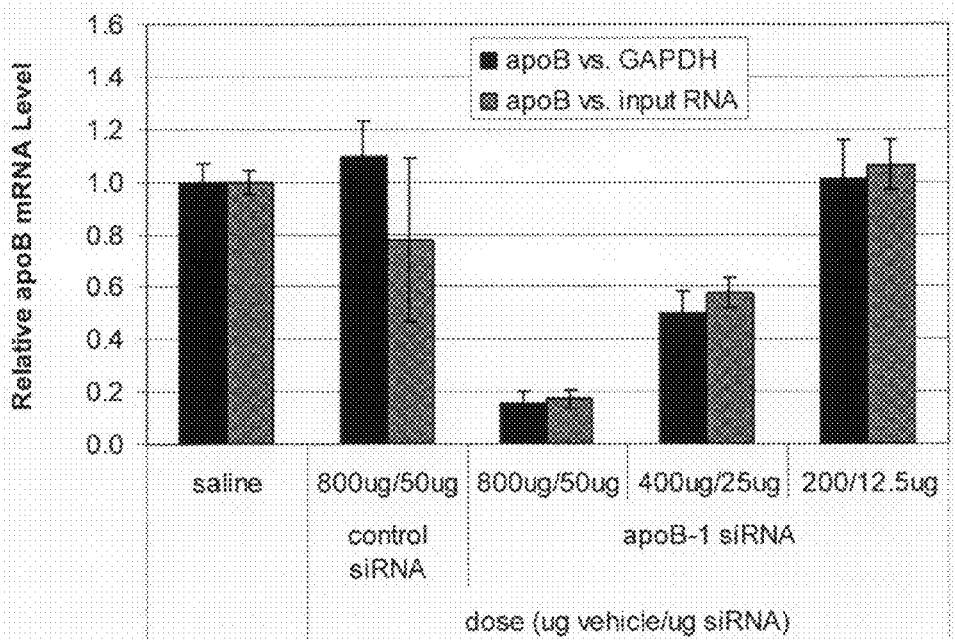
FIG. 9. Graph illustrating apoB-1 siRNA polyconjugate dose response. (A) Knockdown of apoB mRNA after injection of serial dilutions of the apoB-1 siRNA polyconjugate. (B) Knockdown of apoB mRNA after injection of varying amounts of siRNA.
Figure 9:
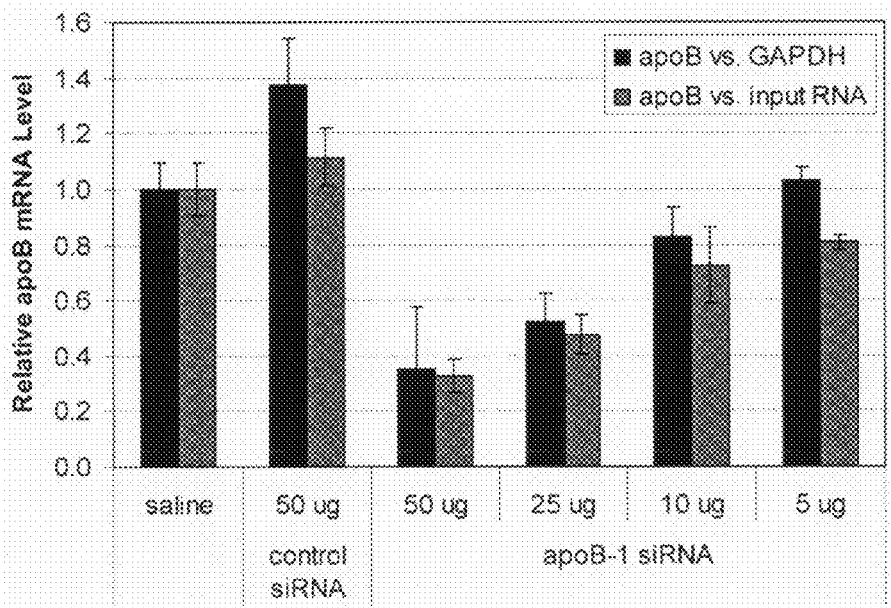

Injection of simple serial dilutions of the apoB-1 siRNA conjugate into mice led to a progressive decrease in the amount of knockdown of liver apoB mRNA (FIG. 9A). At the highest injected dose (800 μg polymer, 50 μg siRNA, i.e. 2.5 mg/kg), apoB mRNA levels in the liver were reduced 84±5% relative to GAPDH mRNA on Day 2 postinjection compared to mice injected with saline only. Similar results were obtained when apoB mRNA levels were measured relative to total RNA. Injection of two-fold less siRNA conjugate (400 µg polymer, 25 µg siRNA) resulted in a 50±8% reduction in relative apoB mRNA levels. Injection of four-fold less resulted in no apoB knockdown as compared to the saline control group. Holding the amount of polymer constant but decreasing the amount of apoB-1 siRNA conjugated to the delivery vehicle led to quantitatively similar results to those obtained from serial dilutions (FIG. 9B). This finding suggests that the amount of endosomolytic polymer present in the delivery vehicle is not the limiting factor for the knockdown observed, but rather it is the amount, or potency, of the siRNA conjugated to it.

Figure 10:
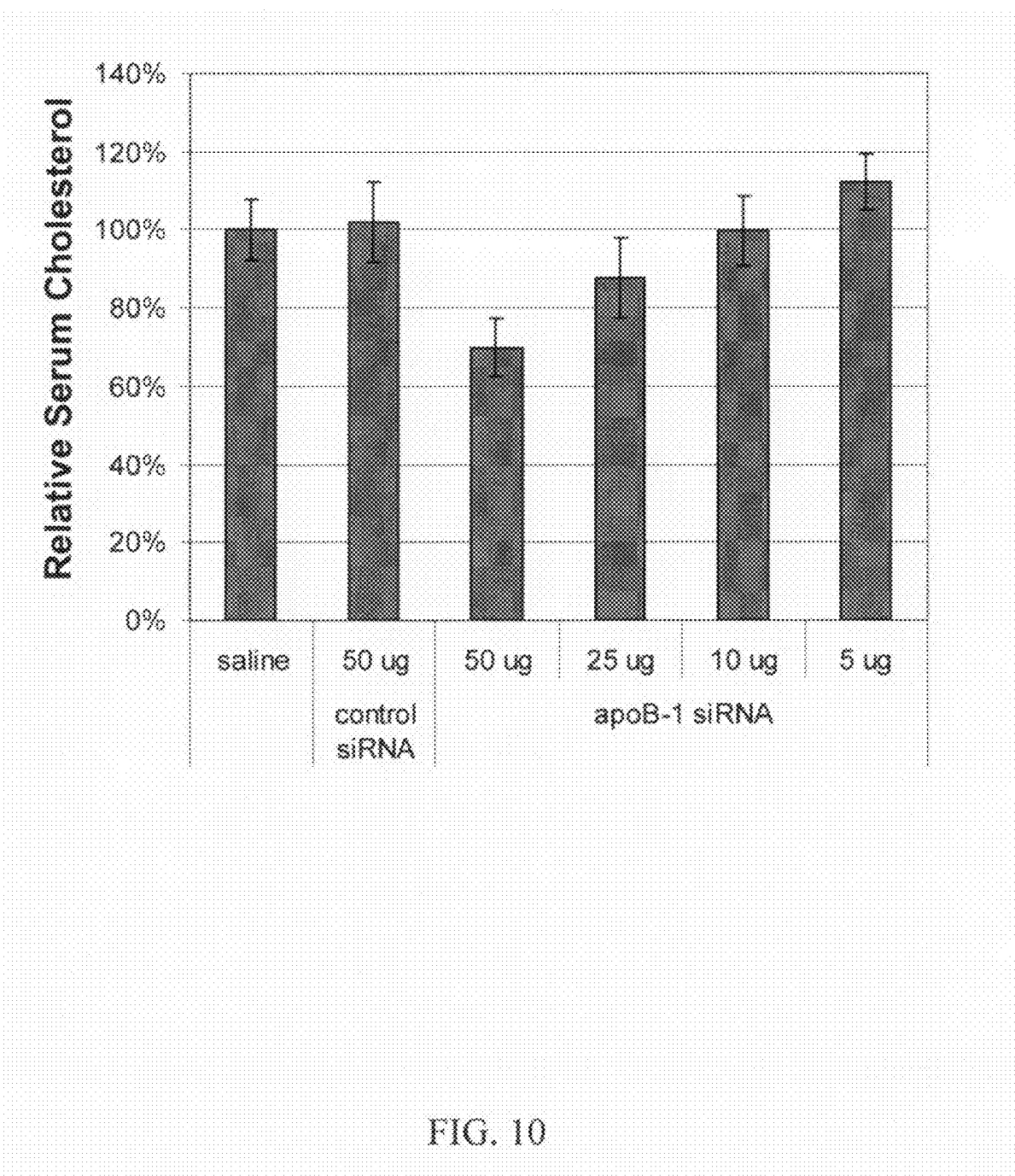
FIG. 10. Graph illustrating cholesterol levels in apoB-1 siRNA polyconjugate treated mice.

A hallmark of apoB deficiency is decreased serum cholesterol levels due to impairment of VLDL assembly and cholesterol transport from the liver (Burnett Zimmermann 200602). To determine if the level of knockdown of apoB shown in FIG. 10 was sufficient to elicit a physiological response in these mice, we measured their total serum cholesterol levels. At the highest delivered siRNA dose (50 µg), we observed a significant decrease in mean serum cholesterol levels (30±7%, n=5, p<0.001) relative to mice receiving a control siRNA or saline only (FIG. 10). Similar results were obtained in animals treated with apoB-2 siRNA conjugate. Decreasing the amount of siRNA delivered led to a progressive decrease in the amount of cholesterol lowering observed, consistent with decreased apoB mRNA knockdown measured in these animals.

Figure 11:
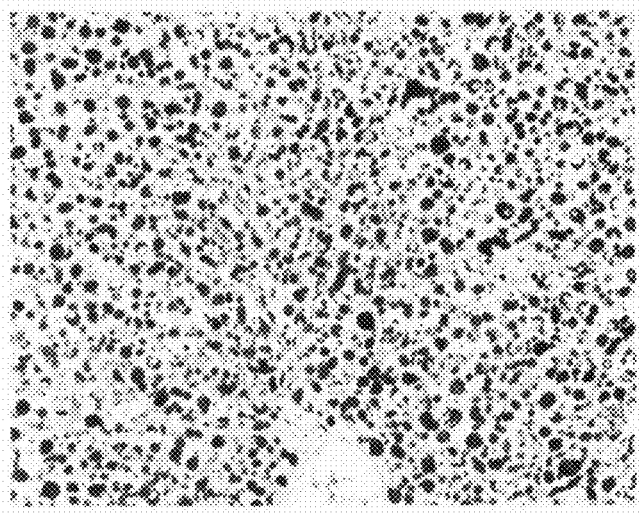
FIG. 11. Micrographs showing lipid accumulation in mouse liver following polyconjugate delivery of (A) ApoB siRNA or (B) GL3 negative control siRNA, or (C) saline alone.
Figure 11:
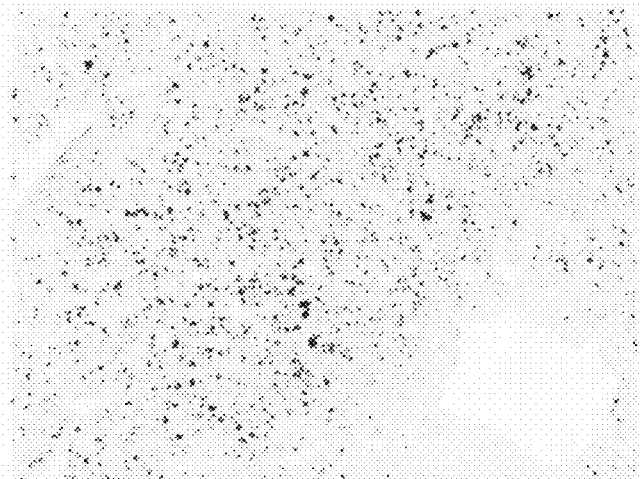
Figure 11:
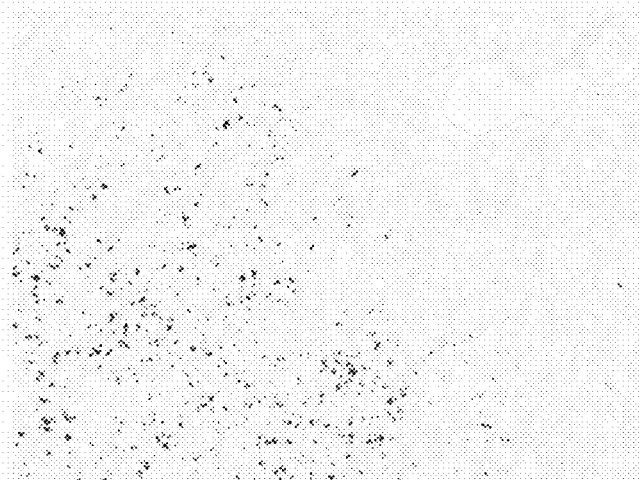

Impairment of VLDL assembly in the liver and the resultant decrease in VLDL export might also be expected to alter hepatic triglyceride levels because triglycerides are also incorporated into VLDL particles (Gibbons 2004). Indeed, transgenic mice expressing a truncated form of apoB, similar to the version found in patients with familial hypobetalipoproteinemia, also display a reduced capacity to transport hepatic triglycerides (Chen 2000). In order to assess the effects of apoB knockdown on triglyceride transport, we performed oil red staining of liver sections obtained from mice injected with apoB-1 siRNA conjugate. Inspection of the liver sections revealed dramatically increased hepatic lipid content compared to control mice (FIG. 11). Panel A shows a mouse treated with ApoB siRNA. Panel B shows a mouse treated with negative control GL3 siRNA. Panel C shows a mouse injected with saline alone. Decreased serum triglyceride levels were also detected in these mice, providing further evidence for diminished hepatic triglyceride export capacity. Together, these results indicate that simple i.v. injection of apoB-1 siRNA conjugate results in functional delivery of the polynucleotide to hepatocyte and therefore knockdown of expression of apoB in the liver with expected phenotypic effects.

For analysis of liver fat accumulation, liver samples from siRNA-conjugate-treated and control mice were frozen in OCT freezing medium and frozen tissue sections (8-10 µm) were prepared as described above. Air dried tissue sections were fixed in 4% formaldehyde/PBS for 20 min, rinsed in several changes of distilled water, and then rinsed briefly with 60% isopropanol. Oil red O stock solution was prepared by mixing 0.5 g of oil red O in 100 ml of isopropanol overnight and filtered using Whatman #1 filter papers. Oil red O working solution was prepared by mixing 20 ml of water with 30 ml of oil red O stock solution and filtered using a 0.2 µm Nalgene filtration unit (Fisher Scientific). The fixed sections were stained with freshly prepared oil red O working solution for 15 min, rinsed briefly with 60% isopropanol. Counterstaining of nuclei was performed by dipping the slides into Harris modified hematoxylin solution (Sigma, St. Louis Mo.) 7 times and rinsed in distilled water. Rinsed slides were then mounted with Gel Mount (Biomedia Corp., Foster City Calif.). Stained slides were analyzed using a Zeiss Axioplan 2 microscope equipped with a digital camera (Axiocam, Carl Zeiss). Digital images were captured using the AxioVision software (Carl Zeiss).

Example 13

Delivery of siRNA by Conjugation to Membrane Active Polymer by a CDM or Disulfide Labile Linkage Disulfide Conjugate: 50 ng of siRNA targeted against luciferase that had a 5'-amino group on the sense strand was reacted with 1 µg of N-succinimidyl-S-acetylthioacetate in the presence of HEPES base pH 7.5. Separately, 50 µg of a polyvinylether synthesized from a 50/50 mixture of amine-protected and butyl vinyl ether monomers was reacted with 5 µg of 3-(2-pyridyldithio)propionic acid N-hydroxysuccinimide ester in the presence of HEPES pH 7.5. The modified siRNA and modified polymer were then combined to allow covalent attachment of the siRNA to the polymer. After 6-24 h, the polymer-siRNA conjugate was reacted with 200 µg of 2-propionic-3-methylmaleic anhydride in the presence of HEPES base. The particles were added to a mouse hepatocyte HEPA cell line that stably expresses the luciferase gene. As a control, samples containing CDM-modified polymer (without siRNA) were added to cells. In cells exposed to the polymer-polynucleotide conjugate, luciferase expression was suppressed 75% relative to cells exposed to polymer alone, indicating delivery of functional siRNA to the cells.

CDM Conjugate: 50 ng of siRNA targeted against luciferase that had a 5'-amino group on the sense strand was reacted with 2 µg of CDM thioester in the presence of HEPES pH 7.9. To the siRNA was added 50 µg of a polyvinylether synthesized from a 50/50 mixture of amine-protected and butyl vinyl ether monomers. After 6-24 h, the polymer-siRNA conjugate was reacted with 200 µg of 2-propionic-3-methylmaleic anhydride in the presence of HEPES base. The particles were added to a mouse hepatocyte HEPA cell line that stably expresses the luciferase gene. As a control, samples containing CDM-modified polymer (without siRNA) were added to cells. In cells exposed to the polymer-polynucleotide conjugate, luciferase expression was suppressed 86% relative to cells exposed to polymer alone, indicating delivery of functional siRNA to the cells.

Percent inhibition of luciferase activity following transfection of HEPA-Luc cells using membrane active polymer-siRNA conjugates.

| Disulfide Conjugation | CDM Conjugation |
| --- | --- |
| 75% | 86% |

Example 14

Longevity of apoB Knockdown and its Phenotypic Effect

Figure 12:
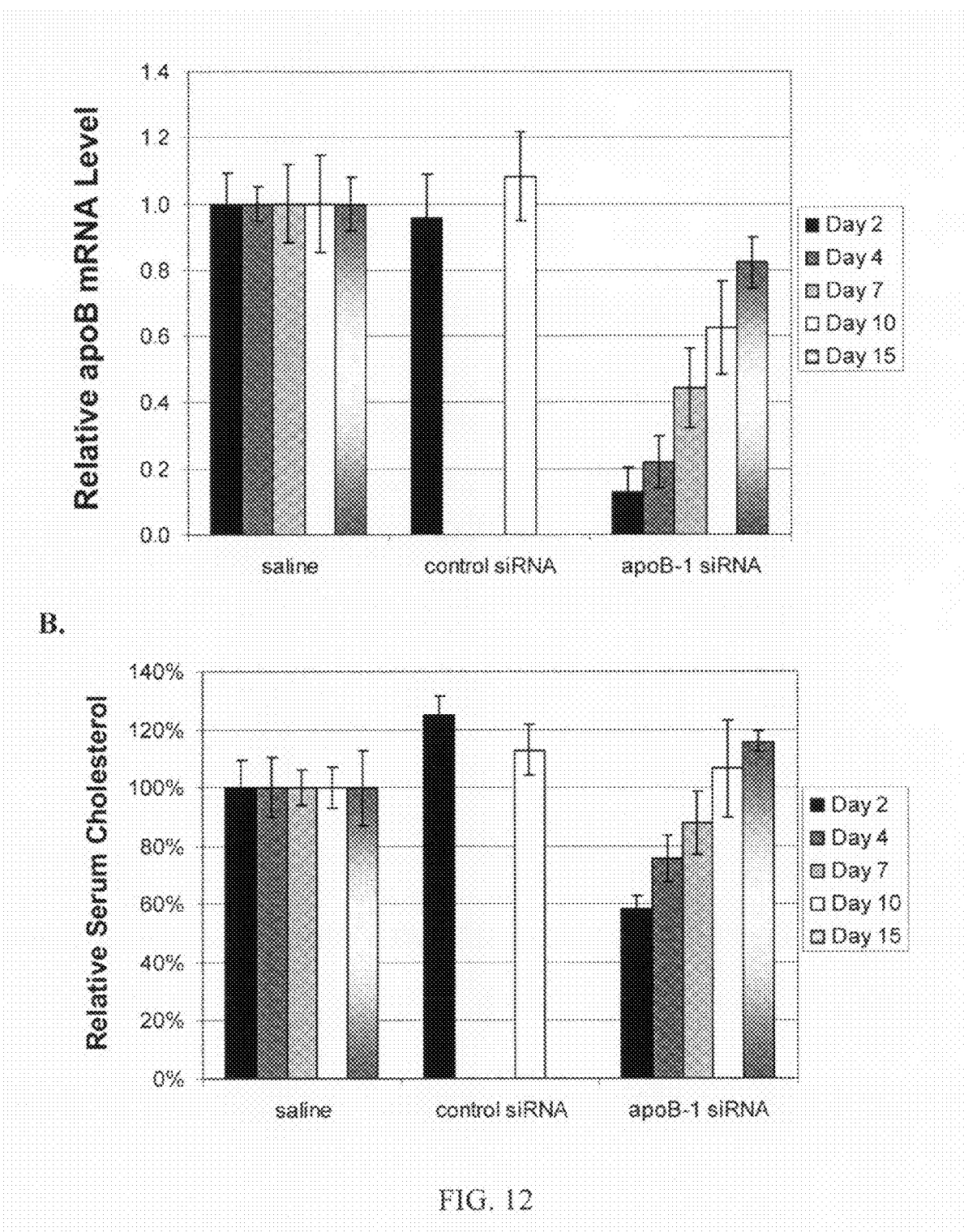
FIG. 12. Graph illustrating inhibition of gene expression (A), and resultant decrease in serum cholesterol (B) and day 2-15 following administration of apoB-1 siRNA conjugate in mice on day 0.

We performed a timecourse experiment to determine the duration of apoB knockdown and cholesterol lowering in mice after injection of a single dose of apoB-1 siRNA conjugate. Consistent with our results described in the previous sections, injection of apoB-1 siRNA conjugate (800 µg polymer, 50 μg siRNA) resulted in reduction of mean apoB mRNA levels by 87±8% on Day 2 relative to control mice (FIG. 12A). The reduction in apoB expression was accompanied by a 42±5% reduction in total serum cholesterol levels (FIG. 12B). Decreases in apoB mRNA expression remained significant through Day 10, and had returned to near control levels by Day 15. Reduction in serum cholesterol remained significant through Day 4 (n=5, p<0.01), and did not fully recover to control levels until Day 10. These results indicate that sustained apoB knockdown and the generation of the phenotype can be achieved after a single injection of siRNA conjugate, and that the phenotype can be reversed as apoB expression returns to normal over time.

Example 15

The Delivery of Phosphorodiamidate Morpholino Oligonucleotide (PMO) to Cells Using Polymer-PMO Conjugates Using the CDM-thioester based crosslinking used to link siRNA and polymer, it is also possible to reversibly conjugate other types of oligonucleotides to polymers. In particular, we studied the delivery of PMO to cells. 5 nmol of amino-PMO (which blocks a mutant splice site in the mutant Luciferase transcript) either bare or hybridized with a complimentary strand of DNA was reacted with nothing or with 2 μg of CDM thioester in the presence of HEPES pH 7.9. To this was added 200 μg of polyvinyl ether synthesized from 50% amino vinylether, 45% butyl vinylether and 5% dodecylvinylether (DW550). After three or more hours the polymer+PMO or polymer-PMO conjugate was reacted with 500 μg of CDM in the presence of HEPES to maintain pH>7.5. In addition to CDM, the conjugates were reacted with PEG esters of CDM, which are derived from the acid chloride of CDM and PEG monomethyl ethers of various molecular weights. The conjugates were then added HeLa Luc/705 cells (Gene Tools, Philomath Oreg.) grown under conditions used for HeLa cells. The cells were plated in 24-well culture dishes at a density of $3 \times 10^6$ cells/well and incubated for 24 h. Media were replaced with 1.0 ml DMEM containing 2.5 nmol amino-PMO complexes. The cells were incubated for 4 h in a humidified, 5% $CO_2$ incubator at 37° C. The media was then replaced with DMEM containing 10% fetal bovine serum. The cells were then incubated for an additional 48 h. The cells were then harvested and the lysates were then assayed for luciferase expression. The results demonstrate enhanced delivery of the uncharged polynucleotide when the transfection agent is a DW550 polyvinylether polymer-PMO conjugate.

Delivery of Uncharged Polynucleotides to Cells

| Transfection vehicle | Fold induction of luciferase |
|---|---|
| no linkage | |
| DW550 + bare PMO | 2 |
| DW550 + PMO hybridized with DNA | 2 |
| polymer-PMO conjugate | |
| DW550-CDM-barePMO | 7.5 |
| DW550-CDM-hybridized PMO | 10 |

Example 16

Conjugate Delivery of siRNA to Muscle

40 μg PPARa siRNA or control (GL3) siRNA was conjugated to PBAVE polymer and masked as described above. 250 μl conjugate was injected into the gastrocnemius muscle in mice (n=3). Injection rate was about 25 μl/sec. PPARa expression levels were determined as described above.

PPARa Inhibition in Muscle Following Direct Injection of Masked Conjugate

| | PPARa mRNA levels relative to: | |
|---|---|---|
| siRNA conjugate | GAPDH mRNA | total mRNA |
| GL3 | 1.00 ± 0.26 | 1.00 ± 0.15 |
| PPARa | 0.62 ± 0.07 | 0.54 ± 0.13 |

Example 17

In Vivo Delivery of siRNA Expression Cassette

20 μg of PCR-generated linear SEAP siRNA expression cassette, which expresses SEAP siRNA under control of the U6 promoter, was complexed with 400 μg membrane active polymer DW1453 (composed of polymerization of 75 mol % amino, 21 mol % lower alkyl(butyl) and 4 mol % higher alkyl (C18, octadecyl) groups and modified with galactose with lactobionic acid (LBA). Lactobionylation was performed by addition of 43 mg LBA to 60 mg polymer followed by addition of 34 mg EDC and 24 mg NHS. As a control, a cassette expressing luciferase siRNA (GL3) was also formulated. The DNA was conjugated to the polymer by the addition of 0.65 weight equivalents of glutaraldehyde. Following conjugation overnight, the complexes were modified with 40 mole % NHS-acetate to reduce charge on the polymer.

500 μg of lactobionylated DW1453 was modified with 7 wt equivalents of masking agent CDM-PEG (average 10 units) in the presence of 14 wt equivalents HEPES base and injected into the tail vein of mice expressing secreted alkaline phosphatase (SEAP). 10 min after masked polymer injection, the co-targeted DNA-DW1453 polymer conjugates were injected. On days 1 and 14, blood was drawn and assayed for SEAP levels.

| siRNA | SEAP activity day 14 relative to activity at day 1 |
|---|---|
| SEAP siRNA | 48 ± 13 |
| GL3 siRNA | 87 ± 17 |

Activity was the average of 4 animals ± standard deviation.

Example 18

Delivery of Antibodies

Figure 13:
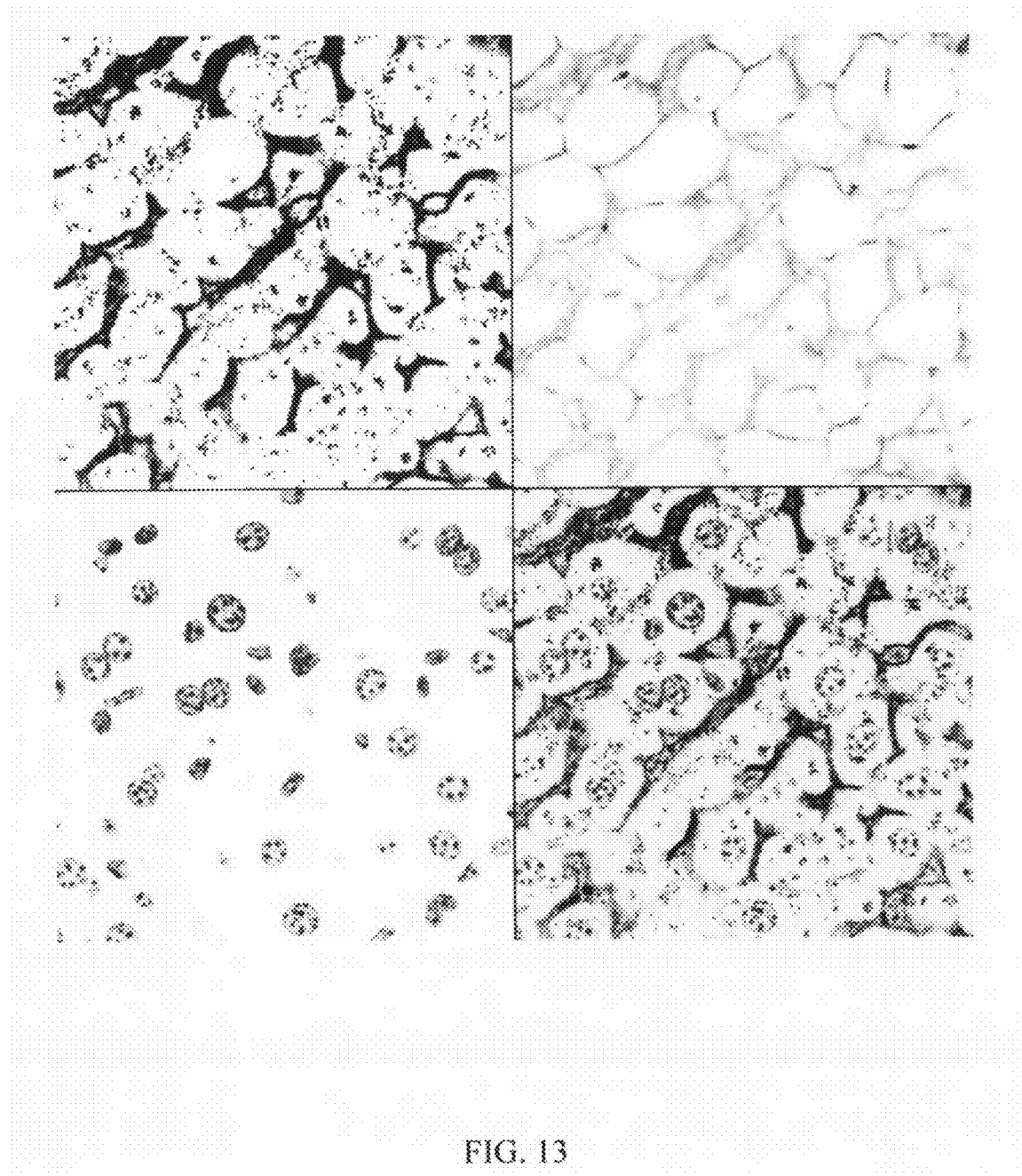
FIG. 13. Micrograph showing in vivo delivery antibodies to hepatocytes via administration of antibody reversibly conjugated to DW1360 and masked with CDM-PEG and CDM-NAG. Upper left quadrant shows labeled antibodies, Upper right quadrant shows actin, lower left quadrant shows nuclei, and lower right quadrant shows a composite image.

35 μg of rabbit IGG (Sigma) antibody was modified with 2 wt % SPDP (Pierce). DW1360 (30 mg/ml in 5 mM TAPS pH 9) was modified by addition of 2 wt % iminothiolane. 530 μg of iminothiolane-PBAVE was added to 400 μl isotonic glucose solution containing 5 mM TAPS pH 9. To this solution was added 35 μg of SPDP-modified antibody. After 16 h, the antibody-polymer conjugate was modified with 7 wt eq of a 2:1 mixture of CDM-NAG and CDM-PEG. The conjugate was injected into the tail vein of a mouse. 20 min post-injection, the mouse was sacrificed and the liver was harvested and processed for microscopic analysis. Examination of the liver tissue indicated significant accumulation of antibody in hepatocytes (FIG. 13). Upper left quadrant shows labeled antibodies, Upper right quadrant shows actin, lower left quadrant shows nuclei, and lower right quadrant shows a composite image.

Example 19

Masked Polynucleotide-Polymer Conjugate as In Vitro Transfection Reagent

Primary hepatocytes were harvested from adult mice (strain C57BL/6) using the two-step collagenase perfusion procedure as previously described (Klaunig 1981). Hepatocyte viability was 85-90% as determined by Trypan Blue exclusion. Hepatocytes were plated at a density of $1.5 \times 10^5$ cells per well in collagen coated 12-well plates in 1 ml of media containing 10% fetal calf serum. 24 h after plating, cells in triplicate wells were transfected without media change with siRNA using TRANSIT-SIQUEST® (Mirus Bio, Madison Wis.) according to the manufacturer's protocol, or with different amounts of siRNA conjugate. Hepatocytes were harvested 24 h after transfection and total RNA was isolated with TRIREAGENT® Reagent (Molecular Research Center, Cincinnati Ohio).

Figure 14:
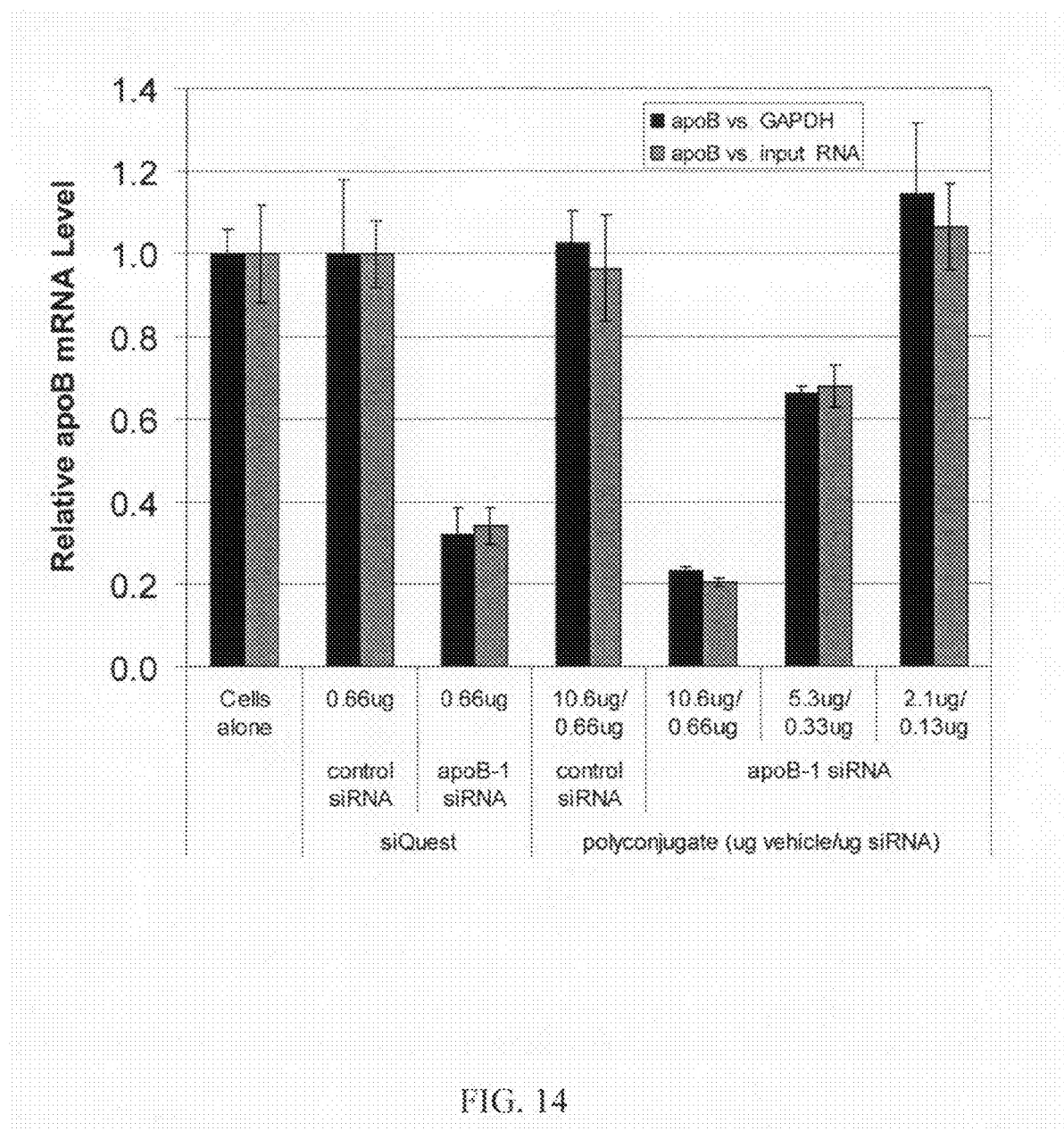
FIG. 14. Graph illustrating gene knockdown in primary hepatocytes transfected with ApoB siRNA delivered with a commercial in vitro transfection reagent or with varying amounts of ApoB siRNA polyconjugate.

To demonstrate the in vitro transfection properties of the described masked polynucleotide-polymer conjugates, apolipoprotein B (apoB)-specific siRNA was delivered to primary hepatocytes using commercially available siRNA transfection reagents or the described polynucleotide conjugates. Transfection of the primary hepatocytes with the conjugate was highly effective, resulting in nearly 80% knockdown of apoB mRNA (FIG. 14). The level of siRNA delivery, as measured by target gene knockdown was comparable to that achieved with the commercial reagent SIQUEST®. As predicted, decreasing the amount of conjugate added to the cells led to progressively decreased apoB knockdown.

Example 20

Masked Polynucleotide-Polymer Conjugate as In Vitro Transfection Reagent

Hepa-1c1c7 cells were transfected with plasmids encoding firefly and renilla luciferases using TRANSIT LT1® (Mirus Bio). 4 h after plasmid transfection, 100 ng luciferase siRNA conjugated with 9 μg PD-PLL followed by modification with CDM-Pip-LBA (45 g) was added to cells. For some sample, CDM-Pip-LBA modified 25/75-PBAVE (5 μg) was also added to cells. 48 after addition of siRNA, the cells were harvested and assayed for firefly and renilla luciferase. The amount of firefly expression was normalized to renilla for each sample and to cells not exposed to siRNA for each group. Alone, PLL-siRNA conjugates are unable to deliver siRNA to cells in vitro (white bar, FIG. 15). Addition of maleamate-masked, membrane lytic polymer PBAVE results in activity equal to commercial transfection reagent (black bar). In general, siRNA and DNA transfections appear to require excess reagent. Excess releasing polymer, above that needed to interact with siRNA, may enhance in vitro and in vivo functional delivery (release from endosomes). Due to the similar size and charge between siRNA-polymer conjugates and polymers, they can simultaneously target hepatocytes in vivo. In support of this expectation, we observed that coinjection of Cy3-labeled siRNA conjugated to PLL with Oregon Green-labeled 25/75-PBAVE did indeed colocalize to hepatocytes (see above).

Figure 15:
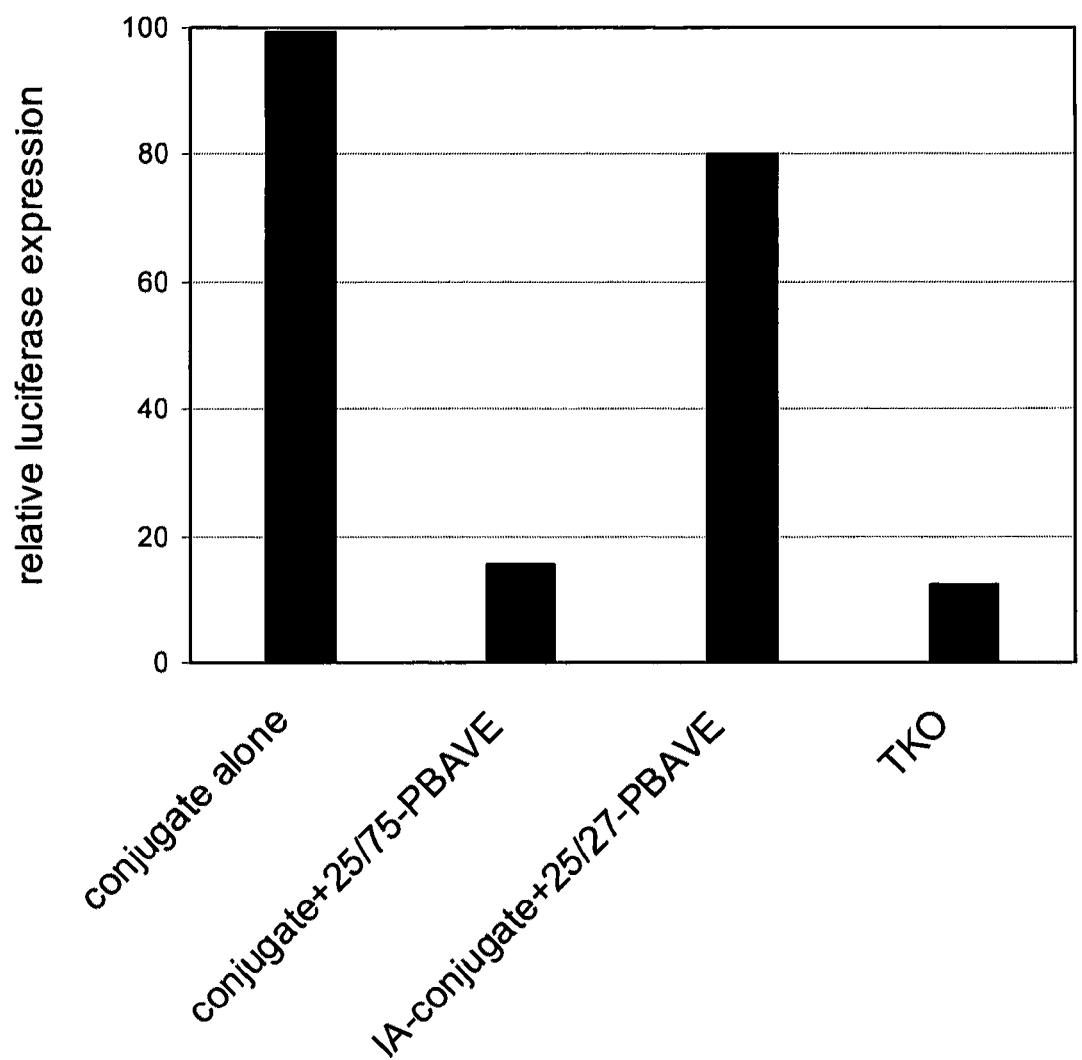
FIG. 15. Graph illustrating transfection of siRNA-conjugates to Hepa-1c1c7 cells in vitro: Conjugate alone=masked siRNA-PLL.

The in vitro activity of the siRNA conjugate with delivery polymers is equal to unconjugated siRNA transfected with commercial reagent TRANSIT TKO® (FIG. 15). Experiments in parallel with an irreversible linkage of siRNA and polymer based upon iodoacetamide alkylation chemistry (IA-conjugate spotted bar in FIG. 15) demonstrated that siRNA-polymer conjugates are not active if the conjugation is not reversible, suggesting that the disulfide bond must be reduced in order for functional delivery of siRNA (The 20% knockdown observed is due to the roughly 10% of oligo that was not conjugated, as determined by gel analysis). The activity observed for the maleamylated conjugates suggests that, even though the polymer is no longer positively-charged and interacting with the oligonucleotide by electrostatic forces, the siRNA-conjugate is resistant to degradation by nucleases in the serum. Modified siRNA analogues that are nuclease resistant may also be used.

Example 21

Labile Linkages for Attachment of Masking Agents and Polynucleotides to a Membrane Active Polymer A. pH labile bond with PEG spacer. One embodiment of an ASGP-R ligand target group may be prepared as follows:

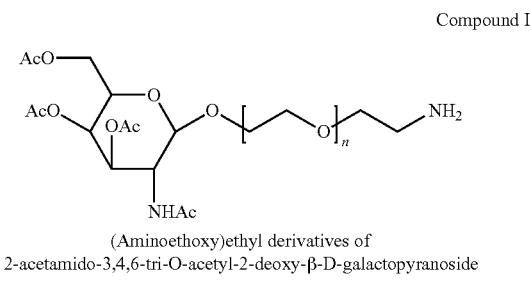

Compound I (Aminoethoxy)ethyl derivatives of 2-acetamido-3,4,6-tri-O-acetyl-2-deoxy-β-D-galactopyranoside

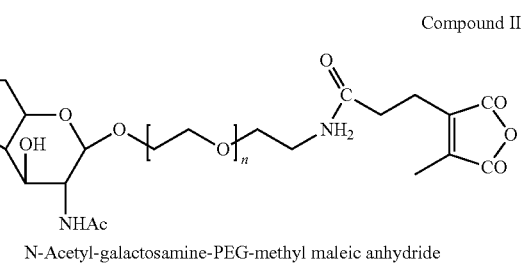

Compound II

N-Acetyl-galactosamine-PEG-methyl maleic anhydride

Compound I was used as a precursor to create compound II, a galactose targeting group masking agent capable of reversibly modifying amine-containing membrane active polymers such as PBAVE polymers. Reaction of the maleic anhydride with an anime group on the polymers results in formation of a pH labile linkage between the galactose and the polymer. Modification of a PBAVE polymer with compound II results in:

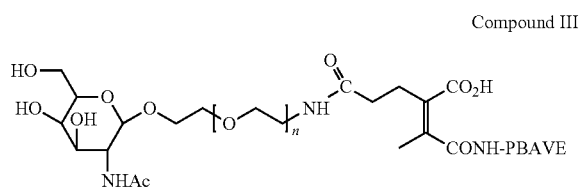

Compound III

Modification of PBAVE amino groups with compound III (0.75:1 compound III to polymer amine molar ratio) and CDM-PEG$_{500}$ (0.25 CDM-PEG to polymer amine molar ratio) resulted in a conjugate which exhibited targeting to hepatocytes in vivo. Varying spacer lengths of ethylene groups (n=1, 2, 3, or 7) were all effective in delivering siRNA to hepatocytes in vivo as evidenced by knock down of target gene expression.

B. pH labile bond with Alkyl spacer. Alkyl spacer groups may also be used as illustrated in compound V. Alkyl spacers may, however, increase the hydrophobicity of the masking agent, resulting in lower solubility of the masking agent and the conjugate.

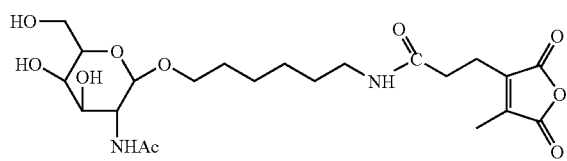

Compound V

N-Acetyl-galactosamine-C$_6$-methyl maleic anhydride masking agent

C. Multivalent targeting groups. Targeting groups with higher valency may also be utilized. Exemplary embodiments of a multivalent galactose targeting groups are illustrated below. Divalent (VI) and trivalent (VII) galactose ligands may have higher affinity for the ASGP-R.

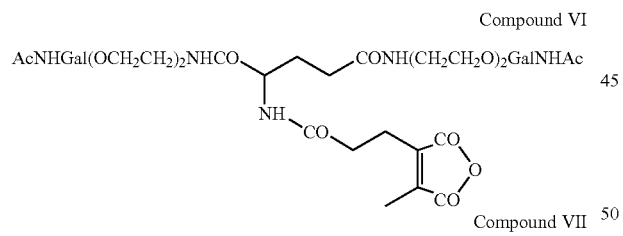

Compound VI

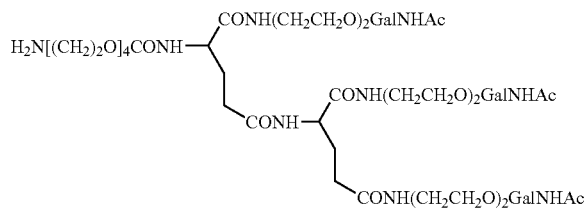

Compound VII

D. Negative control targeting ligands. Related targeting groups which have significantly lower affinity for the target cell may be used as negative controls to determine efficacy of the preferred targeting group. As an example, the ASGP-R of hepatocyte binds galactose, but not glucose. Therefore, a glucose targeting groups (VIII) may serve as a negative control in cell targeting assays.

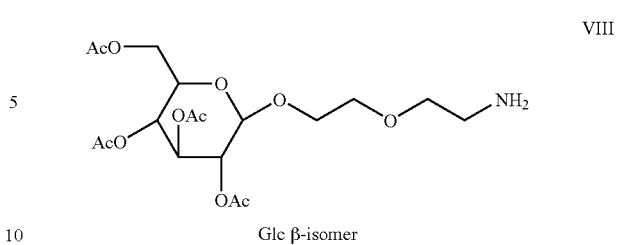

VIII

Glc β-isomer

E. Mannose targeting group. Macrophages and liver Kupffer cells are known to have receptors which bind mannose saccharides. Therefore, targeting groups with mannose residues (IX) may be used to target these cells.

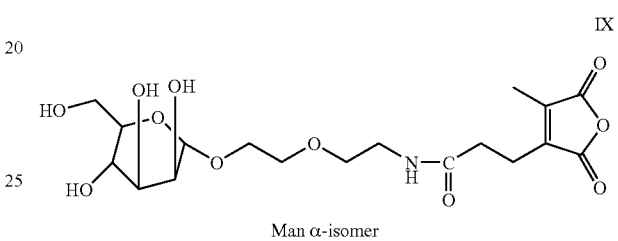

IX

Man α-isomer

F. Linkages with varying lability. Linkages of varying lability (kinetics of cleavage) can be used to connect the masking agent or polynucleotide to the membrane active polymer.

For delivery of antisense polynucleotides, it may be possible to increase the duration of knockdown by decreasing the rate of polynucleotide release from the conjugate. Disulfide bonds can be made with varying kinetics of cleavage in the reducing environment in a typical mammalian cell. A slower release of masking agent form the polymer may increase circulation time of the conjugate in vivo. For example, 5-methyl-2-iminothiolane (M2IT, Linkage X) exhibits a 4× slower rate of cleavage than an SMTP linkage (Compound XI).

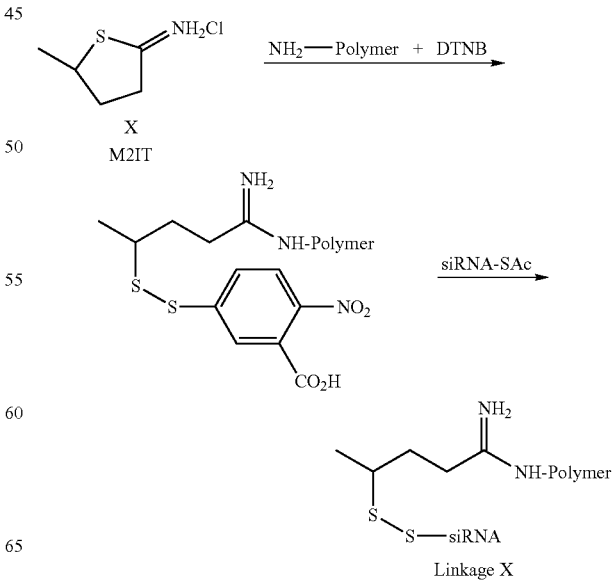

Linkage X

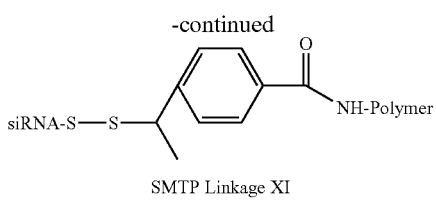

SMTP Linkage XI

The cleavage rate for Compound XII is expected to be about 30× slower than for disubstituted maleic anhydride linkages.

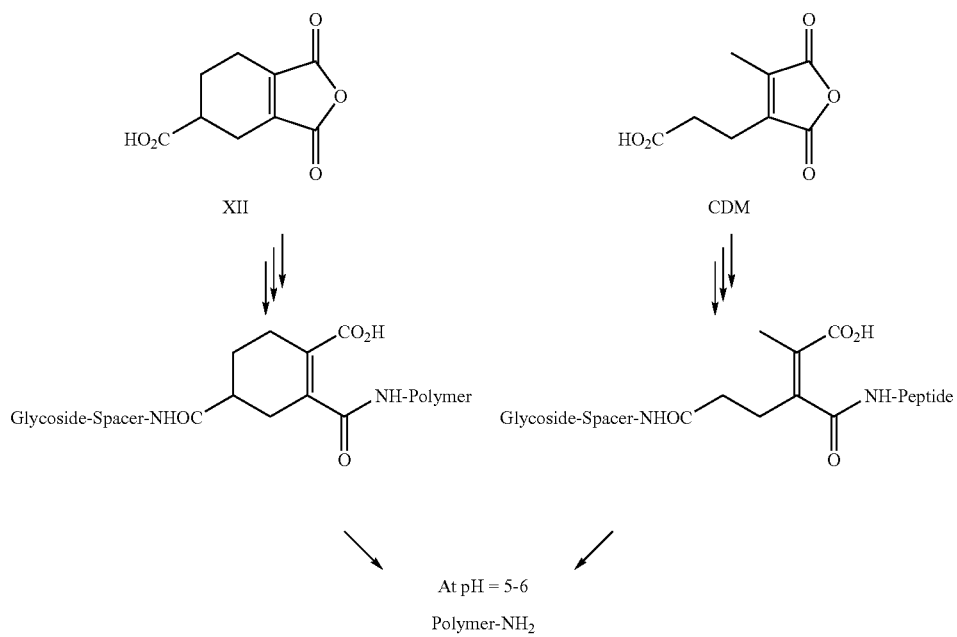

Example 22

Characterization of PBA VE and Polynucleotide-PBA VE Conjugates

Figure 16:
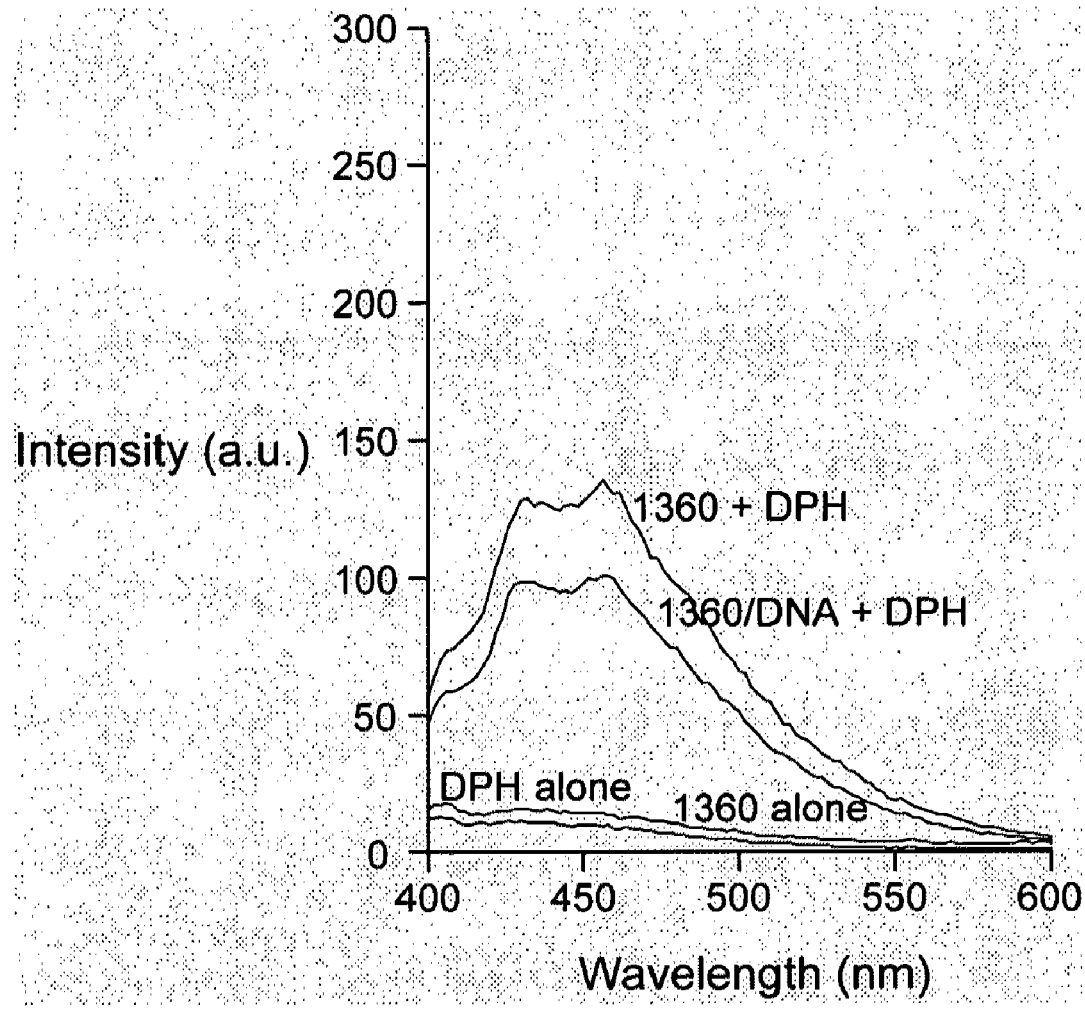
FIG. 16. Graph illustrating fluorescence of DPH in the presence or PBAVE.

A. Amphipathic analysis. 1,6-diphenyl-1,3,5-hexatriene (DPH, Invitrogen) fluorescence ($\lambda_{ex}$=350 nm; $\lambda_{em}$=452 nm) is enhanced in a hydrophobic environment. This fluorophore was used to analyze the PBAVE (DW1360) polymer. 0.5 µM (final concentration) DPH was added to 10 µg PBAVE in the presence or absence of 40 µg plasmid DNA in 0.5 ml 50 mM HEPES buffer, pH 8.0. The solution was then tested for DPH accumulation in a hydrophobic environment by measuring fluorescence of DPH. Increase DPH fluorescence in the presence of the conjugates indicates the formation of a hydrophobic environment by the polymer. Addition of excess DNA did not significantly alter DPH fluorescence (FIG. 16).

Figure 17:
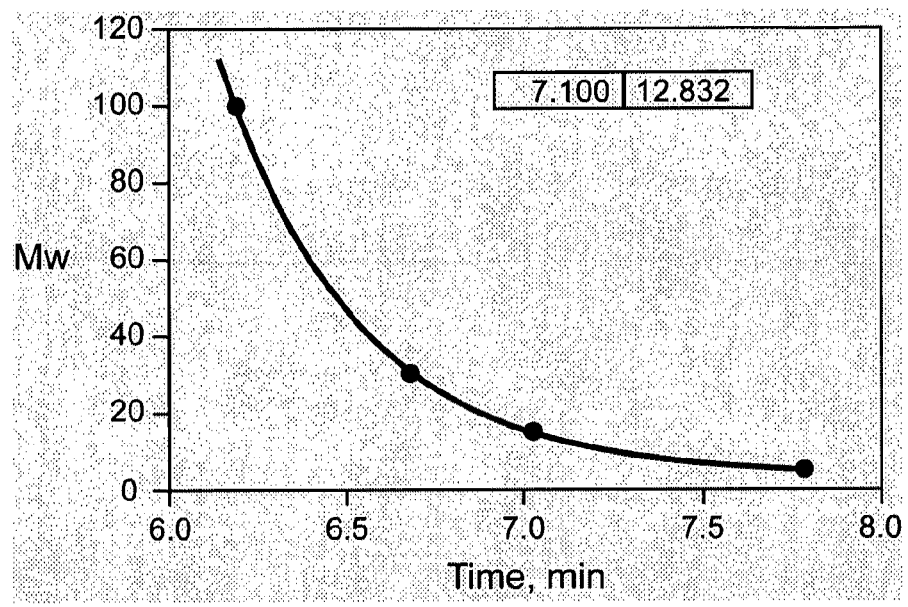
FIG. 17. Graphs illustrating A) Elution profiles of PEG standards on Shodex SB-803 column, B) Calibration plot for Shodex SB-803 column, and C) Molecular weight calculation for PBAVE polymer.

B. Molecular Weight. The molecular weight of DW1360 was determined using HPLC size exclusion chromatography and a set of polyethyleneglycols as standards (American Polymer Standard Corp.). The polymers were separated on a GPC HPLC using a Shodec SB-803 HQ column with 0.2 M LiClO$_4$, 5% AcOH in methanol. Elution of the PBAVE polymer from the column indicated a size average of about 12.8 kDa (FIG. 17)

Figure 18C:
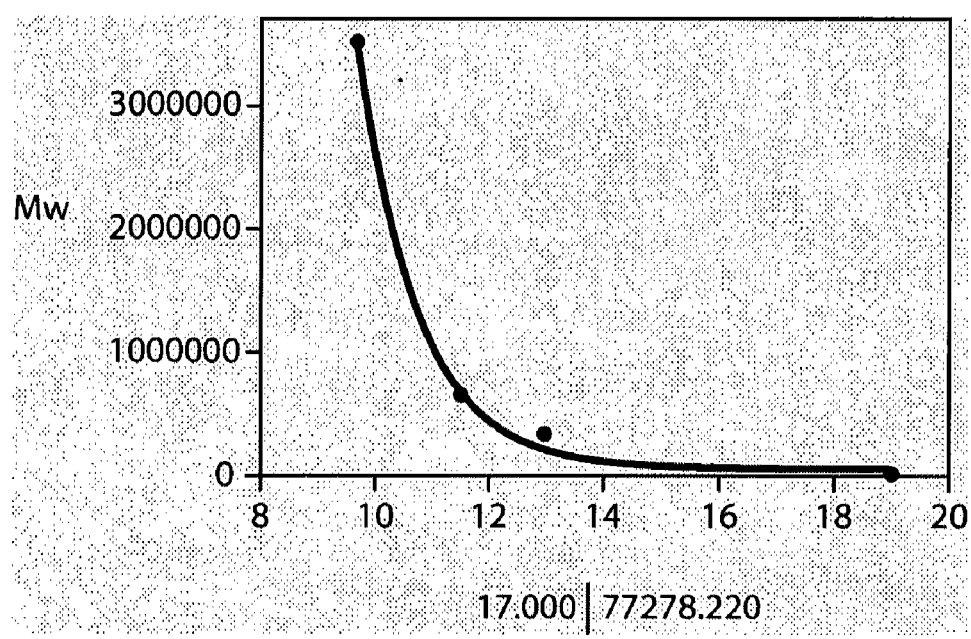
FIG. 18. Graphs illustrating A) Elution profiles of Cy3-labeled nucleic acid standards and masked polynucleotide-polymer conjugate, B) Calibration plot for the Sephacryl S-500 size exclusion chromatography, and C) Molecular weight calculation for the masked polynucleotide-polymer conjugate.

C. Molecular weight of polynucleotide-polymer conjugate. The molecular weight of masked polynucleotide-polymer conjugate was determined using FPLC size exclusion chromatography and Cy3-labeled nucleic acids as standards. The conjugate and standards were separated on a Shimadzu FPLC at using a 1×22 cm Sephacryl S-500 column and eluted with 50 mM HEPES, pH 8.0 at 1 ml/min. Elution of the conjugate from the column indicated a size average of about 77 kDa (FIG. 18).

D. Conjugate stoichiometry. The average molecular weight of the PBAVE polymer was experimentally determined to be about 13 kDa. The average molecular weight of the masked polynucleotide-polymer conjugate was experimentally determined to be about 77 kDa. The average molecule weight per charge (amine) of the PBAVE polymer was experimentally determined to be about 200 Da. The average molecular weight of the CDM masking agent was calculated to be about 550 Da. The average degree of modification of the PBAVE polymer was experimentally determined to be about 75% of available amines. The average molecular weight of the conjugated siRNA was calculated to be about 14 kDa. Using these values, the average molecular weight of the CDM-masked PBAVE polymer masking agent was calculated to be about 30 kDa. Thus, the likely stoichiometry of siRNA to masked polymer was estimated to be about 1:2.

E. Particle Sizing and Zeta Potential. The sizes of the conjugates injected in vivo were measured by light scattering at 532 nm using a Brookhaven Instruments Corporation, ZetaPlus Particle Sizer, I90. Unimodal analysis of peaks varied between 100 and 30 nm. Using multimodal analysis, the peak with the largest number (>95%) of particles were less than 50 nm and more typically less than 20 nm. Polyconjugate size can also be measured using analytical ultracentrifugation or atomic force microscopy. In the same way the zeta potential of the conjugates were measured using Brookhaven Instruments Corporation ZetaPALS. The zeta potential of the CDM-masked conjugates varied between 0 and −30 mV and more predominantly between 0 and −20 mV. Zeta potential was measure in isotonic glucose buffered at pH9 with 5 mM TAPS. Stable, non-aggregating conjugates were also formed with zeta potentials between 0 and −10 mV and between 0 and −5 mV under the same conditions. At pH 7, the conjugates would be expected to gain some positive charge due to protonation of some of the amines.

Example 23

In Vivo Delivery of Conjugate to Human Hepatoma Xenograft in Nude Mice

To demonstrate that the described conjugates can be utilized to target tumor cells CDM-NAG modified oligonucleotide-DW1360 conjugate was injected into mice that had been implanted with human hepatocarcinoma HepG2 cells subcutaneously (SC) on the flank. Six week old female athymic nude mice were obtained from Harlan Spraque Dawley (Indianapolis, Ind.). Mice were inoculated with 2 million HepG2 cells in 300 µl PBS subcutaneously on the left flank. Control colon carcinoma HT-29 cells (2 million in 300 µl of PBS) were inoculated SC on the right flank 2 weeks later. Later injection was to compensate for faster growth rate. When SC tumors grew to approximately 8 mm in width and length, CDM-NAG and CDM-PEG modified conjugate containing 10 µg Cy3-labeled 21-mer dsDNA in 200 µl delivery buffer was injected via the tail vein.

Figure 19:
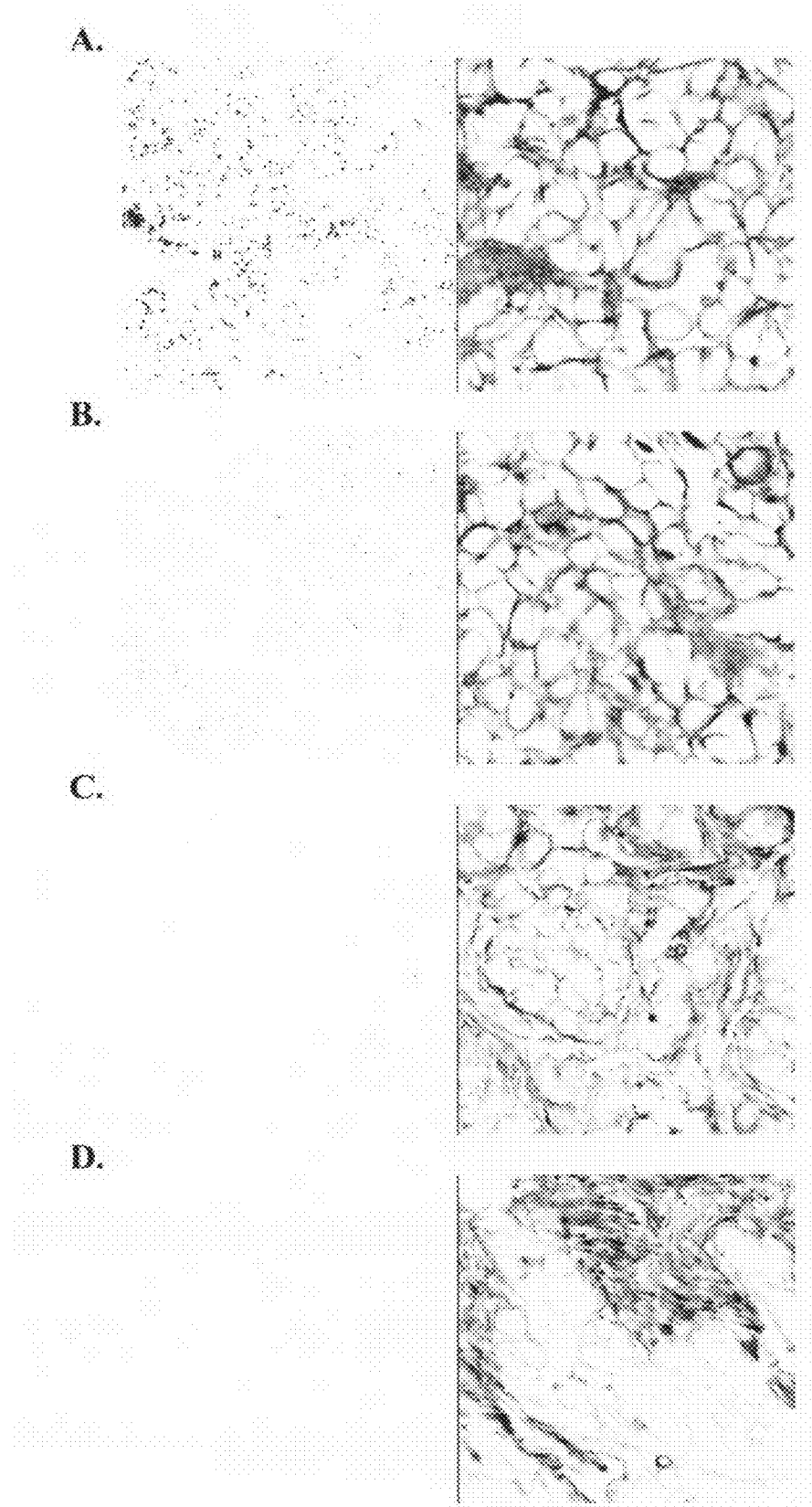
FIG. 19. Micrographs showing in vivo polynucleotide delivery to mouse galactose receptor positive tumors (A-B) or galactose receptor negative tumors (C-D) using oligonucleotide-polymer-CDM/PEG/NAG conjugates (A, C) or oligonucleotide-polymer-CDM/PEG/glucose conjugates (B, D).

Accumulation of NAG targeted conjugate was observed in a large percentage of the SC hepatoma tumor mass (30-60%, n=4, FIG. 19A). Representative area of tumor cells showing uptake is shown in FIG. 19A. A very low level of tumor targeting was observed in mice receiving glucose targeted conjugate (FIG. 19B, <5% of tumor mass, n=3). In control colon carcinoma tumors, without galactose receptor, no tumor cell signal was observed with either NAG or glucose modified conjugate (FIG. 19 C-D, n=2). Similar results were also observed using HuH-7 hepatocarcinoma cells to establish xenografts.

Example 24

Modification of Polymer with Reversible PEG Modification Prior to Conjugation 400 µg of polymer DW1360 (formed from a feed ratio of 75:20:5 amine:butyl:octadecyl vinyl ethers) was modified with 1.5 wt % SMPT. 1 h later 2 wt equivalents of a 2:1 wt:wt mixture of CDM-NAG (N-acetylgalactoseamine) and CDM-PEG (average 11 unites) was added to the polymer in the presence of 5.6 mg of HEPES base. To this solution was added 20 µg of SATA/Cy3-modified 22-mer DNA oligonucleotides. After overnight incubation, 5 wt equivalents of a 2:1 wt:wt mixture of CDM-NAG and CDM-PEG was added to the conjugate. The masked conjugate was injected in 400 µl of saline into the tail vein of a mouse. It was determined that the modification of polymer with CDM-NAG and CDM-PEG prior to conjugation did not reduce the conjugation efficiency. 1 h postinjection, the liver was harvested and frozen liver sections were prepared and processed for immunohistochemistry. TO-PRO-3® was used to stain cell nuclei. After injection of into the tail vein of mice, labeled oligonucleotide was observed in hepatocytes.

Example 25

Quantification of Amine Groups in Conjugate after CDM-Reagent Modification

Oligonucleotide-DW 1360 conjugate polymer was synthesized as described previously followed by treatment with 14 wt equivalents HEPES base and 7 wt equivalents of a 2:1 wt:wt mixture of CDM-NAG and CDM-PEG (average 11 units). One hour later, the amine content of the maleic anhydride derivative treated conjugate was measured by treatment with trinitrobenzene sulfonic acid (TNBS) in 100 mM $NaHCO_3$. When normalized to a conjugate that had not been maleamate modified, it was determined that the amount of modified amines was about 75% of total. This degree of modification may be varied by changing the amount of added maleic anhydride.

Example 26

Electrophoresis of Oligonucleotide-Polymer Conjugate and its Maleic Anhydride Derivatives Oligonucleotide-polymer DW1360 conjugates were made as described previously. The conjugate containing 1 µg of oligonucleotide was then modified with varying amounts of CDM-PEG (11 units average) and CDM-NAG. The conjugates were then placed into agarose gels (2 wt %) and electrophoresed. It was noted upon staining with ethidium bromide that the conjugates' charge was altered depending on the equivalents of maleic anhydride derivate from positive to neutral to negative.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

---

We claim:

1. A conjugate delivery system for delivering an RNA interference polynucleotide to a liver cell in vivo comprising:

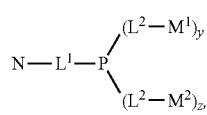

wherein,
P is a membrane active polyamine,
$L^2$ is a disubstituted maleamate linkage,
$M^1$ is a masking agent containing a galactose derivative,
$M^2$ is a masking agent containing a polyethyleneglycol,
N is an RNA interference polynucleotide,
$L^1$ is a physiologically labile covalent linkage that is orthogonal to $L^2$,
y and z are integers greater than 1 wherein the value of y and z together is greater than 50% on amines of P,
positive charge of P is neutralized and membrane activity of P is reversibly inhibited by modification of greater than 50% of P amines by attachment of $M^1$ and $M^2$ through the physiologically pH-labile linkages $L^2$, and cleavage of $L^2$ restores membrane activity of P.

2. The conjugate of claim 1 wherein the polynucleotide comprises siRNA or microRNA.

3. The conjugate of claim 1 wherein the polyamine is larger than 5 kDa.

4. The conjugate of claim 3 wherein the polyamine is larger than 7.5 kDa.

5. The conjugate of claim 4 wherein the polymer is larger than 10 kDa.

6. The conjugate of claim 1 wherein the conjugate has a zeta potential between 0 and −20 mV at pH 9.

7. The conjugate of claim 6 wherein the conjugate has a zeta potential between 0 and −10 mV at pH 9.

8. The conjugate of claim 7 wherein the conjugate has a zeta potential between 0 and −5 mV at pH 9.

9. The conjugate of claim 1 wherein $P-L^2-M^1$ has the structure:

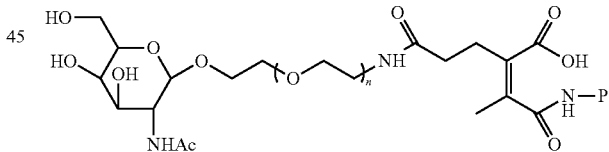

wherein n is an integer between 1 and 500.

10. The conjugate of claim 1 wherein $P-L^2-M^1$ has the structure:

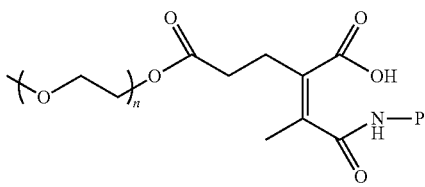

wherein n is an integer between 1 and 500.

11. The conjugate of claim 1 wherein the conjugate is smaller than 20 nm in diameter.

12. The conjugate of claim 1 wherein the conjugate is smaller than 10 nm in diameter.

13. The conjugate of claim 1 wherein the membrane active polymer consists of a polyvinylether random copolymer.

14. The conjugate of claim 1 wherein the membrane active polymer contains two or more different monomers.

15. The conjugate of claim 14 wherein the membrane active polymer contains three or more different monomers.

16. The conjugate of claim 15 wherein the monomers are selected from the group consisting of: amine-containing monomers, lower alkyl monomers, butyl monomers, higher alkyl monomers, dodecyl monomers, and octadecyl monomers.

17. The conjugate of claim 13 wherein the polyvinylether random copolymer is composed of amine-containing vinyl ether monomers, lower alkyl vinyl ether monomers, and higher alkyl vinyl ether monomers.

18. The conjugate of claim 17 wherein the lower alkyl vinyl ether consists of a butyl vinyl ether and the higher alkyl vinyl ether consists of an octadecyl vinyl ether or dodecyl vinyl ether.

19. The conjugate of claim 18 wherein the polyvinylether random copolymer is soluble in water.

20. The conjugate of claim 18 wherein the polyvinylether random copolymer is surface active.

21. The conjugate of claim 1 wherein the polymer is a biodegradable polymer.

22. The conjugate of claim 1 wherein the masking agents are reversibly linked to at least 70% of the amines on the polyamine.

23. The conjugate of claim 17 wherein the amine-containing vinyl ether monomers, lower alkyl vinyl ether monomers, and higher alkyl vinyl ether monomers are present in a ratio of 5.4-7.5 a amine-containing vinyl ether monomers:3-3.5 lower alkyl vinyl ether monomers:1 higher alkyl vinyl ether monomers.

24. The conjugate delivery system of claim 1 wherein the conjugate delivery system further comprises an excess of membrane active polyamine reversibly covalently linked to a plurality of masking agents via physiologically labile bonds wherein the excess polymer is not covalently linked to the RNA interference polynucleotide.

25. The conjugate delivery system of claim 1 wherein the conjugate is provided in a pharmaceutically acceptable carrier or diluent.

26. The conjugate of claim 2 wherein the polynucleotide is selected from the groups consisting of: DNA, RNA, dsRNA, RNA interference polynucleotide, siRNA, and miRNA.

27. A conjugate delivery system for delivering an RNA interference polynucleotide to a liver cell in vivo formed by the process comprising:
 a) forming a membrane active polyamine;
 b) forming a first masking agent comprising a disubstituted maleic anhydride containing a galactose derivative;
 c) forming a second masking agent comprising a disubstituted maleic anhydride containing a polyethyleneglycol;
 d) linking the RNA interference polynucleotide to the polyamine via a physiologically labile covalent bond that is orthogonal to a maleamate linkage;
 e) reversibly inhibiting membrane activity of the membrane active polyamine wherein the inhibiting consists of modifying 50% or more of the amines on the polyamine by reacting the polyamine with the first and second masking agents thereby linking a plurality of galactose derivatives and a plurality of polyethyleneglycols to the membrane active polymer via physiologically pH-labile disubstituted maleamate linkages.

* * * * *

SEQUENCE LISTING

<160> NUMBER OF SEQ ID NOS: 13

<210> SEQ ID NO 1
<211> LENGTH: 21
<212> TYPE: RNA
<213> ORGANISM: Mus musculus

<400> SEQUENCE: 1 gaauguggu ggcaacuuua g      21

<210> SEQ ID NO 2
<211> LENGTH: 21

-continued

```
<212> TYPE: RNA
<213> ORGANISM: Mus musculus

<400> SEQUENCE: 2
aaaguugcca cccacauuca g                                              21

<210> SEQ ID NO 3
<211> LENGTH: 21
<212> TYPE: RNA
<213> ORGANISM: Mus musculus

<400> SEQUENCE: 3
ggacaugggu uccaaauuac g                                              21

<210> SEQ ID NO 4
<211> LENGTH: 21
<212> TYPE: RNA
<213> ORGANISM: Mus musculus

<400> SEQUENCE: 4
uaauuuggaa cccauguccc g                                              21

<210> SEQ ID NO 5
<211> LENGTH: 21
<212> TYPE: RNA
<213> ORGANISM: Mus musculus

<400> SEQUENCE: 5
ucacggagcu cacagaauuc u                                              21

<210> SEQ ID NO 6
<211> LENGTH: 21
<212> TYPE: RNA
<213> ORGANISM: Mus musculus

<400> SEQUENCE: 6
aauucuguga gcuccgugac u                                              21

<210> SEQ ID NO 7
<211> LENGTH: 21
<212> TYPE: RNA
<213> ORGANISM: Mus musculus

<400> SEQUENCE: 7
ucccaaagcu ccuucaaaau u                                              21

<210> SEQ ID NO 8
<211> LENGTH: 21
<212> TYPE: RNA
<213> ORGANISM: Mus musculus

<400> SEQUENCE: 8
uuuugaagga gcuuugggaa g                                              21

<210> SEQ ID NO 9
<211> LENGTH: 21
<212> TYPE: RNA
<213> ORGANISM: Photinus pyralis

<400> SEQUENCE: 9
cuuacgcuga guacuucgau u                                              21

<210> SEQ ID NO 10
<211> LENGTH: 21
```

```
<212> TYPE: RNA
<213> ORGANISM: Photinus pyralis

<400> SEQUENCE: 10
ucgaaguacu cagcguaagu u                                              21

<210> SEQ ID NO 11
<211> LENGTH: 20
<212> TYPE: DNA
<213> ORGANISM: Mus musculus

<400> SEQUENCE: 11
aaatggtgaa ggtcggtgtg                                                20

<210> SEQ ID NO 12
<211> LENGTH: 23
<212> TYPE: DNA
<213> ORGANISM: Mus musculus

<400> SEQUENCE: 12
catgtagttg aggtcaatga agg                                            23

<210> SEQ ID NO 13
<211> LENGTH: 23
<212> TYPE: DNA
<213> ORGANISM: Mus musculus

<400> SEQUENCE: 13
cgtgccgcct ggagaaacct gcc                                            23
```